US007700554B2

(12) United States Patent
Beliveau et al.

(10) Patent No.: US 7,700,554 B2
(45) Date of Patent: Apr. 20, 2010

(54) COMPOSITIONS FOR MODULATING BLOOD-BRAIN BARRIER TRANSPORT

(75) Inventors: Richard Beliveau, Ile Des Soeurs (CA); Michel Demeule, Longueuil (CA); Joseph Yang, North Delta (CA); Malcolm L. Kennard, North Vancouver (CA); Reinhard Gabathuler, San Rafael, CA (US)

(73) Assignee: Raptor Pharmaceuticals Inc., Novato, CA (US)

( * ) Notice: Subject to any disclaimer, the term of this patent is extended or adjusted under 35 U.S.C. 154(b) by 55 days.

(21) Appl. No.: 11/580,497

(22) Filed: Oct. 13, 2006

(65) Prior Publication Data

US 2007/0167365 A1 Jul. 19, 2007

Related U.S. Application Data

(63) Continuation of application No. 10/206,448, filed on Jul. 25, 2002, now abandoned.

(60) Provisional application No. 60/308,002, filed on Jul. 25, 2001.

(51) Int. Cl.
*A61K 38/17* (2006.01)
*A61K 33/24* (2006.01)
*A61K 31/704* (2006.01)
*A61K 38/50* (2006.01)

(52) U.S. Cl. .................. 514/12; 424/649; 424/94.6
(58) Field of Classification Search .............. None
See application file for complete search history.

(56) References Cited

U.S. PATENT DOCUMENTS

| | | | |
|---|---|---|---|
| 4,018,884 A | 4/1977 | Cleeland, Jr. et al. | |
| 4,391,904 A | 7/1983 | Litman et al. | |
| 4,394,448 A | 7/1983 | Szoka, Jr. et al. | |
| 4,715,359 A * | 12/1987 | Ryo | 600/3 |
| 4,744,981 A | 5/1988 | Pavanasasivam | |
| 4,832,686 A | 5/1989 | Anderson | |
| 4,897,255 A | 1/1990 | Fritzberg et al. | |
| 4,988,496 A | 1/1991 | Srinivasan et al. | |
| 5,106,951 A | 4/1992 | Morgan, Jr. et al. | |
| 5,186,941 A | 2/1993 | Callahan et al. | |
| 5,256,413 A | 10/1993 | Haber et al. | |
| 5,288,514 A | 2/1994 | Ellman | |
| 5,474,766 A | 12/1995 | Schwartz et al. | |
| 5,519,134 A | 5/1996 | Acevedo et al. | |
| 5,525,735 A | 6/1996 | Gallop et al. | |
| 5,541,061 A | 7/1996 | Fodor et al. | |
| 5,549,974 A | 8/1996 | Holmes | |
| 5,559,410 A | 9/1996 | Papazian et al. | |
| 5,576,220 A | 11/1996 | Hudson et al. | |
| 5,604,198 A | 2/1997 | Poduslo et al. | |
| 5,650,391 A | 7/1997 | Schwartz et al. | |
| 5,672,683 A | 9/1997 | Friden et al. | |
| 5,962,012 A | 10/1999 | Lin et al. | |
| 5,962,266 A | 10/1999 | White et al. | |
| 5,977,435 A * | 11/1999 | Lefebvre et al. | 800/278 |
| 5,981,194 A | 11/1999 | Jefferies et al. | |
| 6,072,041 A | 6/2000 | Davis et al. | |
| 6,090,925 A * | 7/2000 | Woiszwillo et al. | 530/410 |
| 6,165,476 A | 12/2000 | Strom et al. | |
| 6,261,595 B1 | 7/2001 | Stanley et al. | |
| 6,331,611 B1* | 12/2001 | Murgita | 530/350 |
| 6,372,712 B1 | 4/2002 | Briesewitz et al. | |
| 6,432,412 B1* | 8/2002 | Emery et al. | 424/241.1 |
| 6,447,775 B1 | 9/2002 | Strickland et al. | |
| 6,455,494 B1 | 9/2002 | Jefferies et al. | |
| 6,743,427 B1 | 6/2004 | Schenk | |
| 2001/0025026 A1 | 9/2001 | Heartlein et al. | |
| 2003/0129186 A1 | 7/2003 | Beliveau et al. | |
| 2003/0215440 A1* | 11/2003 | Gruber et al. | 424/94.64 |

FOREIGN PATENT DOCUMENTS

| | | | |
|---|---|---|---|
| WO | WO-88/04690 | 6/1988 | |
| WO | 00/71714 | * 11/2000 | |
| WO | WO-01/59459 | 8/2001 | |
| WO | WO-02/13843 | 2/2002 | |
| WO | WO-03/009815 | 2/2003 | |

OTHER PUBLICATIONS

Rousselle 2000. Molecular Pharmacology 57:679-686.*
Williams 1992 Journal of Biological Chemistry 267:9035-9040.*
Czekay 1997 (Molecular Biology of the Cell 8:517-532).*
Maa 1998 (Journal of Pharmaceutical Sciences 87:808-812).*
Albeck, "A non-invasive transport system for GDNF across the blood-brain barrier" *Neuroreport,* 8:2293-2298 (1997).
Alemany et al., "Glycosyl Phosphatidylinositol Membrane Anchoring of Melanotransferrin (p97): Apical Compartmentalization in Intestinal Epithelial Cells," *J. Cell Sci.,* 104:1155-1162 (1993).
Altschul et al., "Basic Local Alignment Search Tool," *J. Mol. Biol.,* 215(3):403-410 (1990).
Anderson et al., "Differential Binding of Ligands to the Apolipoprotein E Receptor 2," Biochemistry, 42:9355-9364 (2003).
Anderson et al., "Dominant Thermodynamic Role of the Third Independent Receptor Binding Site in the Receptor-Associated Protein RAP," Biochemistry, 40:15408-15417 (2001).

(Continued)

*Primary Examiner*—Daniel E. Kolker
(74) *Attorney, Agent, or Firm*—Marshall, Gerstein & Borun LLP

(57) ABSTRACT

This invention provides conjugates of therapeutic or active agents with melanotransferrin or with other ligands of a melanotransferrin receptor, melanotransferrin receptor modulators, and related compositions and methods for modulating blood-brain barrier transport by providing methods of screening and selecting such conjugates, ligands, and modulators in vitro and in vivo, and methods of use of such conjugates, modulators and ligands in diagnosis and the treatment of diseases, including particularly diseases of the central nervous system or lysosomal storage diseases.

2 Claims, 46 Drawing Sheets

OTHER PUBLICATIONS

Anderson et al., "Identification of the Minimal Functional Unit in the Low Density Lipoprotein Receptor-related Protein for Binding the Receptor-associated Protein (RAP)," J. Biol. Chem., 275(28):21017-21024 (2000).
Ashcom et al., "The Human $\alpha_2$-Macroglobulin Receptor: Identification of A 420-kD Cell Surface Glycoprotein Specific for the Activated Conformation of $\alpha_2$-Macroglobulin," J. Cell. Biol., 110(4):1041-1048 (1990).
Bajari et al., "A Minimal Binding Domain of the Low Density Lipoprotein Receptor Family," Biol. Chem., 379:1053-1062 (1998).
Baker et al., "Human melanotransferrin (p97) has only one functional iron-binding site," FEBS Lett., 298(2-3):215-218 (1992).
Bickel et al., "Delivery of Peptides and Proteins Through the Blood-brain Barrier," -Adv. Drug Deliv. Rev., 46(1-3):247-279 (2001).
Bickel et al., "Pharmacologic Effects in Vivo in Brain by Vector-mediated Peptide Drug Delivery," Proc. Nalt. Acad. Sci. (USA), 90:2618-2622 (1993).
Biotech Week, p. 3 (2002).
Blair et al., "Linkage of Cytotoxic Agents to Immunoglobulins," J. Immunol. Methods, 59(2):129-143 (1983).
Blattler et al., "New Heterobifunctional Protein Cross-linking Reagent that Forms an Acid-labile Link," Biochem., 24:1517-1524 (1985).
Bogan et al., "Anatomy of Hot Spots in Protein Interfaces," J. Mol. Biol., 280:1-9 (1998).
Brown et al., "Human melanoma-associated antigen p97 is structurally and functionally related to transferrin," Nature, 296(5853):171-173 (1982).
Brown et al., "Quantitative analysis of melanoma-associated antigen p97 in normal and neoplastic tissues," Proc. Natl. Acad. Sci. (USA), 78(1):539-543 (1981).
Bu et al., "RAP, a Novel Type of ER Chaperone," Trends Cell Biol., 8(7):272-276 (1998).
Bu et al., "Receptor-associated Protein is a Folding Chaperone for Low Density Lipoprotein Receptor-related Protein," J. Biol. Chem., 271(36):22218-22224 (1996).
Bu et al., "Receptor-mediated endocytosis of tissue-type plasminogen activator by low density lipoprotein receptor-related protein on human hepatoma HepG2 cells," J. Biol. Chem., 268(17):13002-13009 (1993).
Bu, "The Roles of Receptor-Associated Protein (RAP) as a Molecular Chaperone for Members of the LDL Receptor Family," Int. Rev. Cytol., 209:79-116 (2001).
Canals et al., "Brain-Derived Neurotrophic Factor Regulates the Onset and Severity of Motor Dysfunction Asociated with Enkephalinergic Neuronal Degeneration in Huntington's Disease," J. Neuroscience, 24(35):7727-7739 (2004).
Cecchelli et al., "In vitro model for evaluating drug transport across the blood-brain barrier," Adv. Drug Deliv. Rev., 36(2-3):165-178 (1999).
Cho et al., "An unnatural biopolymer," Science, 261(5126):1303-1305 (1993).
Clackson et al., "A Hot Spot of Binding Energy in a Hormone-receptor Interface," Science, 267:383-386 (1995).
Cook et al., "Serum transferrin receptor," Annu. Rev. Med., 44:63-74 (1993).
Czekay et al., "Endocytic Trafficking of Megalin/RAP Complexes: Dissociation of the Complexes in Late Endosomes," Mol. Biol. Cell., 8(3):517-532 (1997).
Dagenais et al., "Development of an in situ mouse brain perfusion model and its application to mdr1a P-glycoprotein-deficient mice," J. Cereb. Blood Flow Metab., 20(2):381-386 (2000).
Dallaire et al., "Phosphate transport by capillaries of the blood-brain barrier," J. Biol. Chem., 267(31):22323-22327 (1992).
Dallaire et al., "Purification and Characterization of Metabolically Active Capillaries of the Blood-brain Barrier," Biochem. J., 276(Pt. 3):745-752 (1991).
Dehouck et al., "A New Function for the LDL Receptor: Transcytosis of LDL Across teh Blood-brain Barrier," J. Cell Biol., 138(4):877-889 (1997).

Dehouck et al., "Drug transfer across the blood-brain barrier: correlation between in vitro and in vivo models," J. Neurochem., 58(5):1790-1797 (1992).
DeLano et al., "Unraveling Hot Spots in Binding Interfaces" Progress and Challenges, Curr. Opin. Struct. Biol., 12:14-20 (2002).
Demeule et al., "Expression of multidrug-resistance P-glycoprotein (MDR1) in human brain tumors," Int. J. Cancer, 93(1):62-66 (2001).
Descamps et al., "Receptor-mediated transcytosis of transferrin through blood-brain barrier endothelial cells," Am. J. Physiol., 270(4 Pt.2):H1149-H1158 (1996).
Dwyer et al., "Hight Affinity RNase S-Peptide Variants Obtained by Phage Display Have a Novel 'Hot-Spot' of Binding Energy," Biochemistry, 40:13491-13500 (2001).
Fahrlander et al., "Amplifying DNA Probe Signals: A "Christmas Tree" Approach," Bio/Technology, 6:1165-1168 (1988).
Feng et al., "Progressive Sequence Alignment as a Prerequisite to Correct Phylogenetic Trees," J. Mol. Evol., 25:351-360 (1987).
Ferrer et al., "Brain-derived Neurotrophic Factor in Huntington Disease," Brain Research, 866:257-261 (2000).
Fillebeen et al., "Receptor-mediated Transcytosis of Lactoferrin Through the Blood-brain Barrier," J. Biol. Chem., 274:7011-7017 (1999).
Fisher et al., "Structure of an LDLR-RAP Complex Reveals a General Mode for Ligand Recognition by Lipoprotein Receptors," Molecular Cell, 22:277-283 (2006).
FitzGerald et al., "Pseudomonas Exotoxin-mediated Selection Yields Cells with Altered Expression of Low-density Lipoprotein Receptor-related Protein," J. Cell. Biol., 129(6):1533-1541 (1995).
Food et al., "Transport and expression in human melanomas of a transferrin-like glycosylphosphatidylinositol-anchored protein," J. Biol. Chem., 269(4):3034-3040 (1994).
Frank et al., "Binding and internalization of insulin and insulin-like growth factors by isolated brain microvessels," Diabetes, 35(6):654-661 (1986).
Gallop et al., "Applications of combinatorial technologies to drug discovery. 1. Background and peptide combinatorial libraries," J. Med. Chem., 37(9):1233-1251 (1994).
Gao et al., "Structure-based Method for Analyzing Protein-Protein Interfaces," J. Mol. Model., 10:4-54 (2004).
GenBank Accession No. AAH49517, Feb. 3, 2004.
GenBank Accession No. AAM90301, Aug. 1, 2002.
GenBank Accession No. CAA05085, Feb. 12, 1997.
GenBank Accession No. M91211, Dec. 9, 1993.
GenBank Accession No. NP_506187, Nov. 21, 2003.
GenBank Accession No. NP_649950, Mar. 24, 2004.
GenBank Accession No. P30533, Mar. 15, 2004.
GenBank Accession No. Q99068, Oct. 16, 2001.
GenBank Accession No. X 13916, Apr. 18, 1996.
GenBank Accession No. XM 015452, May 13, 2002.
GenBank Accession No. XM 130241, May 16, 2002.
GenBank Accession No. XM 143023, Nov. 16, 2002.
GenBank Accession No. XP_132029, Feb. 24, 2003.
GenBank Accession No. XP_313261, Sep. 17, 2003.
Gutierrez et al., "Murine Tumor Necrosis Factor Alpha is Transported from Blood to Brain in the Mouse," J. Neuroimmunology, 47(2):169-176 (1993).
Halperin et al., "Protein-Protein Interactions: Coupling of Structurally Conserved Residues and of Hot Spots Across Interfaces. Implications for Docking," Structure, 12:1027-1038 (2004).
Henikoff et al., "Amino Acid Substitution Matrices from Protein Blocks," Proc. Nalt. Acad. Sci. (USA), 89:10915-10919 (1989).
Herz et al, "Gene Transfer and Disruption Strategies to Elucidate Hepatic Lipoprotein Receptor Functions," Atherosciersosis, 118 Supp: S37-S41 (1995).
Herz et al., "39-kDa Protein Modulates Binding of Ligands to Low Density Lipoprotein Receptor-related Protein/$\alpha_2$-Macroglobulin Receptor," J. Biol. Chem., 266(32):21232-21238 (1991).
Herz et al., "LRP: A Multifunctional Scavenger and Signaling Receptor," J. Clin. Invest., 108(6):779-784 (2001).
Higgins et al., "Fast and Sensitive Multiple Sequence Alignments on a Microcomputer," Comput. Appl. Biosco., 5(2):151-153 (1989).

Hofmann et al., "RAGE mediates a novel proinflammatory axis: a central cell surface receptor for S100/calgranulin polypeptides," *Cell*, 97(7):889-901 (1999).

Hoogerbrugge et al., "Allogeneic Bone Marrow Transplantation for Lysosomal Storage Diseases," *Lancet*, 345(8962):1398-1402 (1995).

Horn et al., "Molecular Analysis of Ligand Binding to the Second Cluster of Complement-type Repeats of the Low Density Lipoprotein Receptor-related Protein," *J. Biol. Chem.*, 272(21):13608-13613 (1997).

Hussain, "Structural, biochemical and signaling properties of the low-density lipoprotein receptor gene family," *Front. Biosci.*, 6:D417-D428 (2001).

Jefferies et al., "Reactive microglia specifically associated with amyloid plaques in Alzheimer's disease brain tissue express melanotransferrin," *Brain Res.*, 712:122-126 (1996).

Jensen et al., "Purification of the Human Placental $\alpha$-$_2$-Macroglobulin Receptor," *FEBS Lett.*, 255(2):275-280 (1989).

Jensen et al., Binding Site Structure of One LRP-RAP Complex: Implications for a Common Ligand-Receptor Binding Motif, *J. Mol. Biol.*, 362:700-716 (2006).

Jensen, "Lysosomal Degradation of Receptor-bound Urokinase-type Plasminogen Activator is Enhanced by its Inhibitors in Human Trophoblastic Choriocarcinoma Cells," *Cell Ruglation*, 1:1043-1056 (1990).

Johnson et al., "Immobilization of proteins to a carboxymethyldextran-modified gold surface for biospecific interaction analysis in surface plasmon resonance sensors," *Anal. Biochem.*, 198(2):268-277 (1991).

Karlin et al., "Appications and Statistics for Multiple High-Scoring Segements in Molecular Sequences," *Proc. Natl. Acad. Sci.* (USA), 90(12):5873-5877 (1993).

Kells et al., "AAV-Mediated Gene Delivery of BDNF or GDNF is Neuroprotective in a Model of Huntington Disease," *Molecular Therapy*, 9(5):682-688 (2004).

Kennard et al., "Serum levels of the iron binding protein p97 are elevated in Alzheimer's disease," *Nat. Med.*, 2(11):1230-1235 (1996).

Kilic et al., "Intravenous TAT-GDNF in Protective after Focal Cerebral Ischemia in Mice," *Stroke*, 34(5):1304-1310 (2003).

Kim et al., "Serum melanotransferrin, p97 as a biochemical marker of Alzheimer's disease," *Neuropsychopharmacology*, 25(1):84-90 (2001).

King et al., "Preparation of Protein Conjugates via Intermolecular Hydrazone Linkage," *Biochem.*, 25(19):5774-5779 (1986).

Kounnas et al., "The 39-kDa Receptor-Associated Protein Interacts with Two Members of the Low Density Lipoprotein Receptor Family, 2-Macroglobulin Receptor and Glycoprotein 330," *J. Biol. Chem.*, 267(29):21162-21166 (1992).

Kusuhara et al., "Efflux Transport Systems for Drugs at the Blood-brain Barrier and Blood-cerebrospinal Fluid Barrier (Part 1)," *Drug Discov. Today*, 6(3):150-156 (2001).

Laemmli, "Cleavage of structural proteins during the assembly of the head of bacteriophage T4," *Nature*, 227(5259):680-685 (1970).

Lee et al., "RAP Uses a Histidine Switch to Regulate its Interaction with LRP in the ER and Golgi," *Mol. Cell*, 22:423-430 (2006).

Li et al., "Magnitude of the Hydrophobic Effect at Central Versus Peripheral Sites in Protein-Protein Interfaces," *Structure*, 13:297-307 (2005).

Lin et al., "GDNF: A Glial Cell Line-derived Neurotrophic Factor for Midbrain Dopaminergic Neurons," *Science*, 260(5111):1130-1132 (1993).

Lisi et al., "Preferential Megalin-mediated Transcytosis of Low-hormonogenic Thyroglobulin: a Control Mechanism for Thyroid Hormone Release," *Proc. Natl. Acad. Sci.* (USA), 100(25):14858-14863 (2003).

Liu et al., "LRP-DIT, a putative endocytic receptor gene, is frequently inactivated in non-small cell lung cancer cell lines," *Cancer Res.*, 60:1961-1967 (2000).

Liu et al., "The putative tumor suppressor LRP1B, a novel member of the low density lipoprotein (LDL) receptor family, exhibits both overlapping and distinct properties with the LDL receptor-related protein," *J. Biol. Chem.*, 276(31):28889-28896 (2001).

Mazumber et al., "Translational Control by the 3'-UTR: The Ends Specify the Means," *Trends in Biochemical Sciences*, 28:91-98 (2003).

McCormick et al., "Independent and Cooperative Roles of N-Glycans and Molecular Chaperones in the Folding and Disulfide Bond Formation of the Low-Density Lipoprotein (LDL) Receptor-Related Protein," Biochemistry, 44:5794-5803 (2005).

Medved et al., "Domain Organization of the 39-kDa Receptor-associated Protein," *J. Biol. Chem.*, 274(2):717-727 (1999).

Meilinger et al., "Removal of Lactoferrin From Plasma is Mediated by Binding to Low Density Lipoprotein Receptor-related Protein/$\alpha_2$-Macroglobulin Receptor and Transport to Endosomes," *FEBS Lett.*, 360(1):70-74 (1995).

Melman et al., "High Affinity Binding of Receptor-associated Protein to Heparin and Low Density Lipoprotein Receptor-related Protein Required Similar Basic Amino Acid Sequence Motifs," *J. Biol. Chem.*, 276(31):29338-29346 (2001).

Migliorini et al., "Allosteric Modulation of Ligand Binding to Low Density Lipoprotein Receptor-crelated Protein by the Receptor-associated Protein Requires Critical Lysine Residues within its Carboxyl-terminal Domain," J. Biol. Chem., 278(20):17986-17992 (2003).

Needleman et al., "A General Method Applicable to the Search for Similarities in the Amino Acid Sequence of Two Proteins," *J. Mol. Biol.*, 48(3):443-453 (1970).

Neels, "The Second and Fourth Cluster of Class a Cysteine-rich Repeats of the Low Density Lipoprotein Receptor-related Protein Share Ligand-binding Properties," *J. Biol. Chem.*, 274:31305-31311 (1999).

Nielsen et al., "The Solution Structure of the N-terminal Domain of $\alpha_2$-Macroglobulin Receptor-associated Protein," *Proc. Natl. Acad. Sci.* (USA), 94(14):7521-7525 (1997).

Obermoeller et al., "Differential Functions of Triplicated Repeats Suggest Two Independent Roles for the Receptor-Associated Protein as a Molecular Chaperone," J. Biol. Chem., 272(16):10761-10768 (1997).

Orlando et al., "Functional Domains of the Receptor-associated Protein (RAP)," *Proc. Natl. Acad. Sci.* (USA), 91(8):3161-3165 (1994).

Pardridge et al., "Blood-brain Barrier Biology and Methodology," *J. Neurovirol*, 5(6):556-569 (1999).

Pardridge et al., "Selective transport of an anti-transferrin receptor antibody through the blood-brain barrier in vivo," *J. Pharmacol. Exp. Ther.*, 259(1):66-70 (1991).

Pardridge, "Drug and Gene Targeting to the Brain with Molecular Trojan Horses," *Nature Reviews Drug Discovery*, 1:131-139 (2002).

Pearson et al., "Improved Tools for Biological Sequence Comparison," *Proc. Natl. Acad. Sci.* (USA), 85(8):2444-2448 (1988).

Perez-Navarro et al., "Brain-Derived Neurotrophic Factor, Neurotrophin-3, and Neurotrophic-4/5 Prevent the Death of Striatal Projection Neurons in a Rodent Model of Huntington's Disease," *J. Neurochem.*, 75:2190-2199 (2000).

Prince et al., "Lipoprotein Receptor Binding, Cellular Uptake, and Lysosomal Delivery of Fusions Between the Receptor-Associated Protein (RAP) and -L-Iduronidase or Acid-Glucosidase," *J. Biol. Chem.*, 279(33):35037-35046 (2004).

Qian et al., "Expression of iron transport proteins and excessive iron accumulation in the brain in neurodegenerative disorders," *Brain Res. Rev.*, 27:257-267 (1998).

Rall et al., "The Domain Structure of Human Receptor-associated Protein," *J. Biol. Chem.*, 273(37):24152-24157 (1998).

Reddy, "Controlled-released, Pegylation, Liposomal Formulations: New Mechanisms in the Delivery of Injectable Drugs," *Annals of Pharmacology*, 34:915-923 (2000).

Richardson, "The role of the membrane-bound tumour antigen, melanotransferrin (p97), in iron uptake by the human malignant melanoma cell," *Eur. J. Biochem.*, 267(5):1290-1298 (2000).

Rose et al., "Primary structure of the human melanoma-associated antigen p97 (melanotransferrin) deduced from the mRNA sequence," *Proc. Natl. Acad. Sci.* (USA), 83:1261-1265 (1986).

Russell et al., "Recombinant Proteins for Genetic Disease," *Clinical Genetics*, 55:389-394 (1999).

Savonen et al., "The Carboxyl-terminal Domain of Receptor-associated Protein Facilitates Proper Folding and Trafficking of the Very Low Density Lipoprotein Receptor by Interaction with the Three Amino-terminal Ligand-binding Repeats of the Receptor," *J. Biol. Chem.*, 274(36):25877-25882 (1999).

Schimdt et al., "The endothelial cell binding site for advanced glycation end products consists of a complex: an integral membrane protein and a lactoferrin-like polypeptide," *J. Biol. Chem.*, 269(13):9882-9888 (1994).

Schullek, "A high-density screening format for encoded combinatorial libraries: assay miniaturization and its application to enzymatic reactions," *Anal. Biochem.*, 246:20-29 (1997).

Shibata et al., "Clearance of Alzheimer's amyloid-ss(1-40) peptide from brain by LDL receptor-related protein-1 at the blood-brain barrier," *J. Clin. Invest.*, 106:1489-1499 (2000).

Smith et al., "Comparison of Biosequences," *Adv. Appl. Math.*, 2:482-489 (1981).

Spires et al., "Environmental Enrichment Rescues Protein Deficits in a Mouse Model of Huntington's Disease, Indicating a Possible Disease Mechanism," *J. Neuroscience*, 24(9):2270-2276 (2004).

Srinivasachar et al., "New Protein Cross-linking Reagents that are Cleaved by Mild Acid," *Biochem.*, 28(6):2501-2509 (1989).

Strickland et al., "LDL Receptor-related Protein (LRP): A Multiligand Receptor," *Fibrinolysis 8* (Supp. 1):204-215 (1994).

Swiss-Prot Primary Accession No. Q07954.

Swiss-Prot Primary Accession No. Q15109.

Takahashi et al., "Rabbit Very Low Density Lipoprotein Receptor: A Low Density Lipoprotein Receptor-like Protein with Distinct Ligand Specificity," *Proc. Natl. Acad. Sci.* (USA), 89(19):9252-9256 (1992).

Thompson et al., "Clustal W: Improving the Sensitivity of Progressive Multiple Sequence Alignment Through Sequence Weighting, Position-specific Gap Penalties and Weight Matrix Choice," *Nucleic Acid Res.*, 22(22):4673-4680 (1994).

Tsuji et al., "Carrier-mediated or Specialized Transport of Drugs Across teh Blood-brain Barrier," *Adv. Drug Deliv. Rev.*, 36(2-3):277-290 (1999).

Underhill et al., "Endocytosis and Lysosomal Delivery of Tissue Plasminogen Activator-Inhibitor I Complexes in Hep G2 Cells," *Blood*, 80:2746-2754 (1992).

Van den Hout et al., "Recombinant Human α-glucosidase from Rabbit Milk in Pompe Patients," *Lancet*, 356:397-398 (2000).

Warshawsky et al., "Binding Analysis of Amino-terminal and Carboxyl-terminal Regions of the 39-kDa Protein to the Low Density Lipoprotein Receptor-related Protein," *J. Biol. Chem.*, 269(5):3325-3330 (1994).

Wilchek et al., "The Avidin-Biotin Complex in Bioanalytical Applications," *Anal. Biochem.*, 171:1-32 (1988).

Williams et al., "A Novel Mechanism for Controlling the Activity of $\alpha_{-2}$-Macroglobulin Receptor/Low Density Lipoprotein Receptor-related Protein," *J. Biol. Chem.*, 267(13):9035-9040 (1992).

Willnow et al., "Low Density Lipoprotein Receptor-related Protein and gp330 Bind Similar Ligands, Including Plasminogen Activator-inhibitor Complexes and Lactoferrin, an Inhibitor of Chylomicron Remnant Clearance," *J. Biol. Chem.*, 267(36):26172-26180 (1992).

Wisselaar et al., "Structural and Functional Changes of Lysosomal Acid α-Glucosidase During Intracellular Transport and Maturation," *J. Biol. Chem.*, 268(3):2223-2231 (1993).

Woodbury et al., "Identification of a cell surface protein, p97, in human melanomas and certain other neoplasms," *Proc. Natl. Acad. Sci.* (USA), 77(4):2183-2187 (1980).

Yenofsky et al., "A Mutant Neomycin Phosphotransferase II Gene Reduces the Resistance of Transformants to Antibiotic Selection Pressure," *Proc. Natl. Acad. Sci.* (USA), 87(9):3435-3439 (1990).

Zlokovic, "Glycoprotein 330-megalin: Probable Role in Receptor-mediated Transport of Apolipoprotein J Alone and in a Complex wtih Alzheimer Disease Amyloid Beta at teh Blood-brain and Blood-cerebrospinal Fluid Barriers," *Proc. Natl. Acad. Sci.* (USA), 93:4229-4234 (1996).

Zuccato et al., "Loss of Huntingtin-Mediated BDNF Gene Transcription in Huntington's Disease," *Science*, 293:493-498 (2001).

\* cited by examiner

Involvement of LRP on P97 transcytosis

A. Effect of other ligands on P97 transcytosis

B. Effect of P97 on lactoferrin transcytosis

C. Ligands for LRP and megalin

| | LRP | Megalin |
|---|---|---|
| Lactoferrin | Yes | Yes |
| RAP | Yes | Yes |
| Aprotinin | Yes | Yes |
| BSA | No | Yes |

Transcellular colocalization of P97 and clathrin

FIGURE 21

Immunodetection of LRP/LRP1B in various astrocytomas, normal astrocytes and brain capillaries A. Various cell types B. Rat astrocytes and astrocytomas

- BBM: renal brush-border membranes (positive control)

COMPOSITIONS FOR MODULATING BLOOD-BRAIN BARRIER TRANSPORT

CROSS-REFERENCE TO RELATED APPLICATIONS

This application claims priority of U.S. Patent Application No. 60/308,002 filed Jul. 25, 2001. The contents of which are each incorporated herein by reference in their entirety.

FIELD OF THE INVENTION

The present invention relates to compositions and methods for modulating blood-brain barrier transport of compounds. In addition, the present invention provides screening assays for identifying compounds that are useful for modulating transport across the blood-brain barrier.

BACKGROUND OF THE INVENTION

In the early 1980's, melanotransferrin (MTf) was identified as an oncofetal antigen that was either not expressed, or only slightly expressed in normal tissues, but was found in much larger amounts in neoplastic cells (especially malignant melanoma cells) and fetal tissues (Woodbury, et al., P.N.A.S. USA, 77:2183-2187 (1980)). More recently, there have been additional reports of human MTf being identified in normal tissues, including sweat gland ducts, liver endothelial cells and the endothelium and reactive microglia of the brain (Jefferies, et al., Brain Res., 712:122-126 (1996); and Rothenberger, et al., Brain Res., 712:117-121 (1996)). Interestingly, normal serum contains very low levels of soluble circulating MTf, but increased soluble serum MTf has been found in patients with advanced Alzheimer's Disease (Kennard, et al., Nat. Med., 2:1230-1235 (1996); U.S. Pat. No. 5,981,194)

The biochemical role and metabolism of MTf has proven difficult to elucidate. Based on appearances, MTf is deceptively similar to transferrin (Tf) and lactotransfernin (lactoferrin or Lf). In humans, these proteins share a 37-39% amino acid sequence homology. In particular, each of these proteins reversibly binds iron, and their N-terminal iron binding domains are quite similar (Baker, et al., *TIBS*, 12:350-353 (1987)).

However, functional parallels between these proteins have not been confirmed. For one thing, unlike Tf and Lf, MTf exists in both a membrane bound form and a serum soluble form. Further, in contrast to Tf and Lf, no cellular receptor for MTf has been identified. Serum soluble Tf is known to be taken into cells in an energy-dependent process mediated by the transferrin receptor (Tf-R) (Cook, et al., *Annu. Rev. Med.,* 44:63-74 (1993)). Lf internalization is also likely to be mediated by a receptor mediated process (Fillebeen, et al., *J. Biol. Chem.,* 274(11):7011-7017 (1999)). Two known receptors for Lf are LRP1 and RAGE, although others may exist (Meilinger, et al., *FEBS Letters,* 360:70-74 (1995); Schmidt, *J. Biol. Chem.,* 269(13):9882-9888 (1994)).

Although it has been postulated that MTf is an alternate ligand for Tf-R (see, U.S. Pat. No. 5,981,194), no published data confirms this finding. Further, although various studies have confirmed iron transport into cells by membrane bound MTf, it occurs only in cells where membrane bound MTf is overexpressed well beyond physiological levels (Richardson, *Eur. J. Biochem.,* 267:1290-1298 (2000)).

Therapeutic and diagnostic agents conjugated to soluble MTf are the basis of recently filed U.S. Provisional Patent Application Nos. 60/226,242 and 60/226,254, the teachings of which are incorporated herein by reference for all purposes.

The blood-brain barrier (BBB) performs a neuroprotective function by tightly controlling access to the brain; consequently it also impedes access of pharmacological agents to cerebral tissues, necessitating the use of vectors for their transit. Blood-brain barrier (BBB) permeability is frequently a rate-limiting factor for the penetration of drugs or peptides into the central nervous system (CNS) (see Pardridge, W. M. *J. Neurovirol.* 5: 556-569 (1999); Bickel, U., Yoshikawa, T. & Pardridge, W. M. *Adv. Drug Deliv. Rev.* 46: 247-279 (2001). The brain is shielded against potentially toxic substances by the BBB, which is formed by brain capillary endothelial cells that are closely sealed by tight junctions. In addition, brain capillaries possess few fenestrae and few endocytic vesicles, compared to the capillaries of other organs (see Pardridge, W. M. *J. Neurovirol.* 5: 556-569 (1999)). There is little transit across the BBB of large, hydrophilic molecules aside from some specific proteins such as transferrin, lactoferrin and low-density lipoproteins, which are taken up by receptor-mediated endocytosis (see Pardridge, W. M. *J. Neurovirol.* 5: 556-569 (1999); Tsuji, A. & Tamai, I. *Adv. Drug Deliv. Rev.* 36: 277-290 (1999); Kusuhara, H. & Sugiyama, Y. *Drug Discov. Today* 6:150-156 (2001); Dehouck, B. et al. *J. Cell. Biol.* 138: 877-889 (1997); and Fillebeen, C. et al. *J. Biol. Chem.* 274: 7011-7017 (1999).

In order to understand and improve the delivery of therapeutic agents into cells, it is highly desirable to understand the receptors and metabolic basis of MTf activity. It is an object of this invention to identify the receptor for MTf, and to provide methods and compounds for improving the delivery of therapeutic and diagnostic agents into cells, in particular, therapeutic and diagnostic agents conjugated to MTf, and particularly their delivery across the blood-brain barrier.

BRIEF SUMMARY OF THE INVENTION

The present invention provides compositions and methods for modulating trancystosis, endocytosis, and blood-brain barrier transport of compounds. In addition, the present invention provides screening assays for identifying compounds that are useful for modulating transport across the blood-brain barrier and for delivering active agents conjugated to such agents which undergo endocytosis or transcytosis upon binding to the LRP (e.g., LRP1 and LRP1B) receptor.

In one aspect, the invention provides methods for screening compounds for the ability to modulate the endocytosis or transcytosis of p97 and p97 conjugated to active agents by assessing their ability to bind a low density lipoprotein receptor related protein (LRP). In another aspect the invention, provides modulators of the endocytosis or transcytosis of p97 and p97 conjugated to active agents. In another aspect, the invention provides conjugates of compounds (e.g., ligands) which bind to the LRP receptor and which undergo endocytosis or transcytosis upon binding to the LRP receptor. In another aspect, the invention provides methods of determining the capability of a given cell, cell type, or tissue to endocytose or transcytose p97 or a p97 conjugate to an active agent by measuring the expression of an LRP receptor nucleic acid or protein of the cell, cell type, or tissue.

In another aspect, the invention provides ligands and modulators of the LRP family of receptors for use as modulators of p97 transcytosis. In another aspect, the invention provides conjugates of LRP receptor ligands for use in delivering therapeutic agents across the blood brain barrier and/or to an intracellular compartment, particularly the lysosome. In another aspect, the invention provides methods for modulating the expression of LRP receptors by administering p97.

In one embodiment, the receptor is the LRP1 receptor. In a preferred embodiment, the receptor is the LRP1B receptor.

In one embodiment, the present invention provides a method for identifying a compound that modulates or binds to a melanotransferrin receptor ("MTf-R" or "p97 receptor"), the method comprises contacting the compound with the p97 receptor and determining the effect of LRP receptor ligands (e.g., lactoferrin, p97, BSA, aprotinin, and RAP) on the interaction of the compound with the receptor. In another embodiment, one or more LRP receptor ligands (e.g., lactoferrin, RAP, BSA, aprotinin, and p97) are individually contacted with the p97 receptor and the effect of the compound on the interaction of each compound with the p97 receptor is respectively determined. In one embodiment, the functional effect is an effect on transcytosis. In another embodiment, the effect is on endocytosis. In another embodiment, the effect is on receptor binding as measured by the changes in the binding, for instance, of RAP, p97, or lactoferrin to the p97 receptor. In certain embodiments, the method is a high throughput screening assay. In a preferred embodiment, the receptor is the LRP1 receptor. In a more preferred embodiment, the receptor is the LRP1B receptor.

In one embodiment, the invention provides a method for identifying a selective modulator of p97 receptor activity, by contacting the modulator and a ligand of the LDL-R receptor family ligand with the melanotransferrin receptor and determining the ability of one to affect the binding or interaction of the other with the melanotransferrin receptor. In a preferred embodiment, the LDL-R receptor ligand is selected from PAI-1 (plasminogen activator inhibitor type-1), plasminogen, pro-uPA (pro-urokinase plasminogen activator), tissue factor inhibitor, tPA (tissue type plasminogen activator), activated $\alpha_2$-macroglobulin, $\alpha_1$-chymotrypsin, cathepsin G, lactoferrin, RAP (receptor associated protein), thyroglobulin, circumsporozite protein, saposin, gentamycin, polymixin B, pseudomonas exotoxin A, seminal vesicle secretory protein A, thrombospondin −1, β-VLDL, chylomicron remnants, IDL, Lp(a), VLDL (very low density lipoprotein), ApoB100 (apolipoprotein B 100), and Apolipoprotein E (Apo E). In a further embodiment, a plurality of such ligands are selected and the selectivity of the compound for the receptor is assessed according to how similarly to p97 the compound's interaction with the receptor is affected by such ligands. In a further embodiment, the LDL-R receptor ligand is a LRP receptor ligand. In a more preferred embodiment, the LRP receptor ligand is an LRP1 receptor ligand or an LRP1B receptor ligand. In one embodiment, the effect on binding is assessed indirectly by a functional effect (e.g., transcytosis, endocytosis). In another embodiment, the effect is on receptor binding as measured by the changes in the binding, for instance, of RAP, p97, or lactoferrin from the p97 receptor. In certain embodiments, the method is a high throughput screening assay. In a further embodiment, the method is a BioCore method. In a preferred embodiment, the receptor is the LRP1 receptor. In a more preferred embodiment, the receptor is the LRP1B receptor. In another embodiment, the screening assay is measures the competitive displacement of a ligand, preferably p97, of the p97 receptor.

In one embodiment, the melanotransferrin receptor modulator or ligand has neurological activity such that it is useful in the treatment, prophylaxis or diagnosis of a neurological disorder. In other embodiments, the melanotransferrin receptor modulator or ligand is useful for the modulation of the uptake of melanotransfernin conjugated therapeutic agents into the brain. In still other embodiments the compound is useful for reducing a neurological side-effect of such a therapeutic agent. In a preferred embodiment, the disease or disorder is Alzheimer's disease.

In one embodiment, the p97 modulatory compound has neurological activity such that it is useful in the treatment, prophylaxis or diagnosis of a neurological disorder. In other embodiments, the compound is useful for the modulation of the uptake of melanotransferrin conjugated therapeutic agents into the brain. In still other embodiments, the compound is useful for reducing a neurological side-effect of a therapeutic agent. In another embodiment, the present invention provides a method of treating a neurological disorder in a patient, the method comprising administering to the patient a therapeutically effective amount of the modulatory compound.

In one embodiment, the p97 conjugate or p97 receptor ligand-conjugate comprises a therapeutic agent useful in treating a lysosomal storage disease. In one embodiment, the therapeutic agent is an enzyme deficient in a patient having such a disorder. In one embodiment the enzyme is iduronidase. In another embodiment, the present invention provides a method of treating a lysosomal storage disease in a patient, the method comprising administering to the patient with a lysosomal storage disease a therapeutically effective amount of p97 conjugated to an enzyme with an activity which is deficient in the lysosomal storage disease. In one embodiment, a modulator or LRP or LRP1B is co-administered to modulate the therapeutic or adverse effects of such a conjugate. In one embodiment, the conjuate is a fusion protein comprising a p97 portion and an enzyme portion wherein the enzyme provides the enzymatic activity deficient in the lysosomal storage disease. In one embodiment the enzyme is $\alpha$-L-iduronidase. In one embodiment, the p97 portion is a fragment of p97 sufficient for the endocytosis or transcytosis of the conjugate or fusion protein.

In one embodiment, the p97 conjugate or p97 receptor modulator-conjugate comprises a therapeutic agent useful in treating a CNS tumor such as a glioblastoma. In one embodiment, the therapeutic agents is cancer chemotherapeutic agent. In another embodiment, the present invention provides a method of treating a patient with a brain or CNS tumor or glioblastoma by administering to the patient a therapeutically effective amount of p97 conjugated to the chemotherapeutic agent. In a preferred embodiment, the conjugate binds to the LRP1B receptor. In one embodiment, a modulator or LRP or LRP1B is co-administered to modulate the therapeutic or adverse effects of such a conjugate.

In another embodiment, the present invention provides a method of modulating a melanotransferrin receptor ("MTf-R"), the method comprises contacting the MTf-R with a modulator identified using the above method.

In yet another embodiment, the present invention provides a method for increasing the uptake of a melanotransferrin conjugated therapeutic agent into the brain of a patient, the method comprising administering a modulator of MTf-R biological activity and the melanotransferrin conjugated therapeutic agent. In one embodiment, the modulator of MTf-R biological activity and the melanotransferrin conjugated therapeutic agent are administered contemporaneously. In another embodiment, the modulator of MTf-R biological activity and the melanotransferrin conjugated therapeutic agent are administered sequentially.

In still another embodiment, the present invention provides a method of reducing the uptake of a melanotransferrin conjugated therapeutic agent into the brain of a patient, the method comprising administering a modulator of MTf-R biological activity with a melanotransferrin conjugated therapeutic agent, wherein they are administered either contemporaneously or sequentially. In certain embodiments, the modulator is first identified according to the above method.

The present invention also provides modulators of MTf-R biological activity, wherein the modulator is identified using the above method. Preferably, the modulator is useful for reducing a neurological side-effect of a therapeutic agent.

In yet another embodiment, the present invention provides a method of identifying a compound that modulates melanotransferrin-mediated ("MTf-mediated") iron uptake, the method comprising: contacting a cell expressing MTf on its surface with the compound in the presence of MTf bound to iron ("holo-MTf") and in the absence of transferring and determining the amount of iron uptake into the cell. In certain embodiments, the compound increases the amount of iron uptake into the cell. In other embodiments, the compound decreases the amount of iron uptake into the cell.

In another aspect, the invention provides pharmaceutical compositions comprising such modulators, conjugates, and ligands and methods of using such pharmaceutical compositions. In one embodiment, the invention provides a pharmaceutical composition comprising a p97 receptor ligand conjugate for delivering an active agent across the blood brain barrier or into an intracellular compartment. The conjugate can be administered in a pharmaceutically acceptable carrier or diluent.

In other embodiments, a fusion protein comprising a peptide ligand of the LRP1 or LRP1B receptor may be used as the conjugate. The conjugate may therefore be a chimeric fusion protein combining a p97 peptide portion with a peptide active agent portion. The fusion protein active agent may be a substance having therapeutic activity such as a growth factor or lymphokine or peptide drug. The active agent may be an enzyme or other protein. In a preferred embodiment, the fusion protein comprises an active agent which is an enzyme that is deficient or has an activity deficient in a lysosomal storage disease. In particular, enzymes such as α-L-iduronidase or N-acetylgalactosamine 4-sulfatase are contemplated. The invention is also directed to embodiments where such a fusion protein is administered to a subject having a lysosomal storage disease. In other embodiments, the enzyme is an enzyme deficient in a human disease such as PKU (e.g., phenylase). In other embodiments, the enzyme is selected for its beneficial effect (e.g. heparinase I to limit the action of heparin). Such conjugates may alternatively be conjugated by synthetic chemistry reactions or joined by linker groups. One of ordinary skill in the art would understand how to make such fusion proteins. See, for instance, U.S. Patent Application No. US 2001/0025026A1, published Sep. 27, 2001. In some embodiments, the fusion protein may be formed from expression of a nucleic acid encoding the full amino acid sequence of the chimeric protein. In other embodiments, the chimeric fusion protein may be formed by a synthetic reaction combining the two peptides portions via a peptide bond directly linking the two portions.

In other embodiments, the conjugate is alternatively formed by non-covalent bonds between the carrier and an antibody to which the active agent is attached.

The invention also relates to a method of delivering an active agent across the blood brain barrier comprising administering a conjugate of p97 or another ligand of the LRP1B receptor which undergoes endocystosis or transcytosis. The compositions of the invention may also be used for delivering an agent across the blood eye or blood placenta barrier or intracellular to a lysosome.

In some embodiments, the conjugate according to the invention does not comprise p97, RAP, aprotinin, lactoferrin, RAP, or aprotinin, or or portions thereof with LRP1B or LRP binding activity. In some embodiments, the conjugate according to the invention does not comprise PAI-1, plasminogen, pro-uPA, tissue factor inhibitor, tPA, activated $\alpha_2$-macroglobulin, $\alpha_1$-chyniotrypsin, cathepsin G, lactoferrin, thyroglobulin, circumsporozite protein, saposin, gentamycin, polymixin B, pseudomonas exotoxin A, seminal vesicle secretory protein A, thrombospondin -1, β-VLDL, chylomicron remnants, IDL, Lp(a), VLDL (very low density lipoprotein), ApoB100 (apolipoprotein B 100), and Apolipoprotein E (Apo E), or portions thereof with LRP1B or LRP binding activity.

In some embodiments according to the invention, the conjugate comprises PAI-1, plasminogen, pro-uPA, tissue factor inhibitor, tPA, activated $\alpha_2$-macroglobulin, $\alpha_1$-chymotrypsin, cathepsin G, lactoferrin, thyroglobulin, circumsporozite protein, saposin, gentamycin, polymixin B, pseudomonas exotoxin A, seminal vesicle secretory protein A, thrombospondin -1, β-VLDL, chylomicron remnants, IDL, Lp(a), VLDL (very low density lipoprotein), ApoB100 (apolipoprotein B 100), and Apolipoprotein E (Apo E), or portions thereof with LRP1B or LRP binding activity.

In preferred embodiments of the invention, the p97 or LRP1 or LRP1B ligand or modulator of human or mammalian origin. In other embodiments, the ligand is the native compound from the human or mammal. In other embodiments, the ligand is substantially homologous (at least 60% identical in amino acid sequence or atomic structure) to the native or endogenous ligand. In other embodiments, the p97 receptor is human. In other embodiments, the subject to which the conjugate, modulator, or ligand is to be administered is human.

BRIEF DESCRIPTION OF THE DRAWINGS

FIG. 1. Permeability coefficient (Pe) of sucrose with BBCECs. The permeability coefficient (Pe) for sucrose was calculated as previously described (Dehouck, et al., *J. Neurochem.*, 58:1790-1797 (1992)) using filters coated or non-coated with BBCE cells co-cultured cultured with astrocytes. Briefly, coated or non-coated filters with BBCE cells were transferred to 6-well plates containing 2 ml of Ringer-Hepes per well (basolateral compartment) for 2 hrs at 37° C. In each apical chamber, the culture medium was replaced by 1 ml Ringer-Hepes containing labeled [$^{14}$C]-sucrose. At different times, inserts were placed into another well. At the end of the experiments, amounts of the radiotracers in the basolateral compartment were measured in a liquid scintillation counter. The results were plotted as the sucrose clearance (μl) as a function of time (min). The permeability of sucrose with non-coated filters with BBCE cells (PSf) and with coated filters with BBCE cells (PSt) were obtained. The results were plotted as the clearance of [$^{14}$C]-sucrose (μl) as a function of time (min). PS=permeability×surface area of a filter of the coculture; PSt=permeability of the filter and endothelial monolayer; PSf=permeability of a filter coated with collagen and astrocytes plated on the bottom side of the filter. The permeability coefficient (Pe) of the endothelial monolayer was calculated as:

$$\text{Clearance } (\mu l) = \frac{[C]_A \times V_A}{[C]_L} \quad \begin{aligned} [C]_A &= \text{Abluminal tracer concentration} \\ V_A &= \text{Volume of abluminal chamber} \\ [C]_L &= \text{Luminal tracer concentration} \end{aligned} \quad 1)$$

$$1/Pe = (1/PSt - 1/PSf)/\text{filter area } (4.2 \text{ cm}^2) \quad 2)$$

Figure 1:
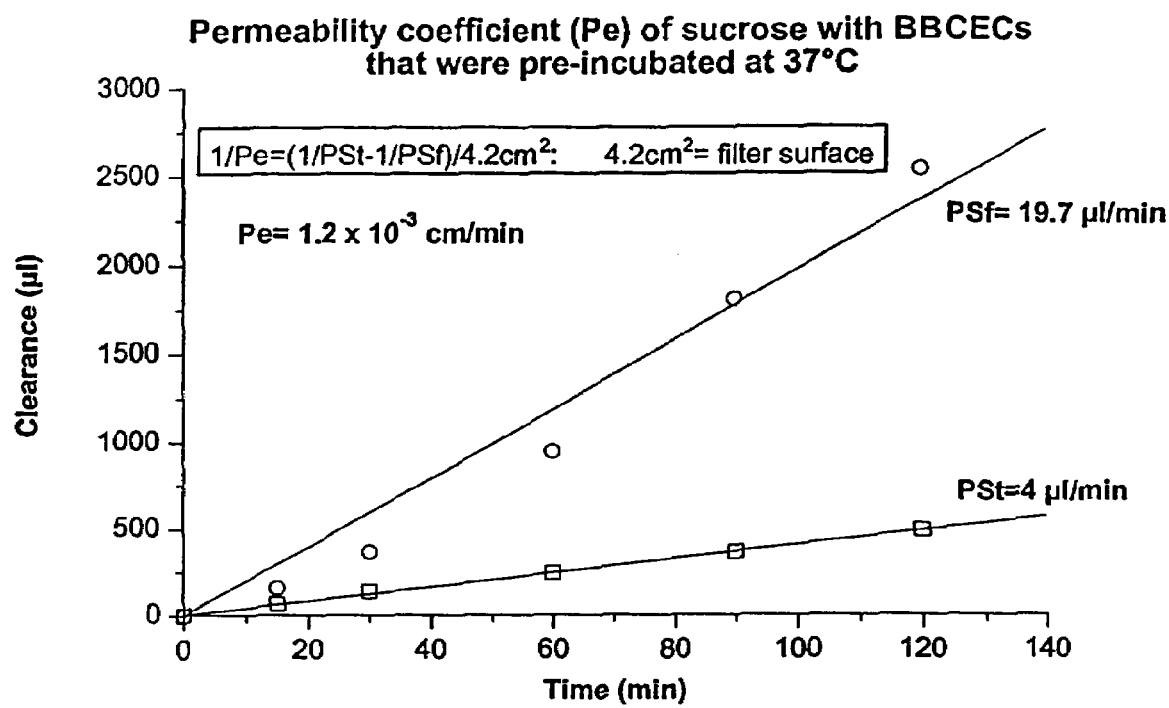
Figure 2:
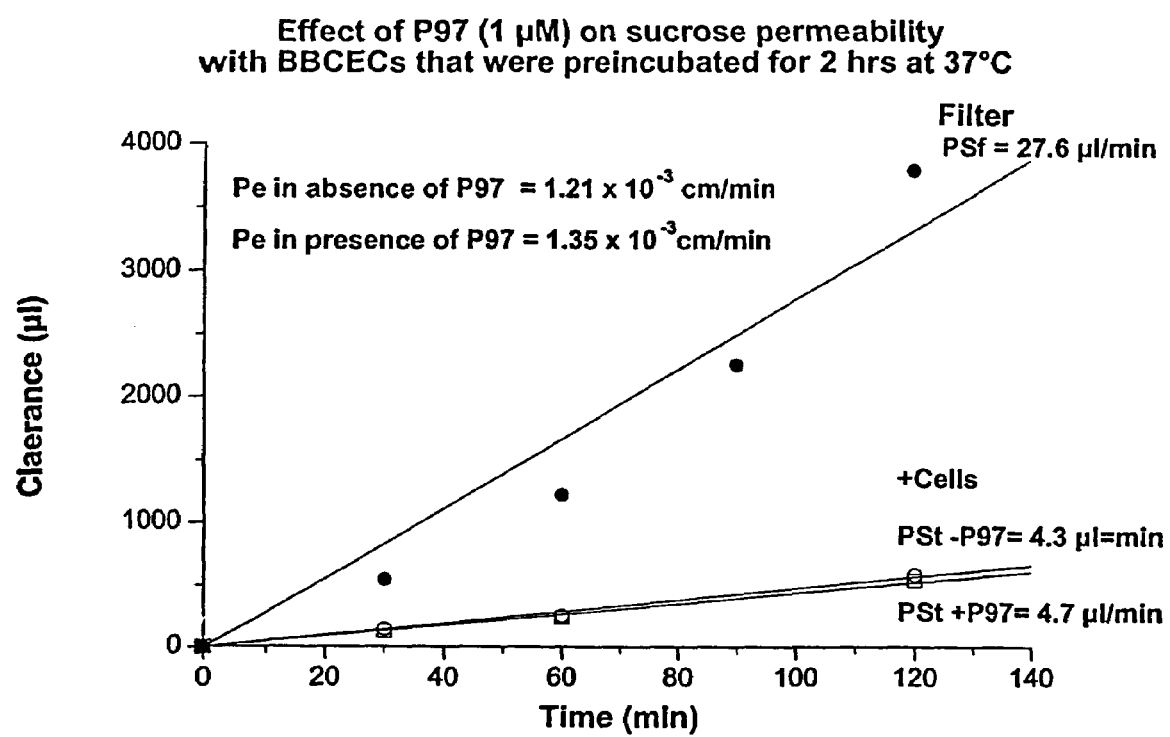

FIG. 2. Effect of p97 (1 μm) on sucrose permeability with BBCECs that were preincubated for 2 hrs at 37° C. The effect of p97 at 1 µM on sucrose permeability of the in vitro BBB model was tested. The permeability coefficient (Pe) for sucrose was calculated as previously described (Dehouck, et al., *J. Neurochem.*, 58:1790-179 (1992)) using filters coated or non-coated with BBCE cells. Briefly, coated or non-coated filters with BBCE cells were transferred to 6-well plates containing 2 ml of Ringer/Hepes per well (basolateral compartment) for 2 hrs at 37° C. In each apical (ie., luminal) chamber, the culture medium was replaced by 1 ml Ringer/Hepes containing labeled [$^{14}$C]-sucrose. At different times, inserts were placed into another well. At the end of the experiments, amounts of the radiotracers in the basolateral (ie., abluminal) compartment were measured in a liquid scintillation counter. The permeability coefficient (Pe) was calculated as described in FIG. 1.

Figure 3:
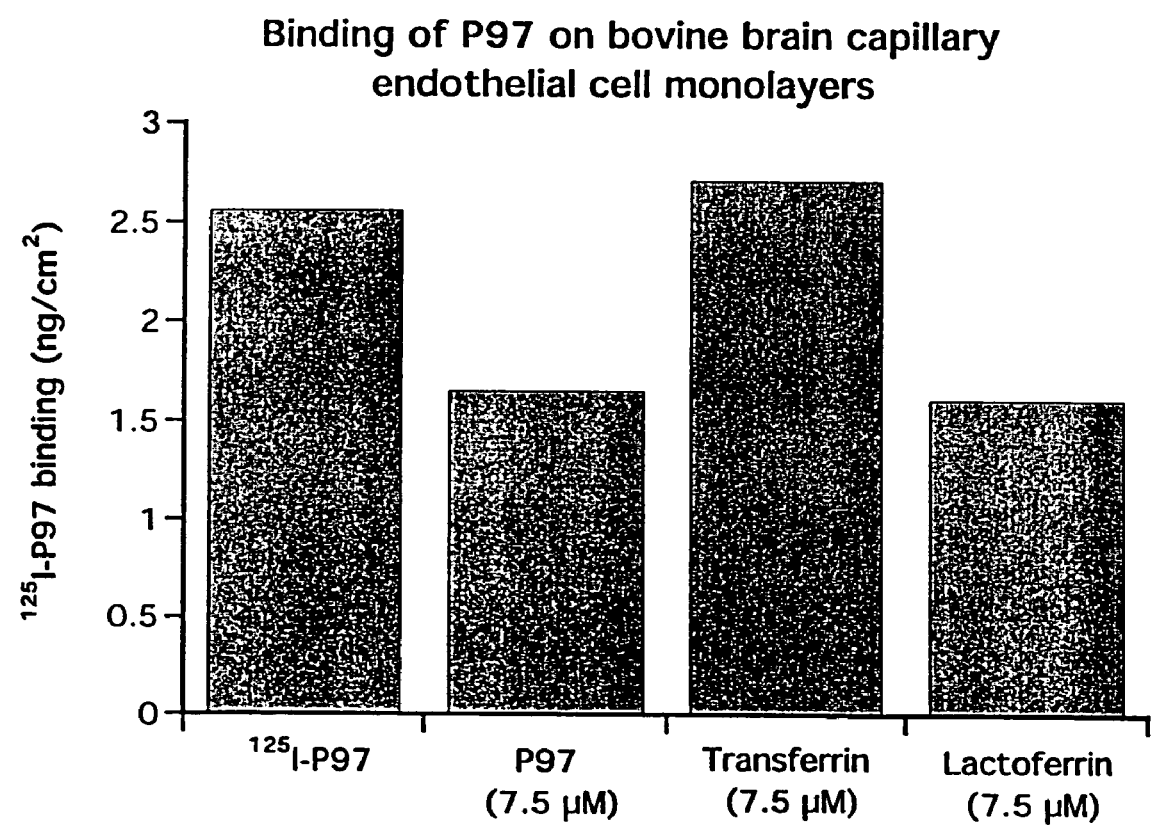

FIG. 3. Binding of p97 on bovine brain capillary endothelial cell monolayers. Binding p97 was performed with BBCECs that were pre-incubated 2 hrs in Ringer-Hepes to avoid any interference from the astrocytes. For the binding experiments, cells were incubated for 2 h at 4° C. in Ringer/Hepes in the presence of [$^{125}$I]-p97 (25 nM) and 7.5 micromolar concentrations of cold-p97, transferrin or lactoferrin, respectively. At the end of the incubation, the filters were gently washed at 4° C. three times with 4 ml of cold-PBS. Then the associated radioactivity of endothelial cells was determined by removing the membrane of the culture insert and counting it in a gamma counter.

Figure 4:
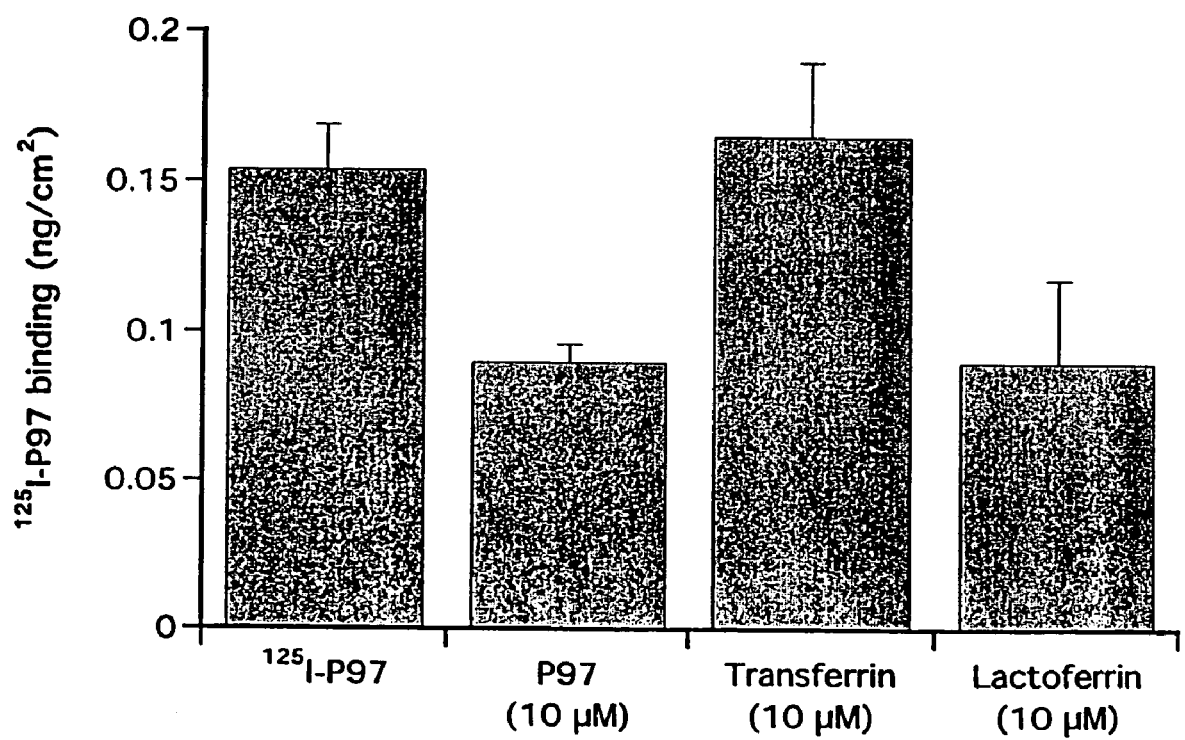

FIG. 4. Binding of p97 on rat brain endothelial cells. Binding p97 was performed with RBE4 that were pre-incubated 2 hrs in Ringer-Hepes. For the binding experiments, cells in 24-well microplates were incubated for 2 h at 4° C. in Ringer/Hepes in the presence of [$^{125}$I]-p97 (25 nM) and 10 micromolar concentrations of cold-p97, transferrin or lactoferin, respectively. At the end of the incubation, the cells were gently washed at 4° C. three times with 4 ml of cold-PBS. RBE4 cells were then lysed with Triton X-100 and the associated radioactivity of with cell lysates was determined.

Figure 5:
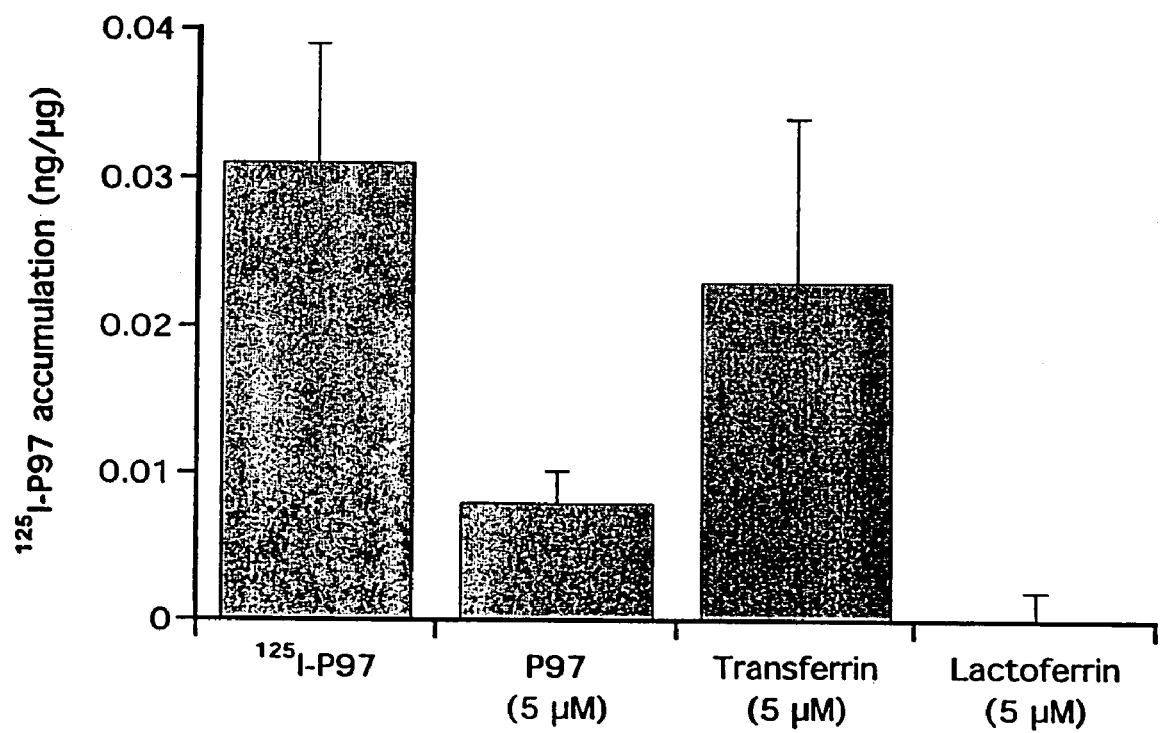

FIG. 5. Accumulation of p97 in human brain capillaries. Accumulation of [$^{125}$I]-p97 was measured at 37° C. for 1 h in isolated human brain capillaries (100 µg/assay). The incubation medium contained [$^{125}$I]-p97 and a final concentration of 100 nM p97 in Ringer/Hepes solution. The accumulation of [$^{125}$I]-p97 was performed in the presence or absence of 5 µm cold-p97, holo-transferrin or lactoferrin. After incubation, the accumulation was stopped by addition of 1 ml-cold stop solution (150 mM NaCl, 0.1% BSA and 5 mM Hepes, pH 7.5). The suspension was filtered under vacuum through a 0.45 µM pore size Millipore filter. The filter was rinsed with 8 ml of stop solution, and the radioactivity was counted. Nonspecific binding of the radioactivity to the capillaries was determined by the addition of the ice-cold stop solution to the capillaries before adding the incubation medium. This value was subtracted from accumulation values obtained following an 1 h incubation. The results were expressed as ng of [$^{125}$I]-p97 accumulated per µg of brain capillaries.

Figure 6:
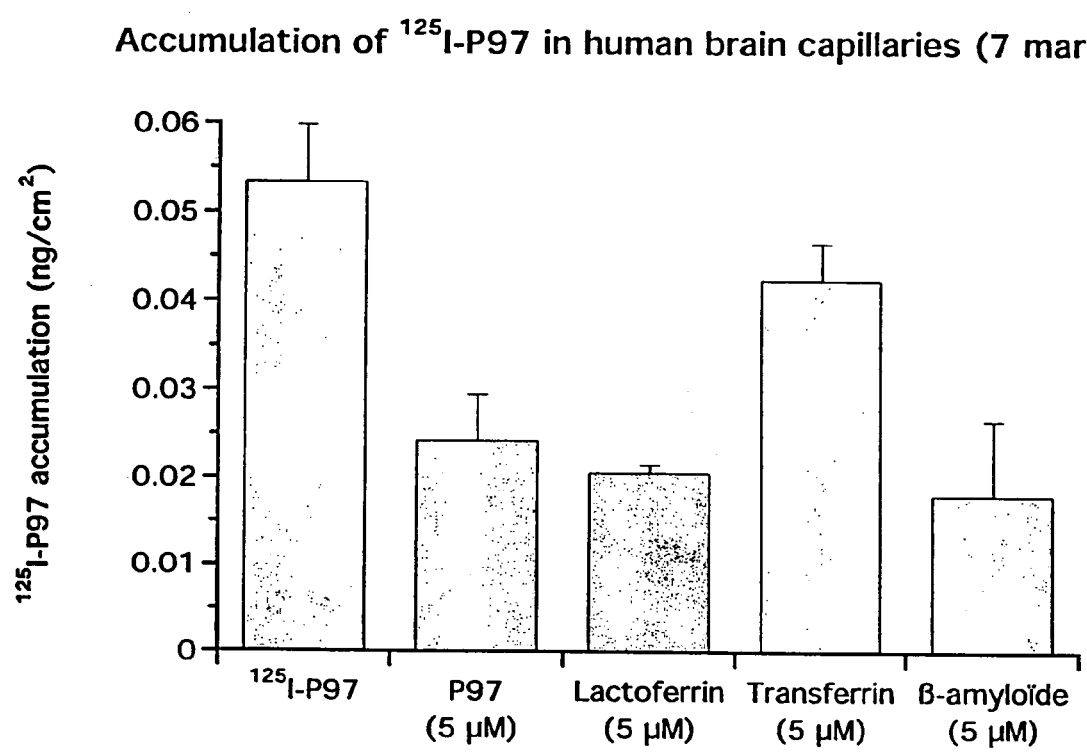

FIG. 6 is a repeat experiment, performed identically to the experiment of FIG. 5, except this time with the additional competition assay for β-amyloid peptide. Evidently, the β-amyloid peptide 1-40 competes with p97 for receptor binding, along with lactoferrin, but not with transferrin.

Figure 7:
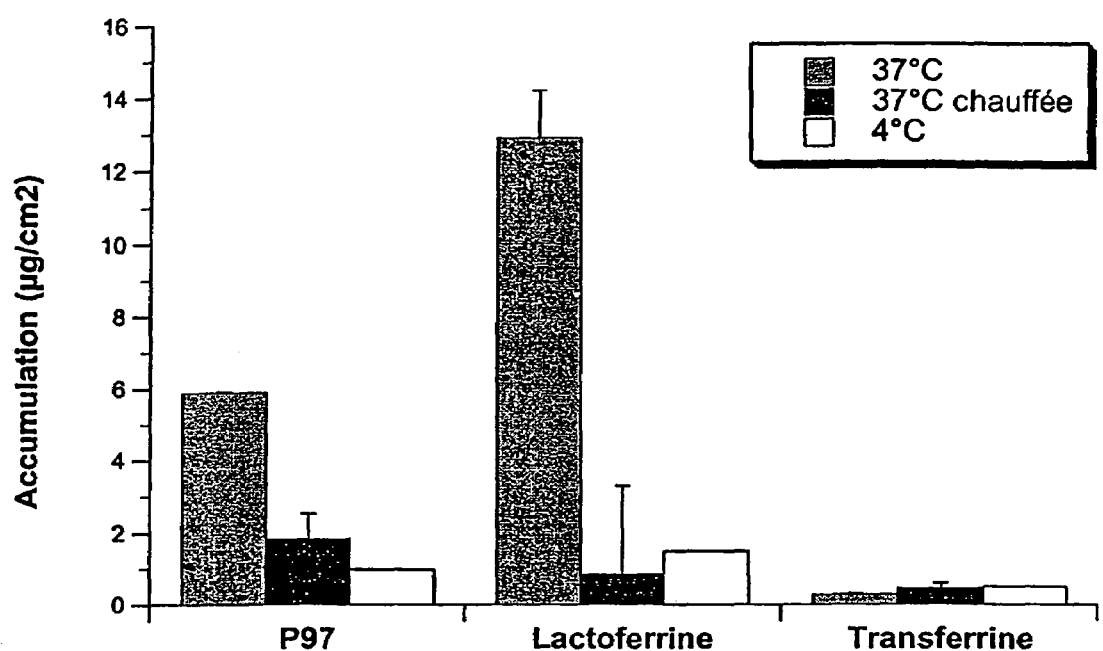

FIG. 7 illustrates the results of experiments where the ligands p97, Lf and Tf were heated or not heated prior to the binding study. In all cases, binding experiments were conducted in the transwell apparatus as described previously, with the exception that binding was conducted at either 4° C. or at 37° C. For the 37° C. trial, a separate experiment was conducted where the ligand was boiled for 30 mins then rapidly cooled prior to administration on the transwell plates.

Figure 8:
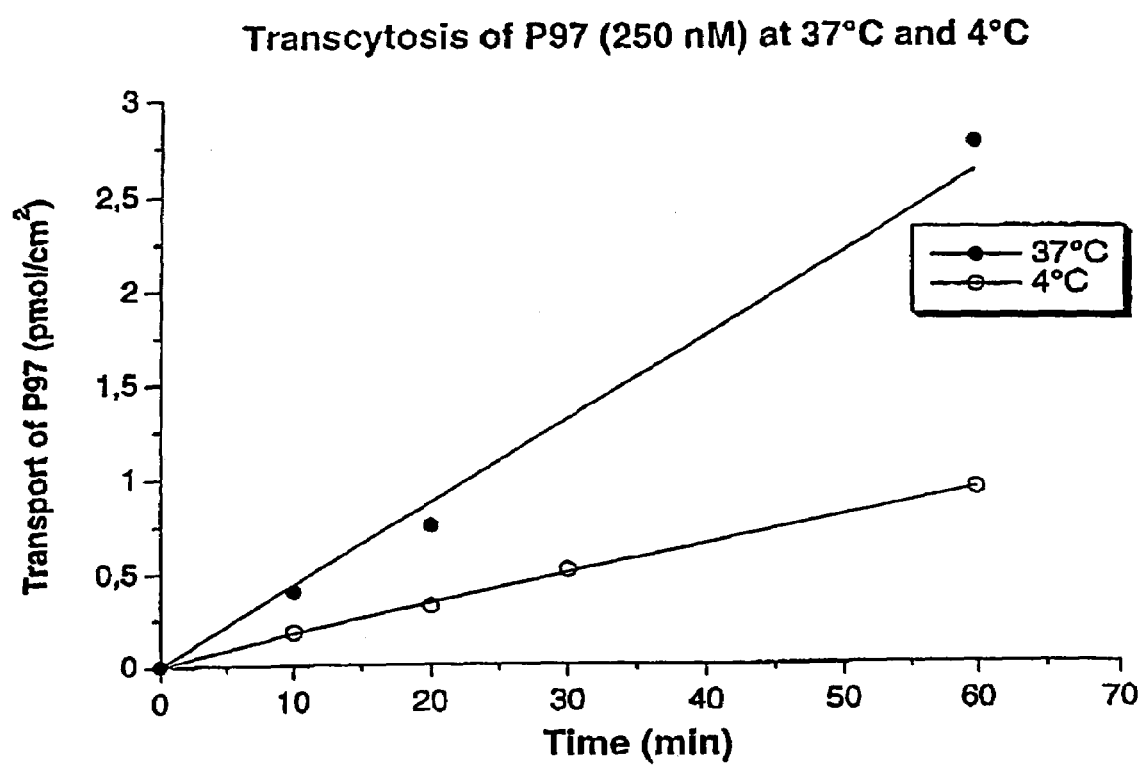

FIG. 8 demonstrates that p97 transcytosis was significantly higher at 37° C. than at 4° C. This result demonstrates that p97 is actively transported in an energy-dependent process across this blood-brain barrier model in a temperature-dependent fashion, presumably by receptor mediated uptake.

Figure 9:
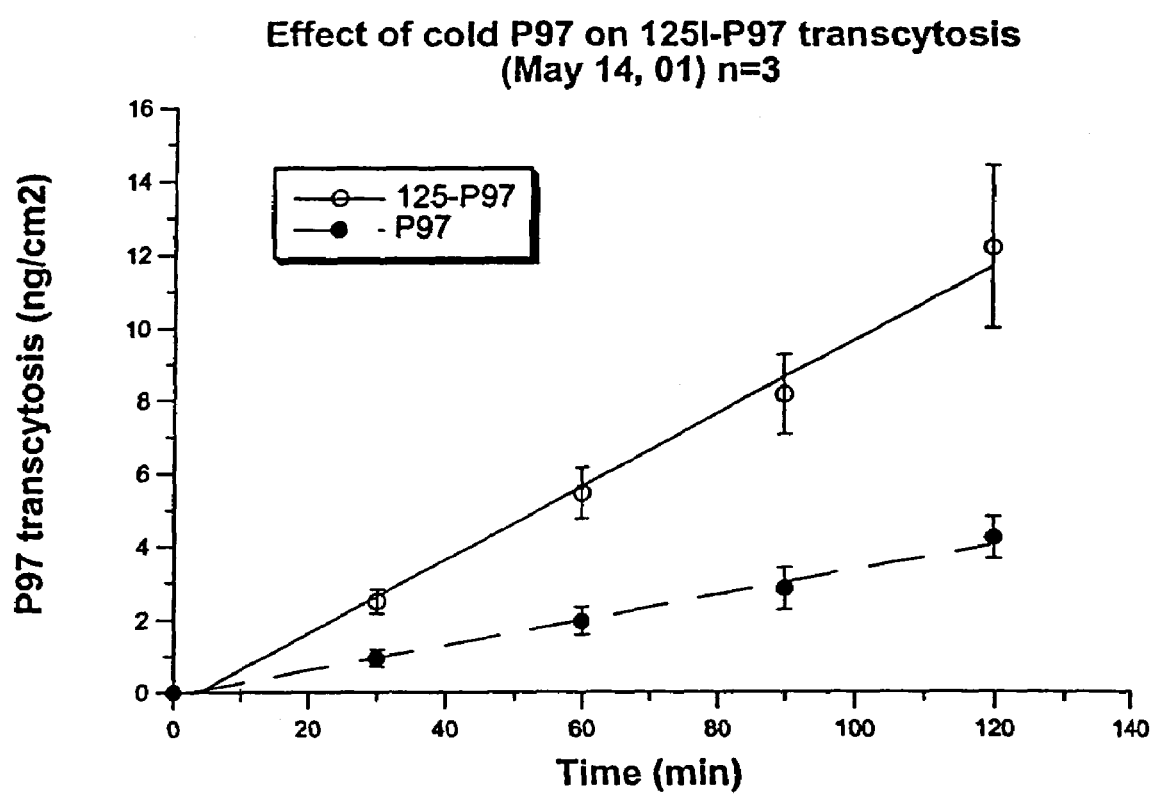

FIG. 9 confirms that transcytosis of p97 is also a saturable phenomenon, thus further implicating a specific MTf-receptor protein in this model of the blood-brain barrier. These experiments were conducted as previously described. Measurements of the amount of transcytosis were made at the time points indicated.

Figure 10A:
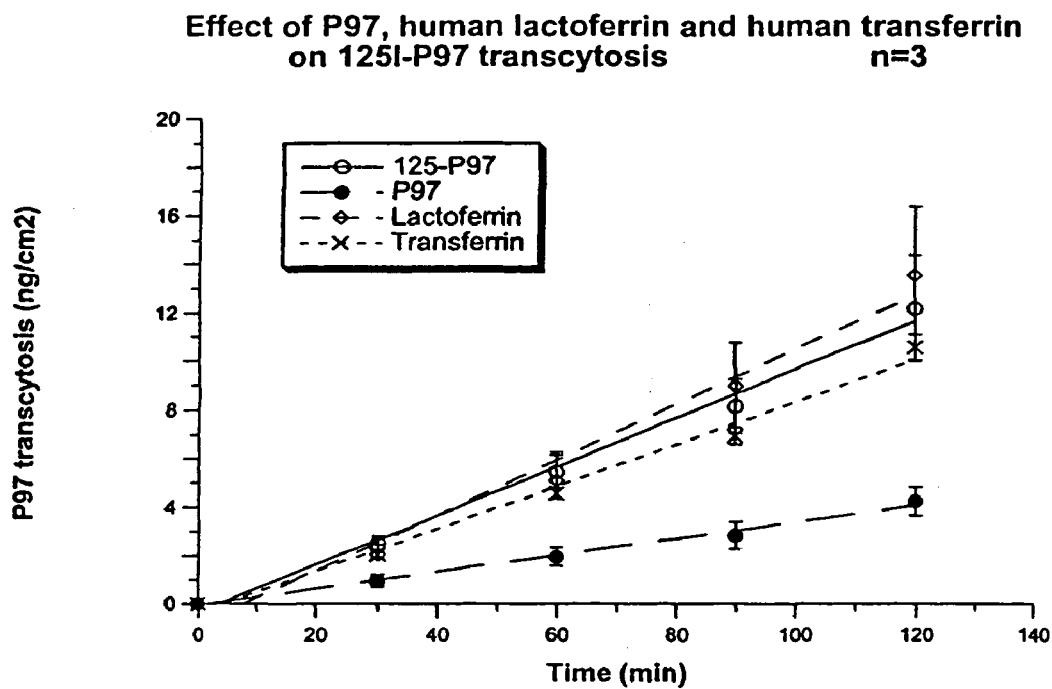
Figure 10:
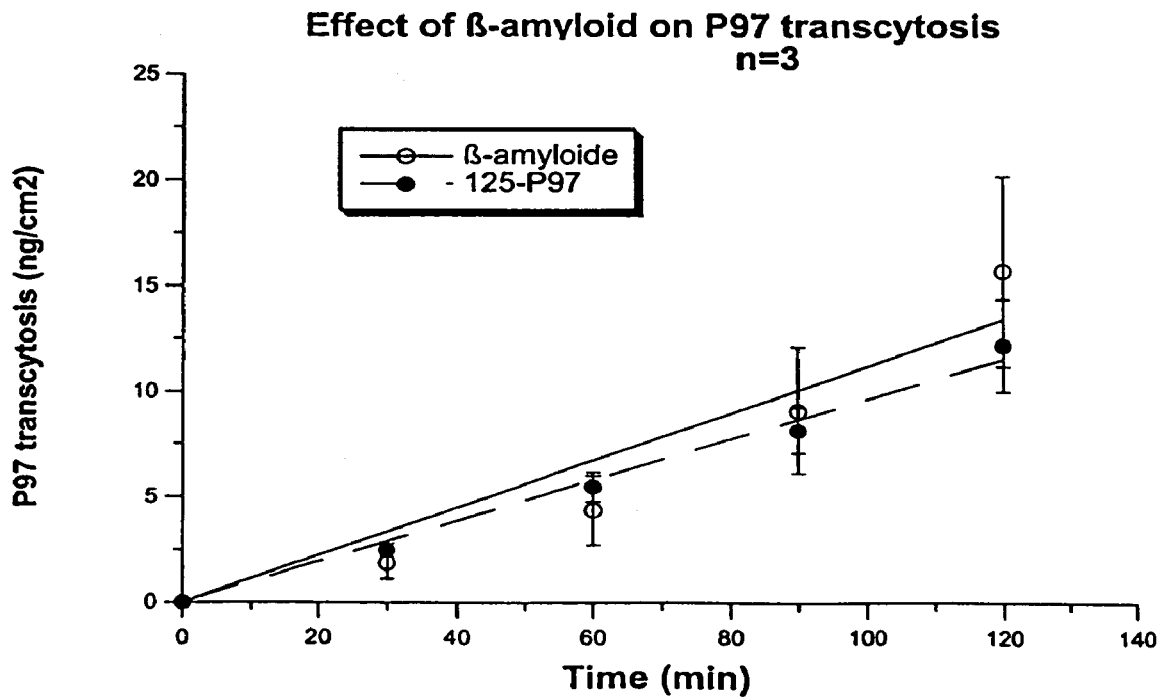
Figure 10C:
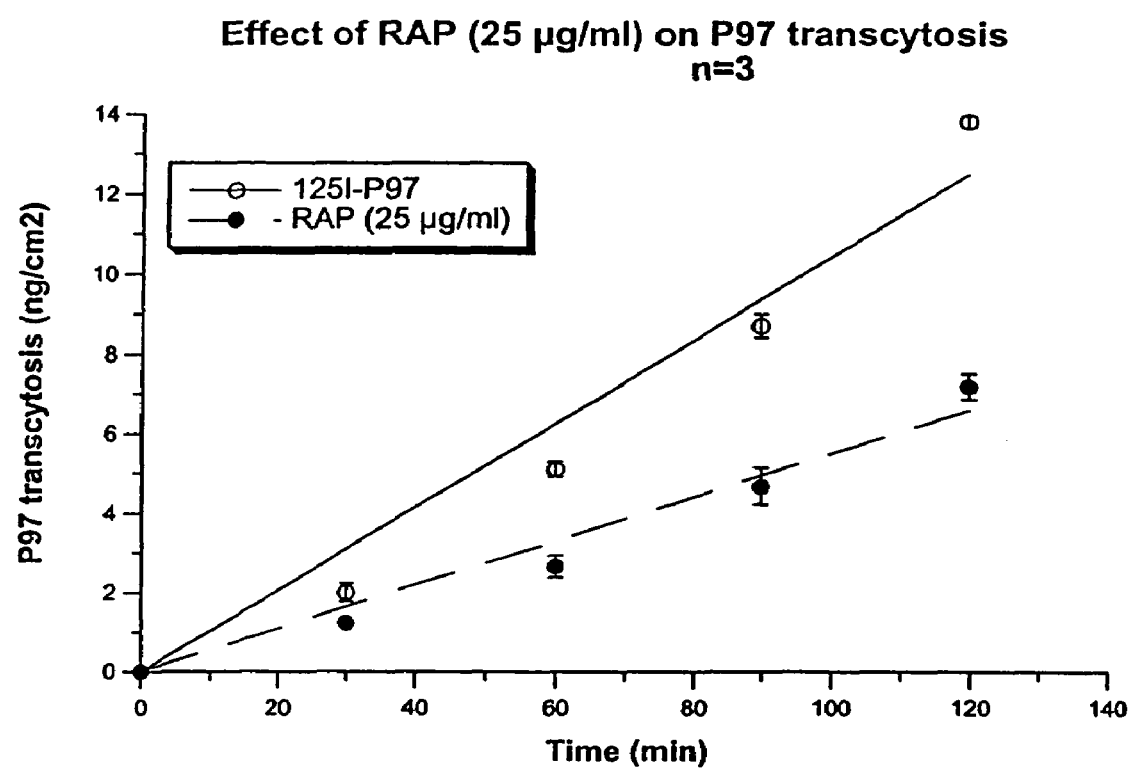

FIG. 10 assesses the ability of several agents to interfere with p97 transcytosis. FIG. 10a, transcytosis of I125-P97 was compared in the presence of cold p97 (5 micromolar), Lf(5 micromolar), and Tf(5 micromolar). FIG. 10b, β-amyloid protein (5 micromolar) also failed to slow or reduce transcytosis of labelled p97. FIG. 10c, RAP, a known poly-peptide inhibitor of the LDL-Receptor family was applied to the cells (25 micrograms/ml). RAP significantly inhibited the transcytosis of p97, thus directly implicating the LDL-receptor family, especially LRP1 as the MTf-R.

Figure 11:
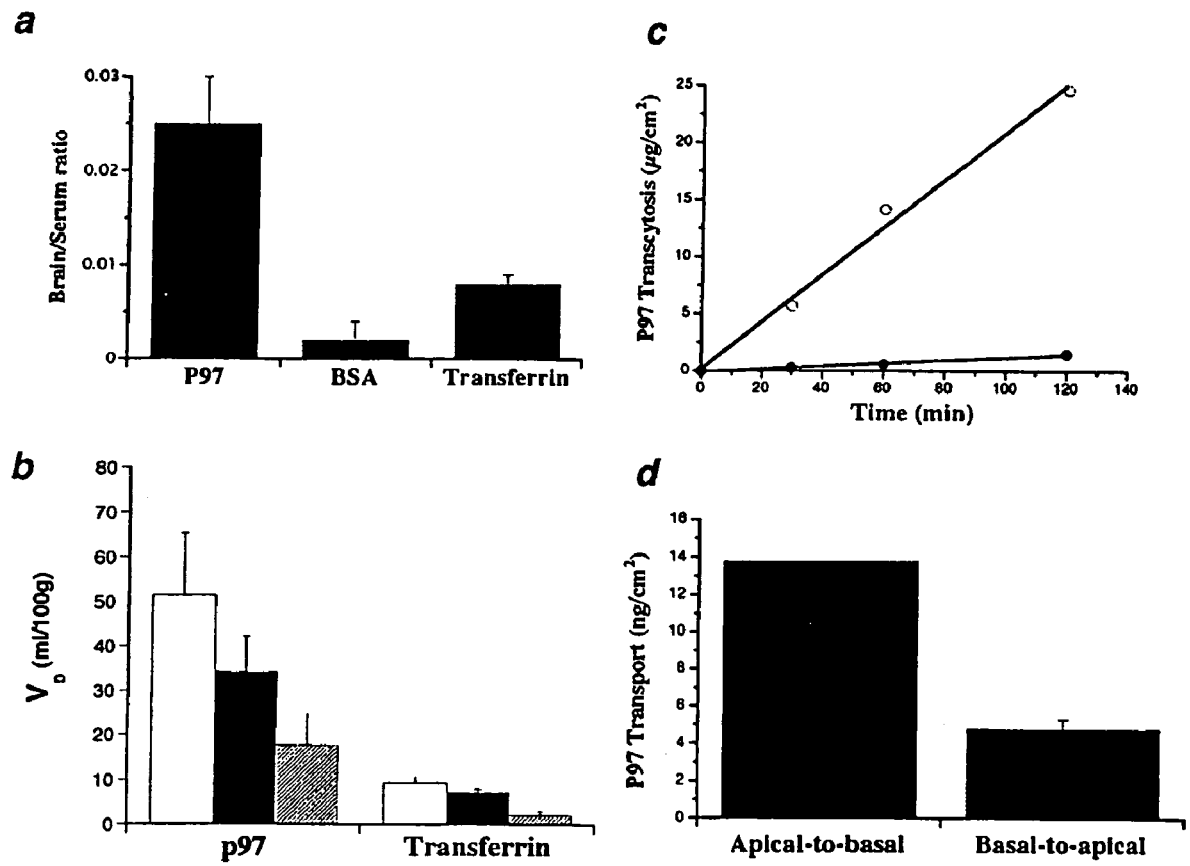

FIG. 11 examines the accumulation and transcytosis of p97. FIG. 11a, of [$^{125}$I]-p97, [$^{125}$I]-BSA and [$^{125}$I]-holo-transferrin one hour after i.v. injection. The radioactivity in brain was compared between the three compounds. (n=3); FIG. 11b. Accumulation of p97 and transferrin into the mouse brain parenchyma. In situ brain perfusion was performed with human [$^{125}$I]-p$^{97}$ or [$^{125}$I]-holo-transferrin at a final concentration of 10 nM via a catheter inserted in the right common carotid artery. The volume of distribution (vD) of [$^{125}$I]-proteins were obtained in the whole brain homogenate (white bars), in brain capillaries (solid bars) and in brain parenchyma (hatched bars) after isolation of the right hemisphere and capillary depletion. Results were obtained for p97 (n=10) and for holo-transferrin (n=6); FIG. 11c, Transcytosis of p97 across BBCEC monolayers. Transcytosis experiments were performed 37° C. (open circles) and 4° C. (closed circles) with BBCEC monolayers. [$^{125}$I]-p97 (1 mg/ml) was added to the upper side of the cell-covered filter. One representative experiment is shown (n=4); FIG. 11d, Preferential transport of p97 across the BBCEC monolayers. Apical-to-basal and basal-to-apical transport of [$^{125}$I]-p97 (25 nM) was measured for 2 hrs at 37° C. At the end of the experiment, [$^{125}$I]-p97was assessed in the lower or upper chambers of each well by TCA precipitation (n=4).

Figure 12:
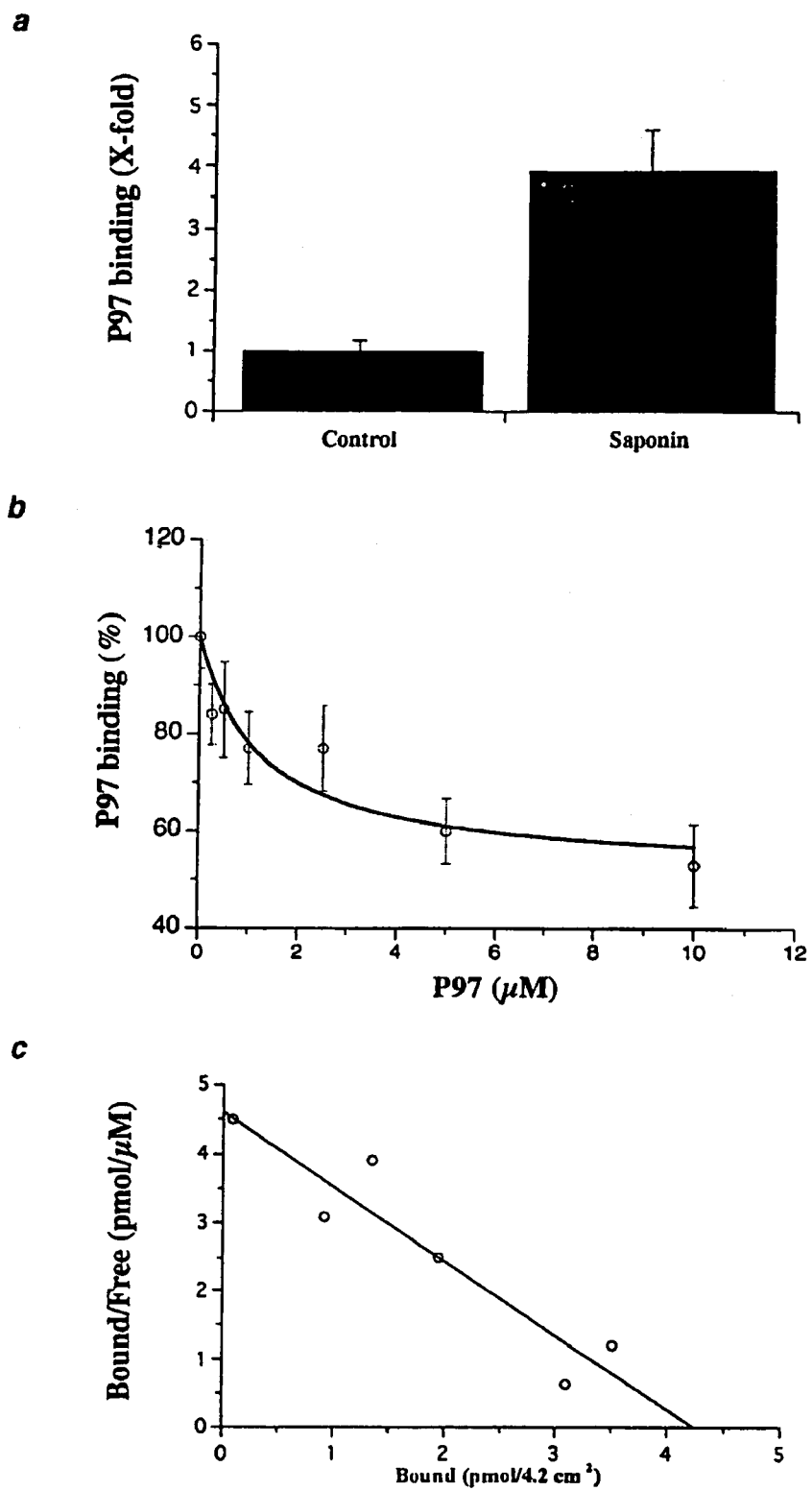

FIG. 12 illustrates the Binding of p97 to BBCE cells. FIG. 12a, p97 binding experiments were performed with BBCECs that were either pre-incubated in Ringer-Hepes solution or pre-treated with saponin. BBCECs were then incubated for 2 hrs at 4° C. with [$^{125}$I]-p97 (25 nM). At the end of the incubation, the filters were gently washed with cold PBS and then the radioactivity associated with the ECs was quantified; FIG. 12b. The binding of [$^{125}$I]-p97 was also performed with increasing concentrations of unlabelled p97 following saponin treatment. The results were expressed as the percentage of the [$^{125}$I]-p97 binding measured in the absence of unlabelled p97; FIG. 12c, The results were also transformed with a Scatchard plot and expressed as the ratio of bound p97/free p97 as a function of the bound p97 (n=5).

Figure 13:
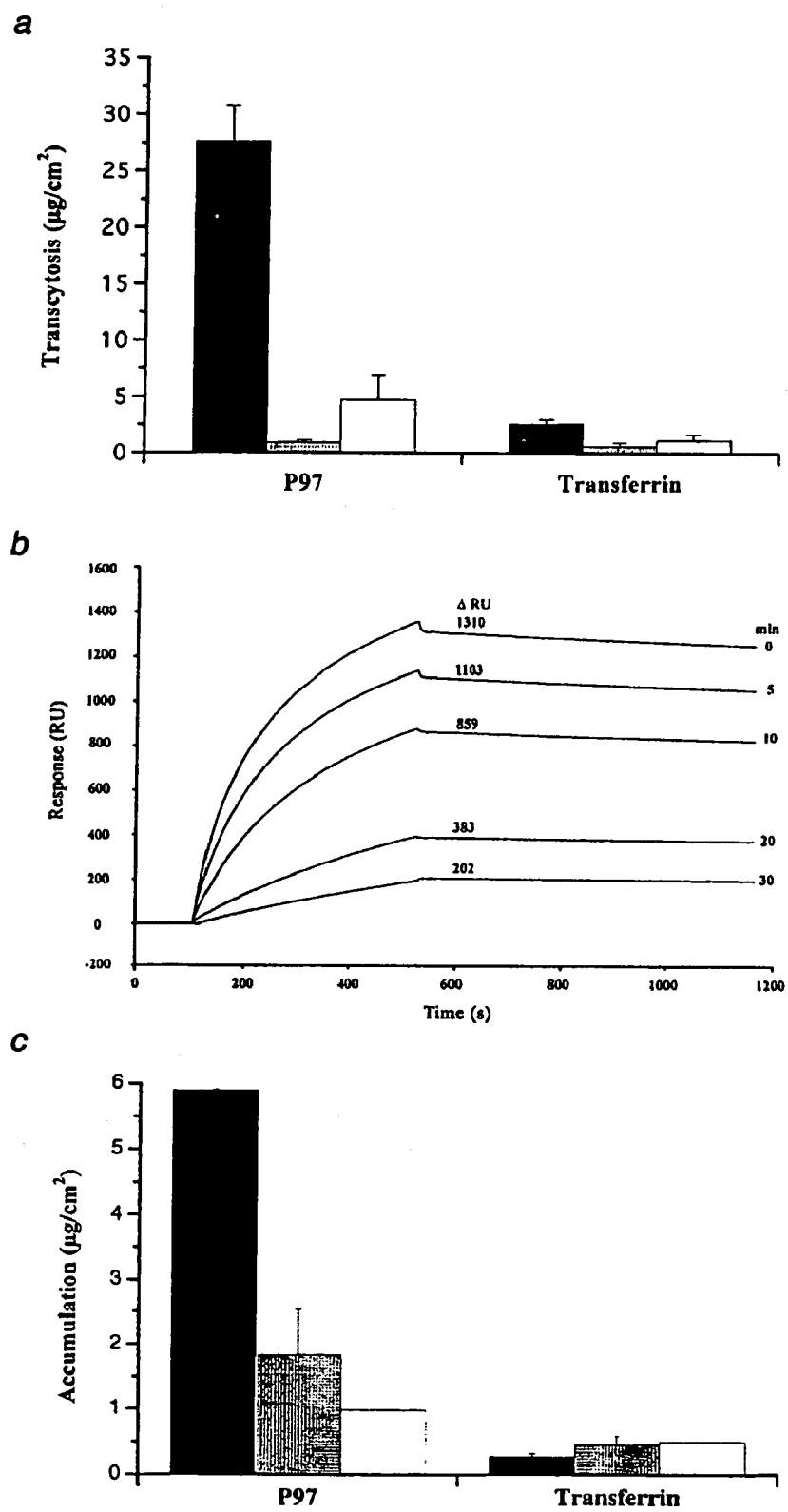

FIG. 13 illustrates the transcytosis and accumulation of p97 and transferrin in BBCEC monolayers. FIG. 13a, Transcytosis experiments were performed at 37° C. (solid bars) or 4° C. (white bars). [$^{125}$I]-p97 or bovine [$^{125}$I]-holo-transferrin (1 mg/ml) was added to the uper side of the cell-covered filter. At the end of the experiment, radiolabelled proteins were measured in the lower chamber of each well by TCA precipitation (n=4). Controls were also performed at 37° C. with denatured [$^{125}$I]-p97 or bovine [$^{125}$I]-holo-transferrin boiled for 30 min (grey bars) (n=2); FIG. 13b, Biospecific interaction analysis was performed with native or boiled p97 for the indicated times. MAb L235 (5 µg) was immobilized on a sensor chip (SM5) using standard procedures incorporating NHS, EDC and ethanolamine. Native and boiled p97 (5 to 30 min) diluted at 1 mg/ml in Ringer/Hepes was cooled and injected into the BIAcore. The surface plasmon resonance response obtained for native p97 and boiled p97 was plotted (in relative units (RU)) as a function of time; FIG. 13c, The accumulation of both proteins into BBEC cells were also measured. Briefly, after incubation at 37° C. (solid bars) or 4° C. (white bars) with either [$^{125}$I]-protein, cells were washed four times with cold PBS. Accumulation of both denatured proteins (grey bars) was also measured at 37° C. Filters were then removed, and the radioactivity associated with the cells was quantified (n=3).

Figure 14:
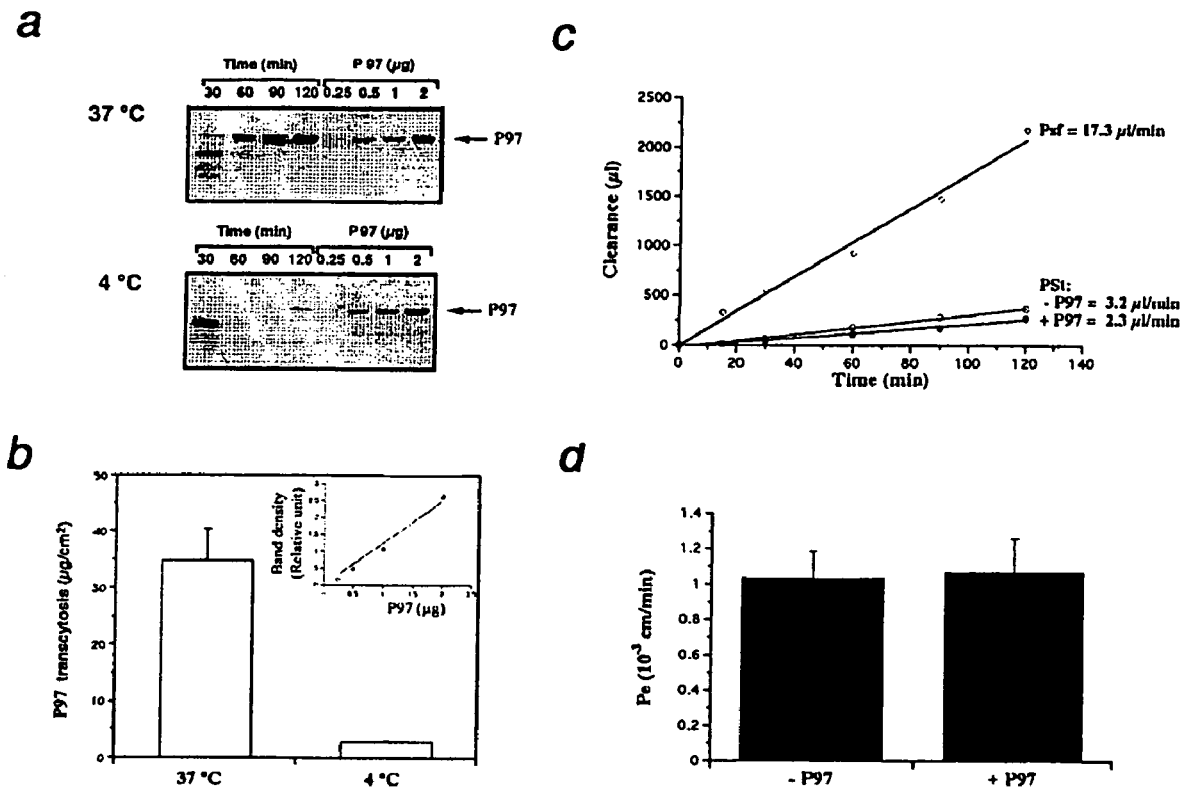

FIG. 14 illustrates the stability of p97 and integrity of the BBCEC monolayers following p97 transcytosis. FIG. 14a, Transcytosis experiments were performed at 37° C. and 4° C. by adding p97 (1 mg/ml) to the upper compartment. At the end of the experiment, 50 µl from each lower chamber was used for SDS-polyacrylamide gel electrophoresis. After electrophoresis, the gels were stained with Coomassie Blue. A standard curve was also made with known amounts of recombinant p97 (0-2 µg); FIG. 14b, The gels were dried and scanned to quantify the amount of intact p97 that crossed the BBCEC monolayers at 37° C. and 4° C. (n=3); FIG. 14c, Effect of p97 on sucrose permeability of BBCE cell monolayers co-cultured with astrocytes. The passage of [$_{14}$C]-sucrose was measured with filters (à) or with filters coated with BBCE cells in the absence (open circles) or in the presence of p97 (up to 1 mg/ml (closed circles). One representative experiment is shown. The results were plotted as the sucrose clearance (µl) as a function of time (min); FIG. 14d, The sucrose permeability coefficient (Pe) was determined in the presence (+p97) or in the absence (−p97) of p97, and was calculated as described in the Examples (n=3).

Figure 15:
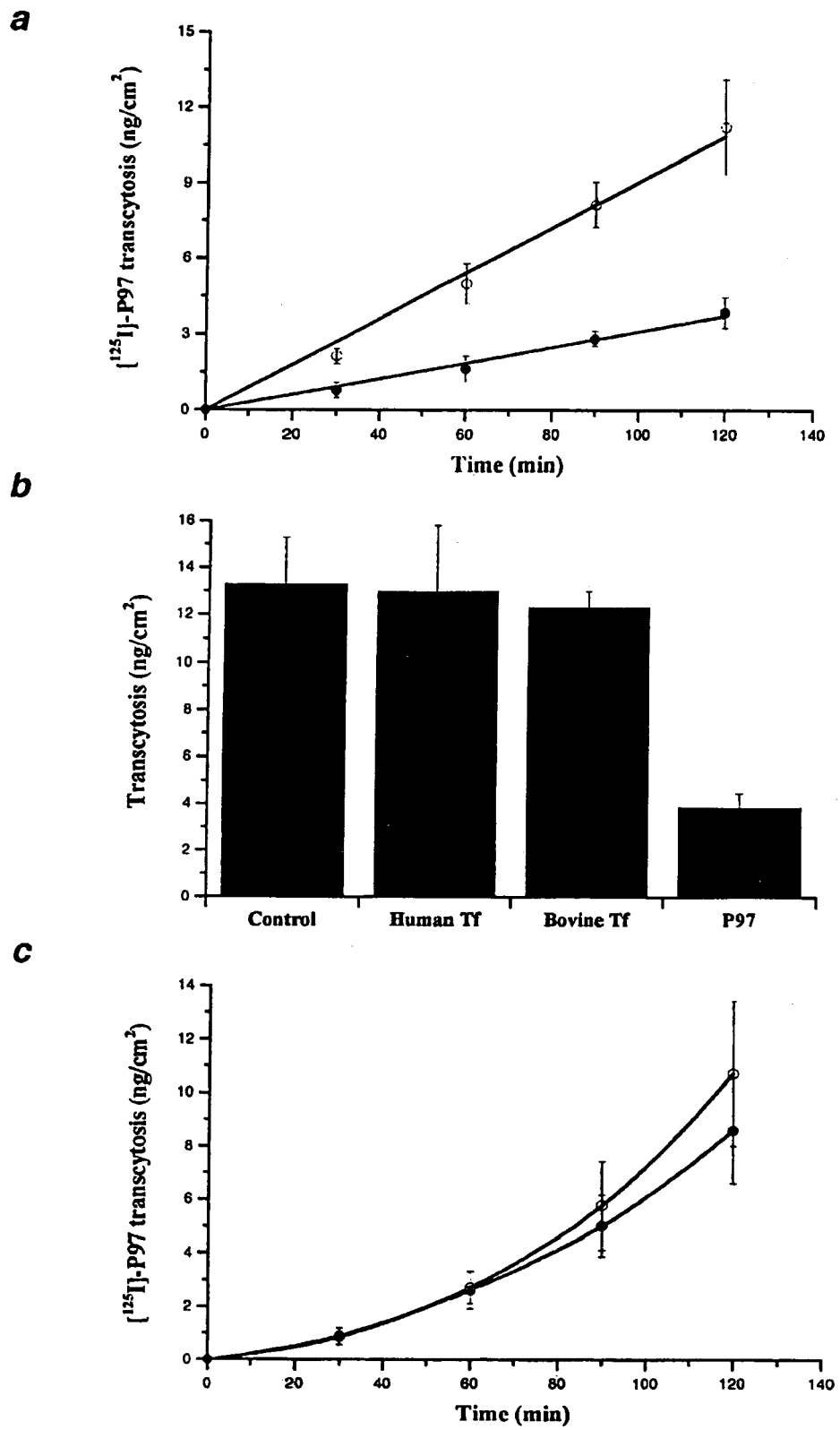

FIG. 15 shows the inhibition of [$^{125}$I]-p97 transcytosis in BBCEC monolayers. FIG. 15a, Transport of [$^{125}$I]-p97 (25 nM) from the apical to the basolateral side of ECs was measured in the absence (open circles) or in the presence (closed circles) of a 200-fold molar excess of unlabelled p97; FIG. 15b, The effects of a 200-fold molar excess of either human or bovine transferrin (Tf) and p97 were also evaluated on [$^{125}$I]-p97 transcytosis across BBCEC monolayers (n=5); FIG. 15c, Transcytosis of [$^{125}$I]-p97 (25 nM) was also measured in the presence of mouse IgGs (open circles) or mAb OX-26 (closed circles) at a concentration of 5 µg/ml (n=3).

Figure 16:
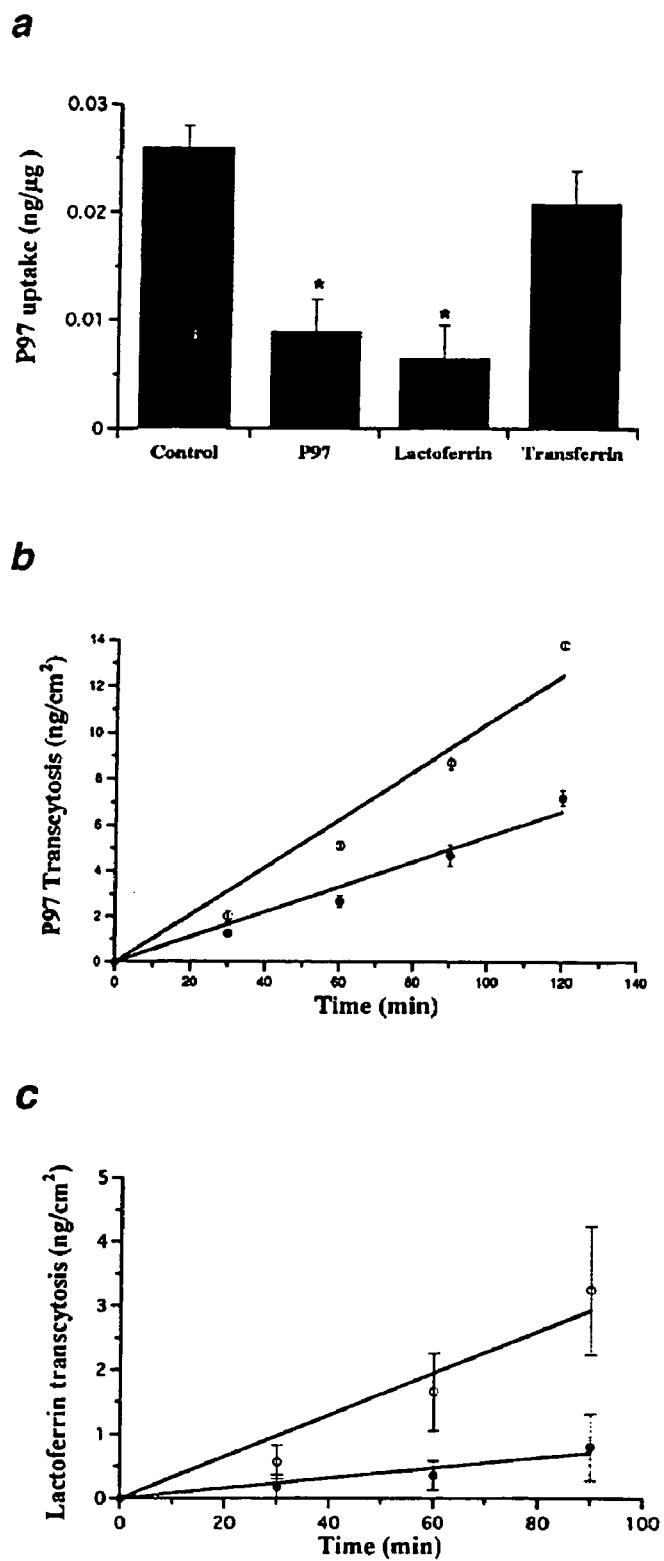

FIG. 16 illustrates the identification of a p97 receptor according to ligand specificity. FIG. 16a, Uptake of [$^{125}$I]-p97 into human brain capillaries. The uptake of [$^{125}$I]-p97 at 100 nM (control) into isolated human brain capillaries was measured for 1 h at 37° C. in the presence of a 50-fold molar excess of unlabelled p97, human holo-transferrin or human lactoferrin. (*P<0.5 Student's t-test (n=5); FIG. 16b, Effect of RAP on [$^{125}$I]-p97 transcytosis across BBCEC monolayers. Apical-to-basal transport of [$^{125}$I]-p97 was measured in the presence (closed circles) or absence (open circles) of RAP (25 µg/ml) (n=5); FIG. 16c, Inhibition of bovine [$^{125}$I]-lactoferrin transport by p97. Transcytosis of bovine [$^{125}$I]-lactoferrin (50 nM) was measured in the presence (closed circles) or absence (open circles) of unlabelled p97 (5 µM) at 37° C. (n−3).

Figure 17:
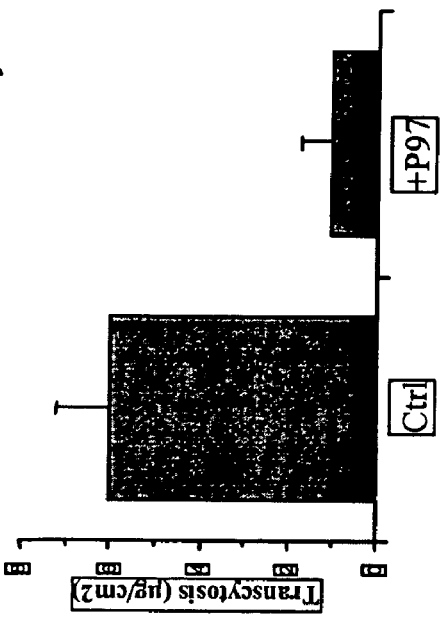
Figure 17:
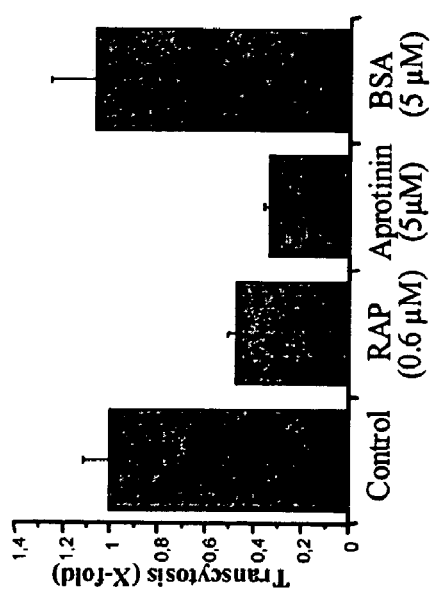

FIG. 17. Examination of the role of LRP on p97 transcytosis. FIG. 17A. Apical-to-basal transport of [$^{125}$I]-p97 was measured for 2 h at 37° C. in the absence (Control) or presence of RAP (0.6 µM), aprotinin (5µM) or BSA (5 µM). Results represent means±SD (n=5 for RAP; n=3 for aprotinin and BSA). [$^{125}$I]-p97 was assessed in the lower chamber of each well by TCA precipitation. FIG. 17B. Inhibition of bovine [$^{125}$I]-lactoferrin transport by p97. Transcytosis of bovine [$^{125}$I]-lactoferrin (50 nM) was measured in the presence or absence of unlabelled p97 (5 µM) at 37° C. for 2 hrs. Bovine [$^{125}$I]-lactoferrin was assessed in the lower or upper chambers of each well by TCA precipitation. Results represent means±SD (n=6). Some ligands for LRP and megalin are presented in FIG. 17C.

Figure 18:
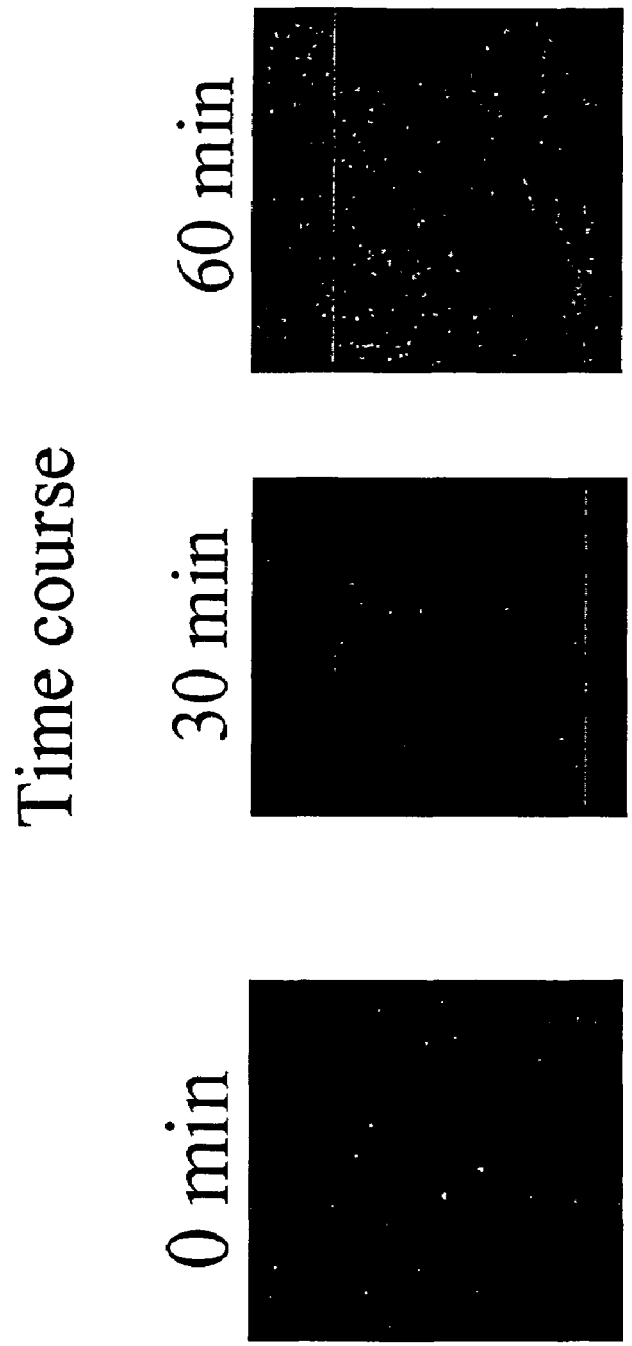

FIG. 18 illustrates the time-course of the uptake of p97 in BBCE and accumulation in early endosome.

Figure 19:
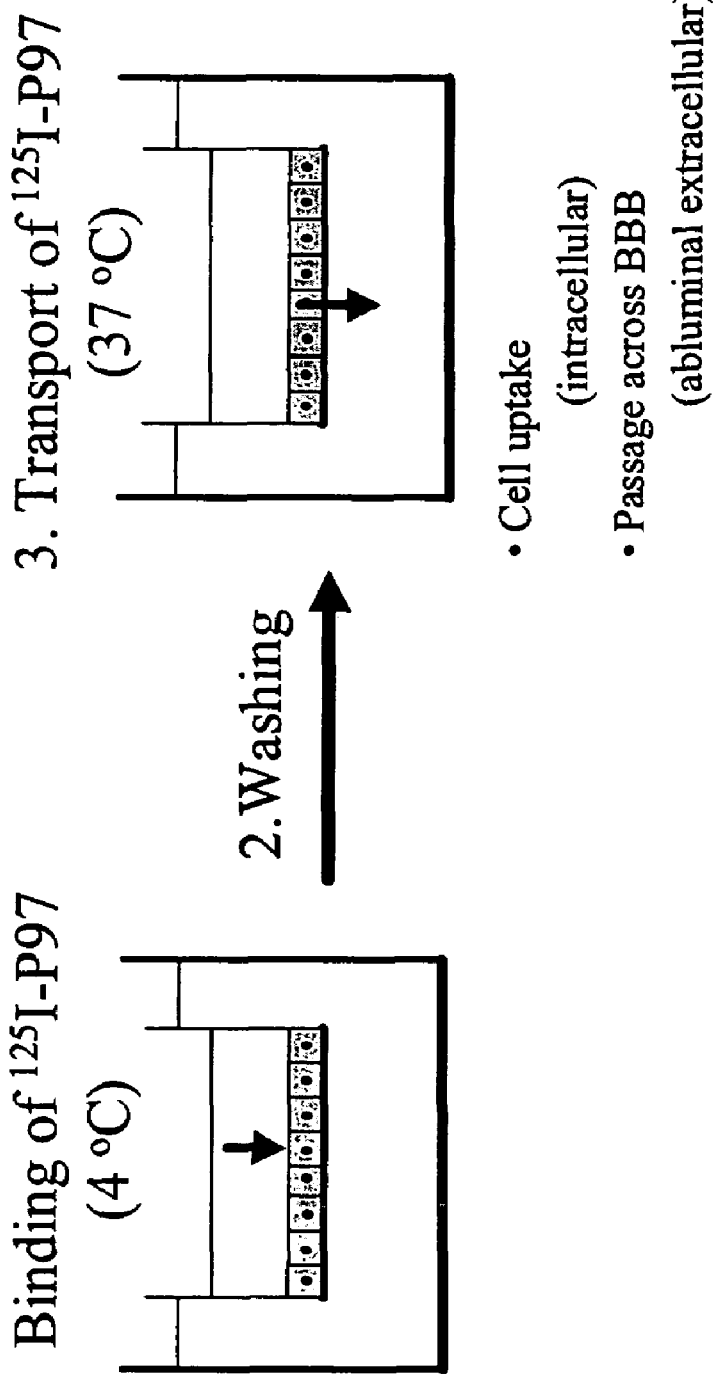

FIG. 19 is a schematic of how the p97 transport rate across the blood brain barrier of the model is determined.

Figure 20:
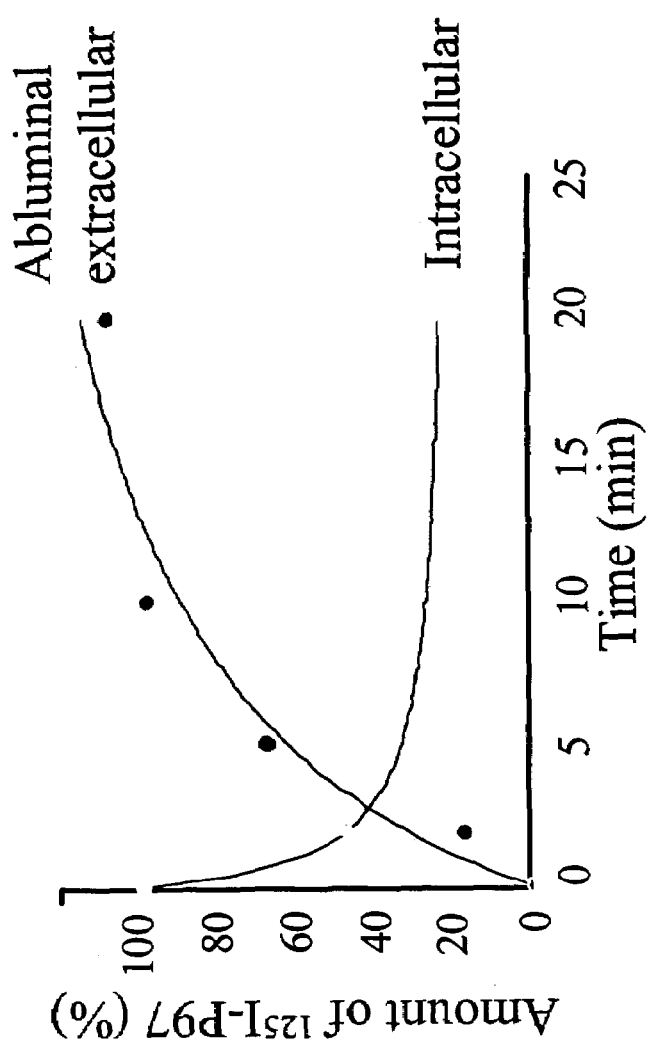

FIG. 20 presents the results of measuring the rate of internalization and transcytosis of p97 in the blood brain barrier model.

FIG. 21 depicts the transcellular co-localization of p97 and clathrin turning transcytosis.

Figure 22:
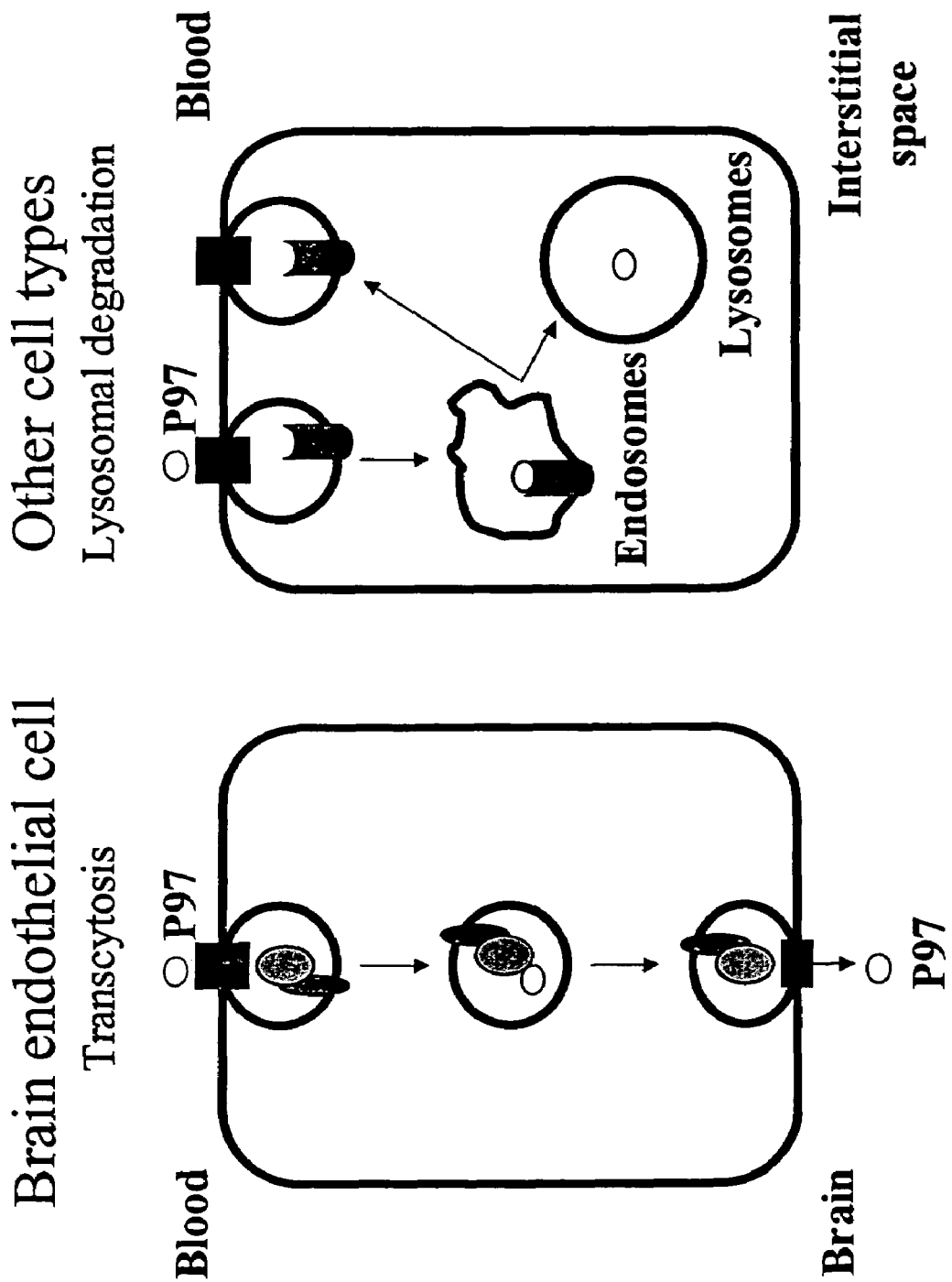

FIG. 22 is a schematic drawing of two of several pathways possible following endocytosis of a p97 compound or conjugate: transcytosis and lysosomal delivery.

Figure 23:
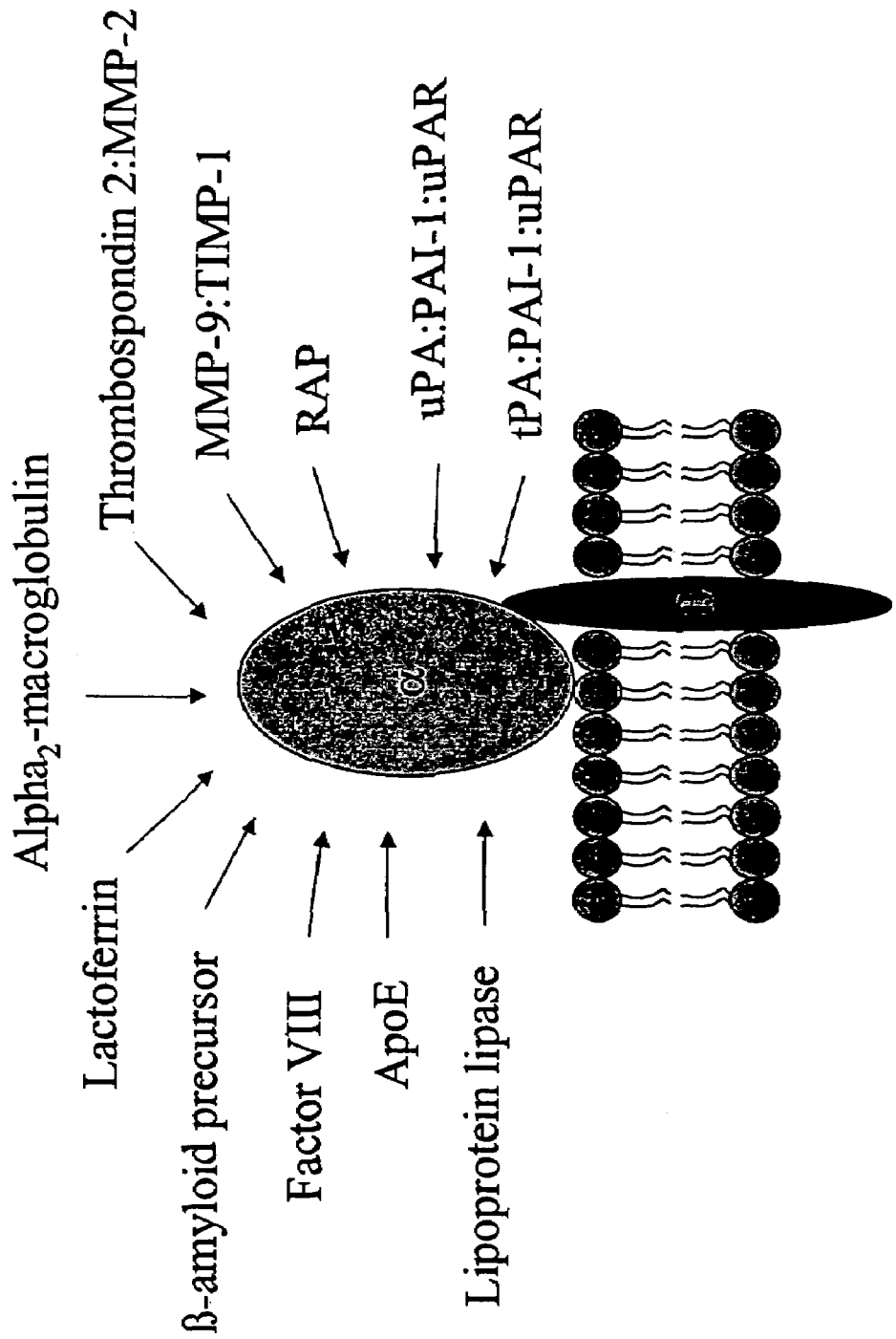

FIG. 23 is a schematic drawing of the LRP receptor associated with a cell membrane and a number of the ligands of such LRP receptors.

Figure 24:
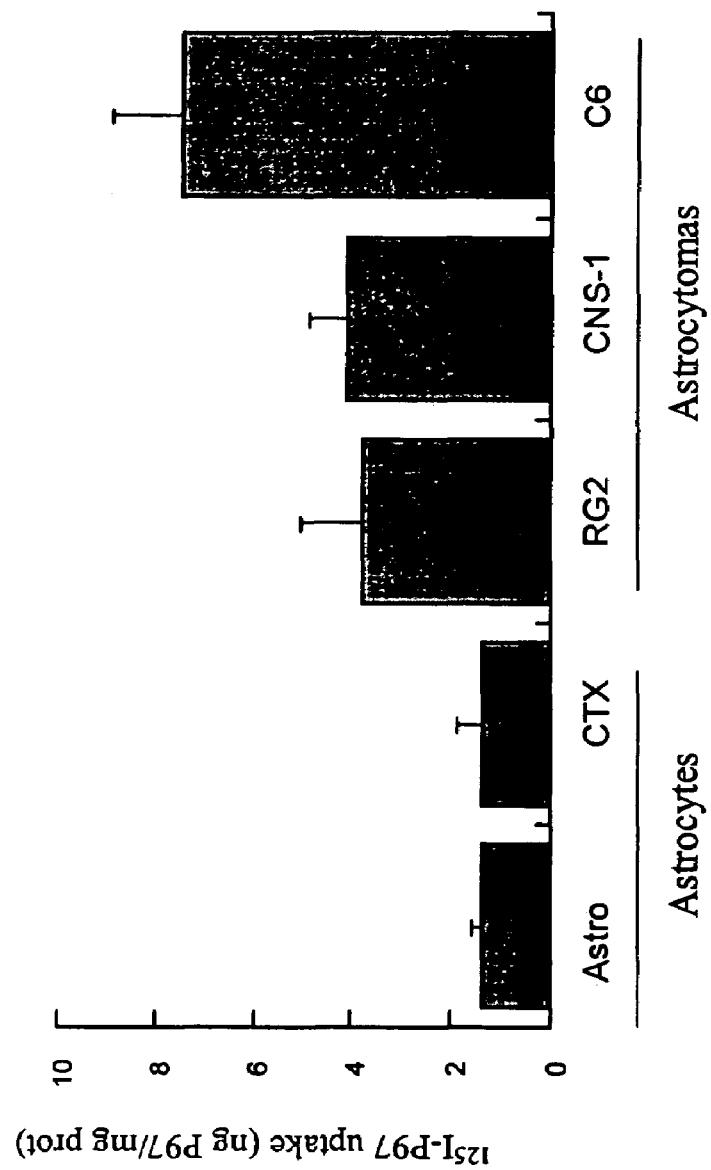

FIG. 24. Uptake of p97 in rat astrocytes and astrocytoma cells. Cells were grown in monolayer in six-multiwell microplates at 37° C. under 5% CO2. Uptake of [$^{125}$I]-p97 was measured at 37° C. for 2 h in astrocytes and astrocytomas. The incubation medium contained [$^{125}$I]-p97 and a final concentration of 50 nM p97 in Ringer/Hepes solution. After incubation, the cell monolayer was washed three times with cold Ringer/Hepes solution. Triton X-100 0.1% was added and the [$^{125}$I]-p97 uptake was assessed in the Triton X-100 soluble fraction by TCA precipitation. Results represent means±SD (n=3, Astro; n=6, CTX and RG2; n=9, C6).

Figure 25:
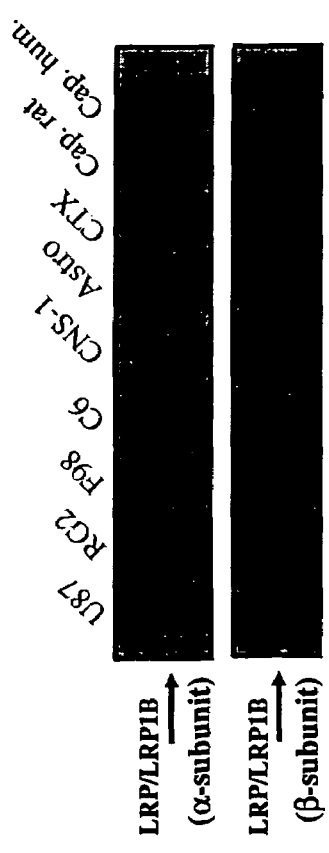
Figure 25:
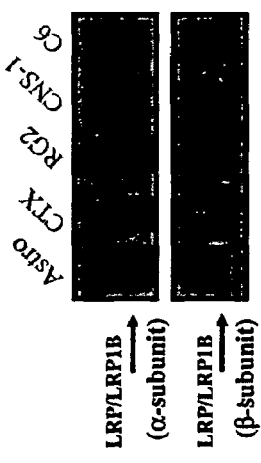

FIG. 25. Immunodetection of LRP/LRP 1B. Cells lysates (25 (g) were subjected to SDS-PAGE under non-reducing conditions and electroblotted onto PVDF membranes. LRP/LRP1B was immunodetected using a rabbit polyclonal antibody raised against the low density lipoprotein receptor-related protein as previously described (Bu et al., J. Biol. Chem. 17:13002-13009, 1993). (n=1)

Figure 26:
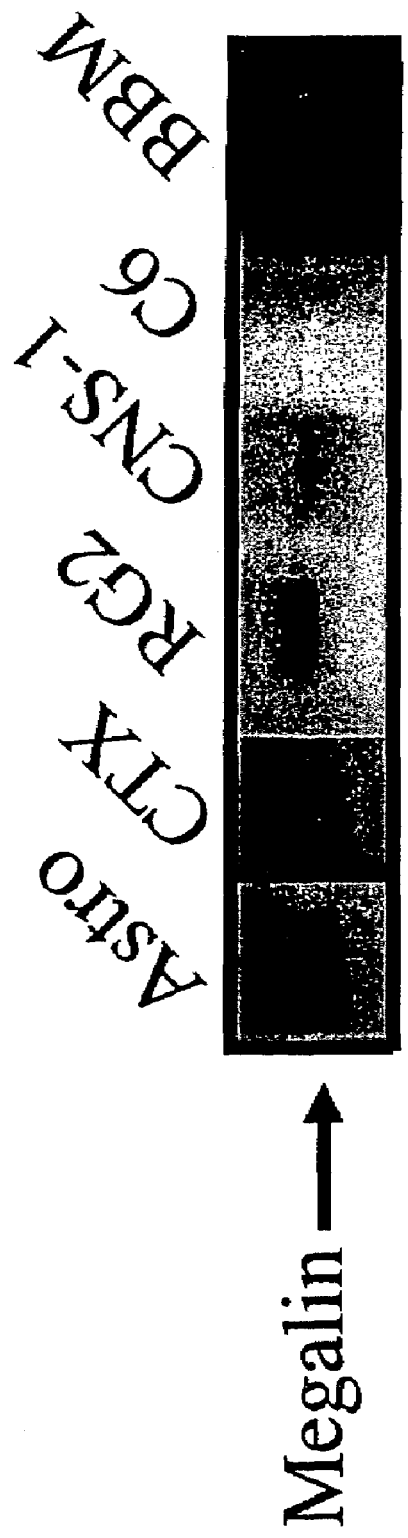

FIG. 26. Immunodetection of megalin. Cells lysates were subjected to SDS-PAGE under non-reducing conditions and electroblotted onto PVDF membranes. Megalin was immunodetected using a mouse monoclonal antibody diluted 1/2500 in TBS-Tween 0.1%, 3% BSA and 0.01% NaN3. (n=1)

Figure 27:
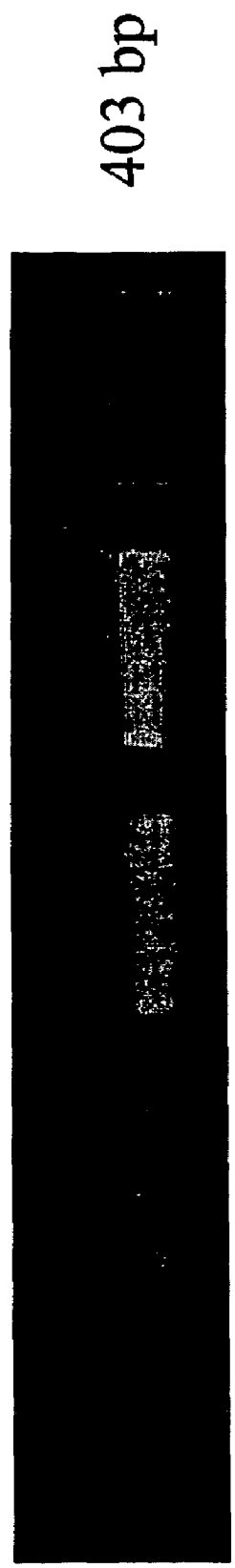

FIG. 27. mRNA extraction and RT-PCR of LRP1B. For RNA extraction, cells were grown in 75 cm$^2$ plastic tissue culture flasks at 37° C. under 5% CO2 with optimal culture medium to 80-90% confluence. Total RNA from each cell line was extracted as described in the Examples. The amplified PCR products were electrophoresed on a 2% agarose gel and visualized under ultraviolet light. (n=1).

Figure 28:
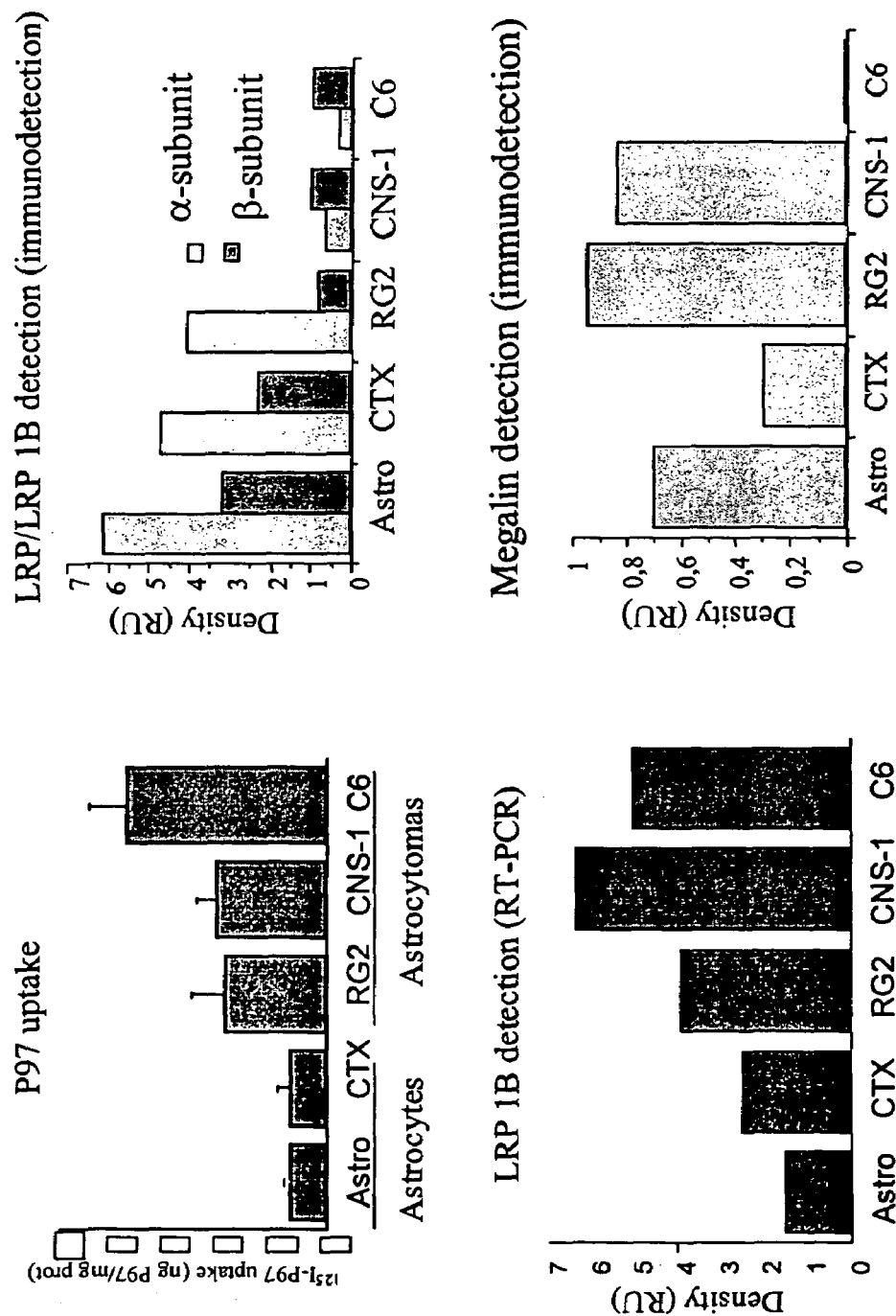

FIG. 28 presents some results of experiments correlating p97 uptake with LRP1B expression.

Figure 29:
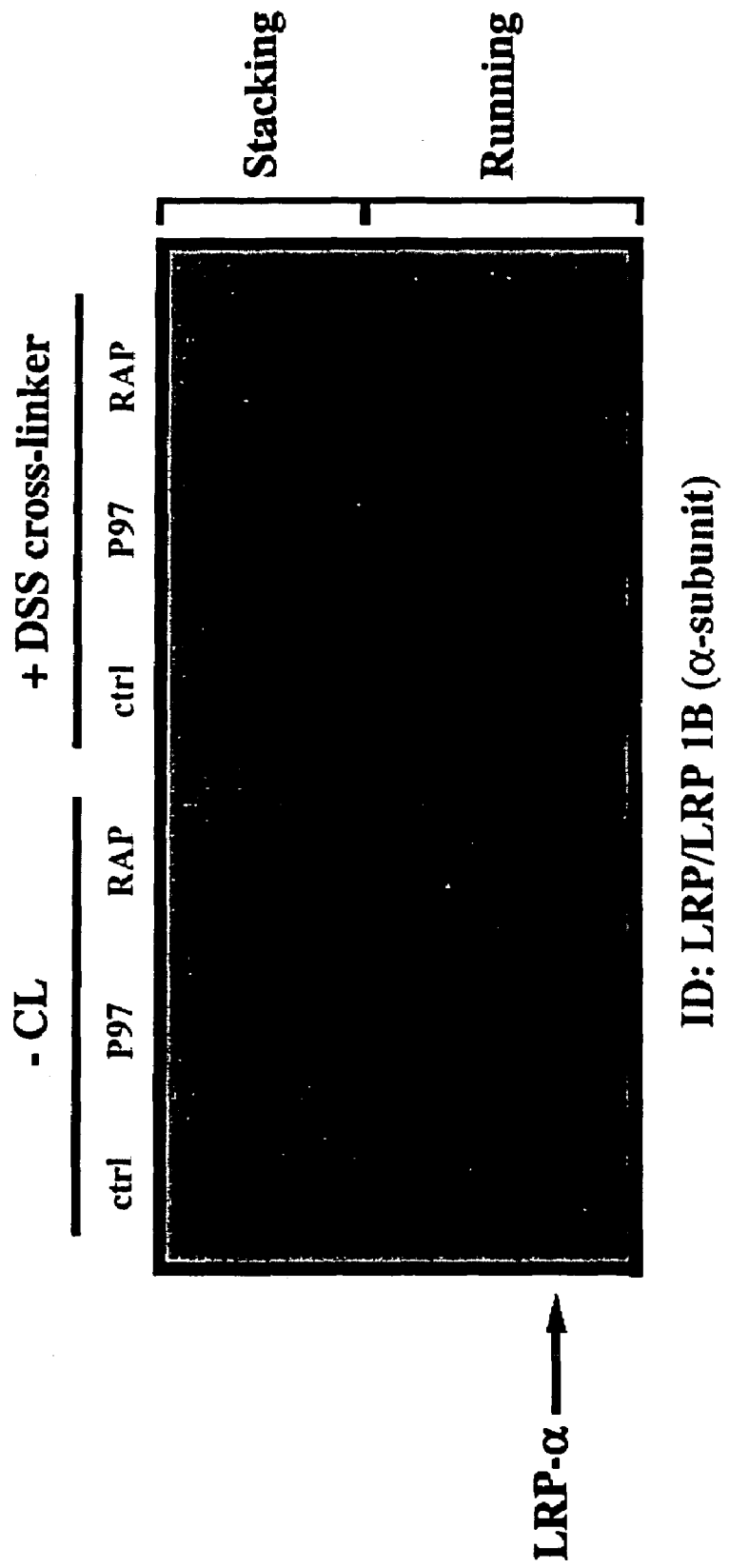

FIG. 29. LRP/LRP1B migrates as a high molecular weight dissociable complex in presence of p97. U-87 cells were grown in monolayer in six-multiwell microplates at 37° C. under 5% CO2. The cell monolayer were incubated at 4° C. with p97 or RAP in Ringer/Hepes solution. After incubation, cell monolayer was washed 3 times with cold-Ringer/Hepes solution and proteins were cross-linked with 1 mM DSS.

After, cells were lysed and equal quantities of protein (25 µg) were subjected to SDS-PAGE under non-reducing conditons and electroblotted onto PVDF membranes. LRP/LRP1B was immunodetected as described in Examples using a mouse monoclonal antibody raised against human LRP α-subunit (clone 8G1 from Research Diagnostics inc.) at a 1/500 dilution in TBS-Tween 0.1%, 3% BSA and 0.01% NaN$_3$. (n=2).

Figure 30:
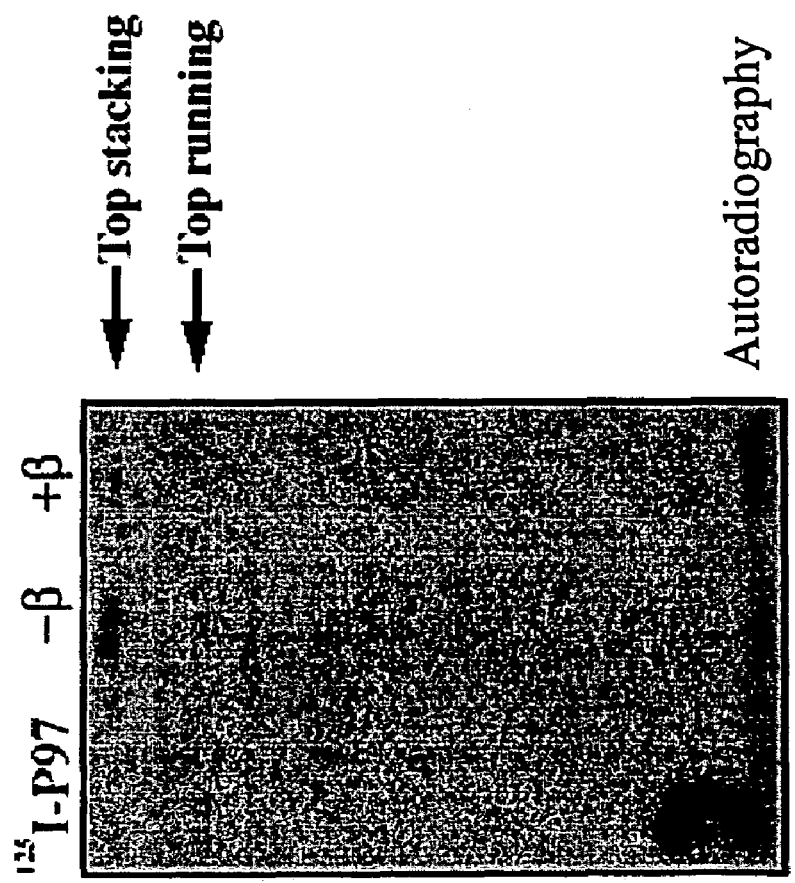

FIG. 30. Reducing condition induces release of p97 from high molecular weigh complex. U-87 cells were grown in monolayer in six-multiwell microplates at 37° C. under 5% CO2. The cell monolayer were incubated at 4° C. with [$^{125}$I]-p97 in Ringer/Hepes solution. After incubation, cell monolayer was washed with cold-Ringer/Hepes solution and [$^{125}$I]-p97 cross-linked was performed with 1 mM DTSP according to the manufacturer's protocol. After, cells were lysed and proteins were subjected to SDS-PAGE under reducing conditions or not. Autoradiography of [$^{125}$I]-p97 was performed following gel fixation and drying. (n=2)

Figure 31:
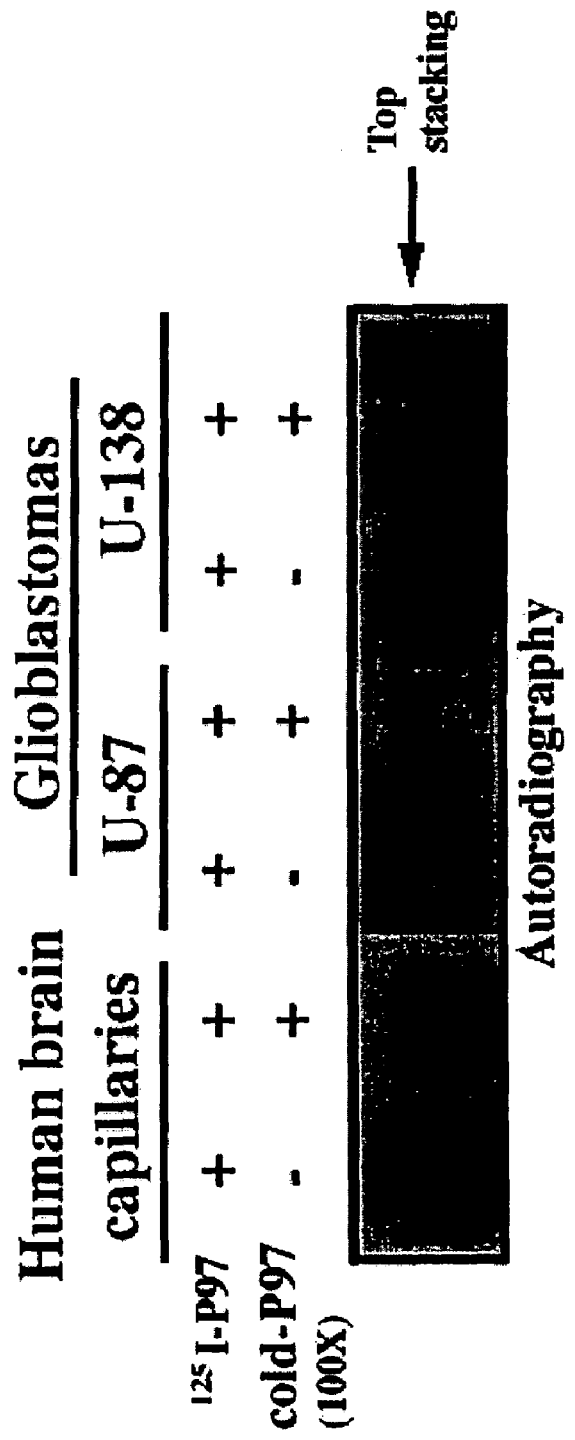

FIG. 31. p97 migrates as a high molecular weight protein complex. The ligand binding was performed as described in the Examples. Concerning human brain capillaries, the ligand binding was performed on 100 µg capillaries with the same protocol as cell monolayer. After ligand binding, cells were lysed with lysis buffer at 4° C. for 30 min. Equal quantities of protein were subjected to SDS-PAGE under non-reducing conditions. Autoradiography of [$^{125}$I]-p97 was performed following gel fixation and drying. (n=2)

Figure 32:
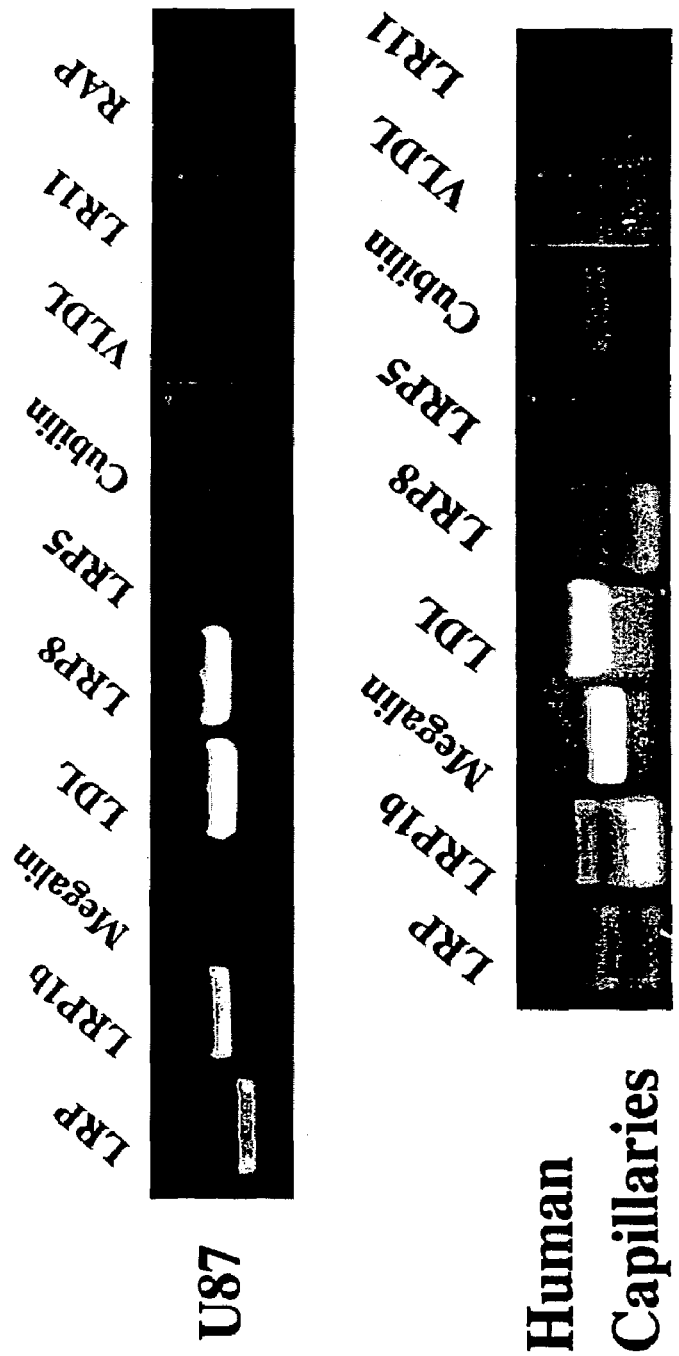

FIG. 32. Expression of members of LDL receptor family (RT-PCR). RNA from isolated human capillaries and U87 were performed as described in the Examples. The amplified PCR products were electrophoresed on a 2% agarose gel and visualized under ultraviolet light. (n=2).

Figure 34:
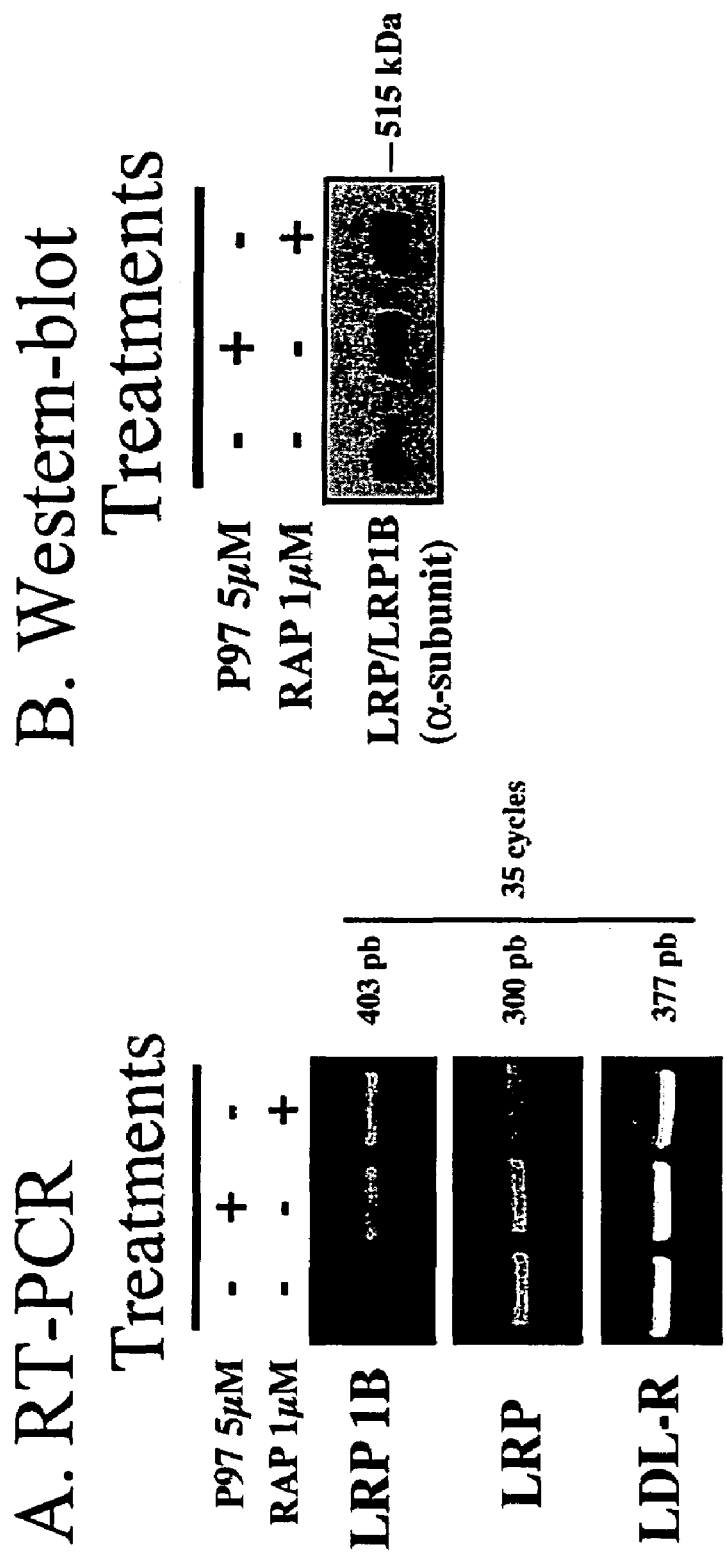

FIG. 34. Effect of p97 and RAP treatments in U-87 cells. A. Cells (2×10$^5$) were plated onto six-multiwell microplates and grown at 37° C. under 5% CO$_2$ with optimal culture medium supplemented with serum for 4 days. Treatment was performed in serum free medium for 72 hours. RNA isolation and RT-PCR were performed as described in the Examples. B. LRP/LRP1B was immunodetected in cells lysates as described in the Examples. Mouse monoclonal antibody raised against human LRP aŏ-subunit (clone 8G1 from Research Diagnostics inc.) was used at a 1/500 dilution in TBS-Tween 0.1%, 3% BSA and 0.01% NaN3. (N=2 for p97 treatment), (n=1 for RAP treatment)

Figure 35:
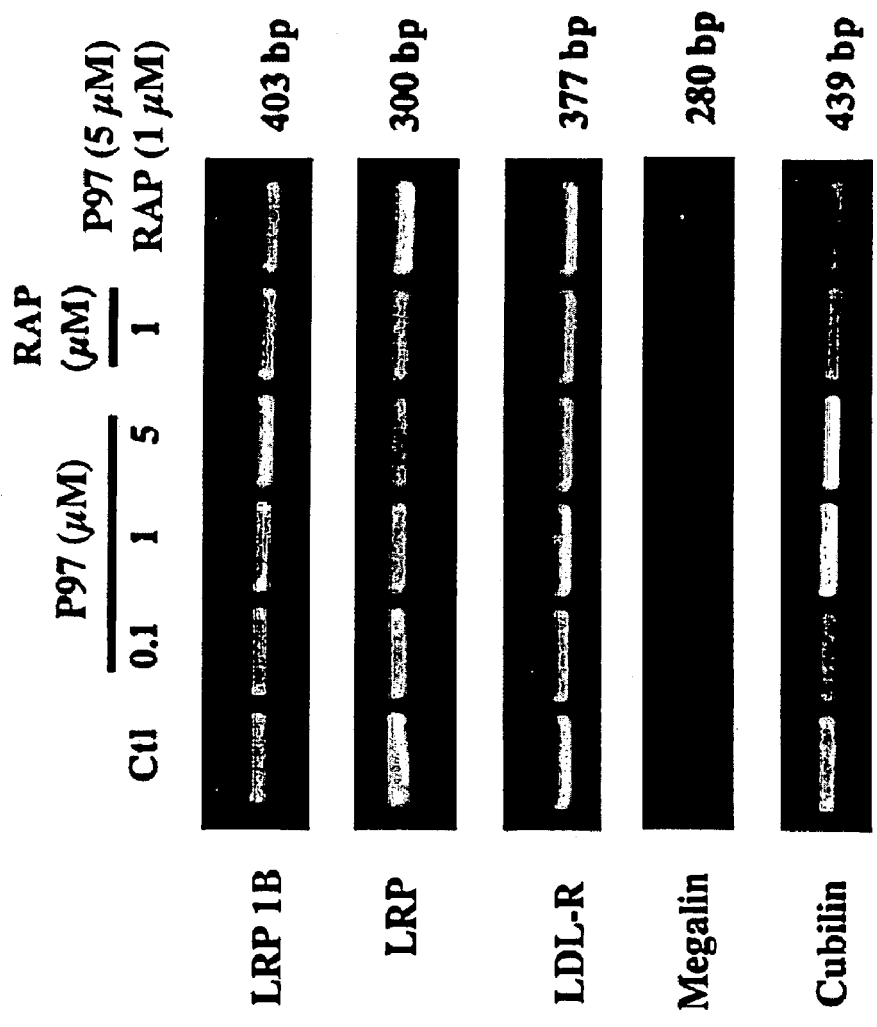

FIG. 35. Effect of p97 and RAP treatments in U-87 cells (RT-PCR). Cells (2×10$^5$) were plated onto six-multiwell microplates and grown at 37° C. under 5% CO2 with optimal culture medium supplemented with serum for 4 days. Treatment was performed in serum free medium for 72 hours. RNA isolation and RT-PCR were performed as described in the Examples. The amplified PCR products were electrophoresed on a 2% agarose gel and visualized under ultraviolet light. (n=2 for p97), (n=1 for RAP)

Figure 36:
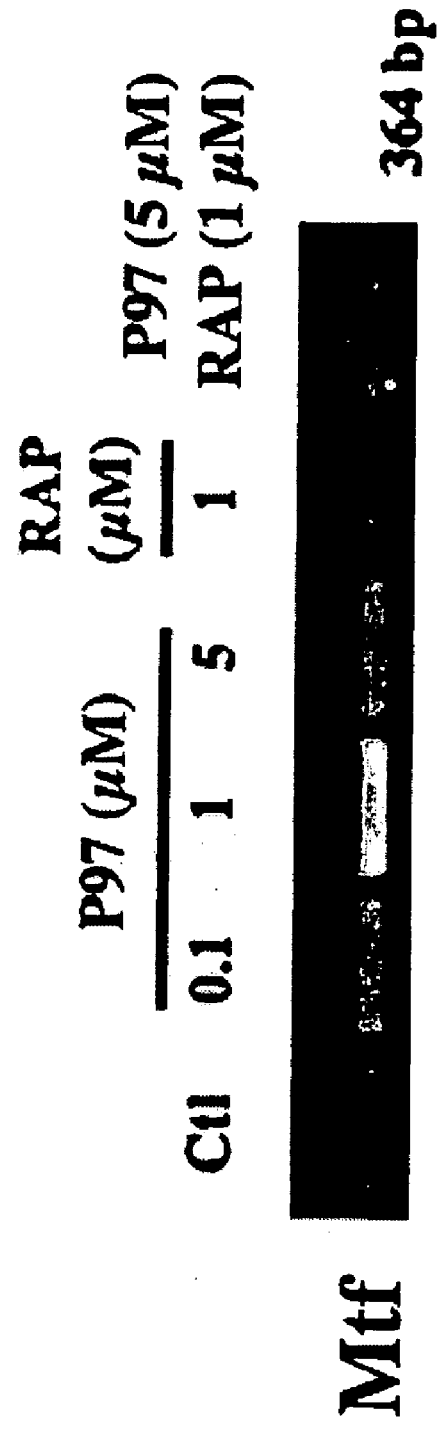

FIG. 36. Effect of p97 and RAP treatments in U-87 cells (RT-PCR) on endogenous melanotransferrin. Cells (2×105) were plated onto six-multiwell microplates and grown at 37° C. under 5% CO2 with optimal culture medium supplemented with serum for 4 days. Treatment with p97 and RAP was performed in serum free medium for 72 hours. RNA isolation and RT-PCR were performed as described in the Examples. The amplified PCR products were electrophoresed on a 2% agarose gel and visualized under ultraviolet light. (n=1).

Figure 37:
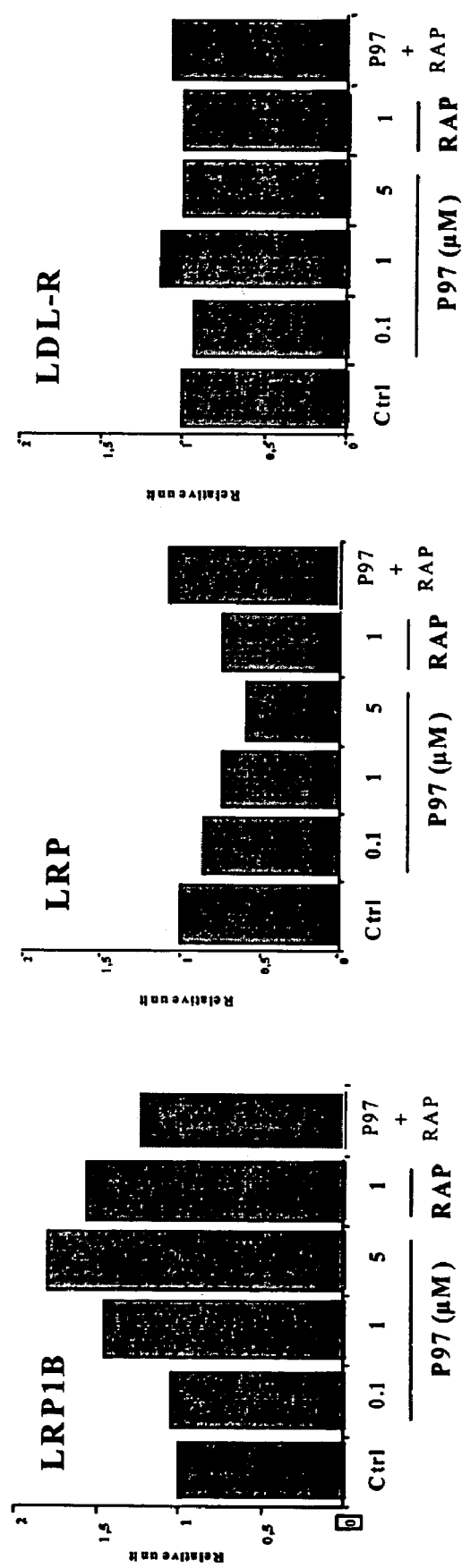

FIG. 37. Effect of p97 and RAP treatments in U-87 cells. FIG. 37a Agarose gel electrophoresis of PCR products. The amplified PCR products were electrophoresed on a 2% agarose gel and visualized under ultraviolet light. (n=1).

Figure 38:
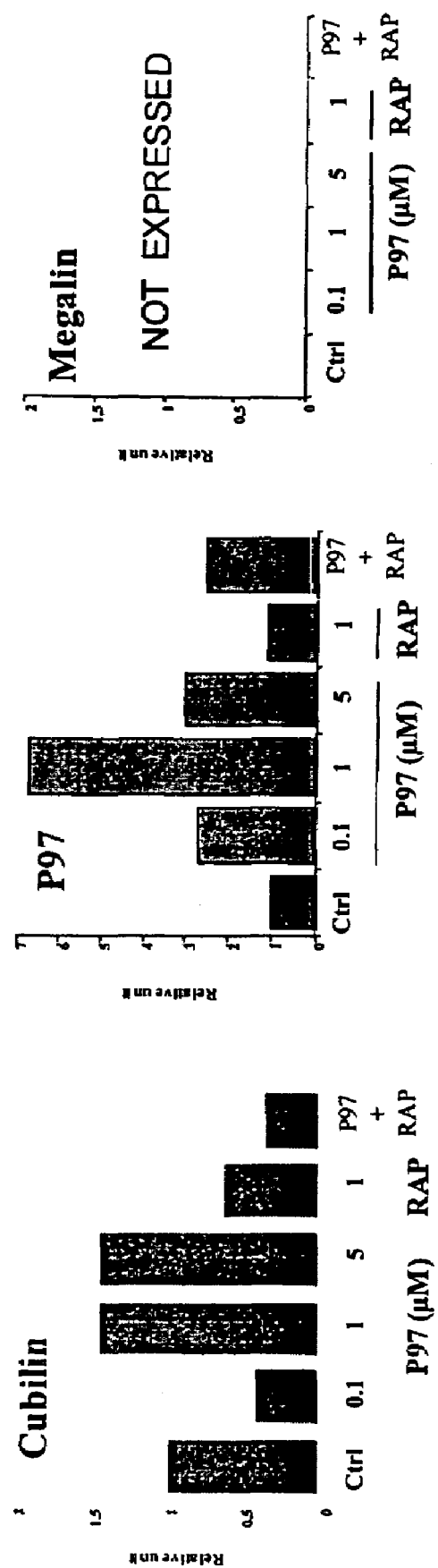

FIG. 38. Effect of p97 and RAP treatments in U-87 cells. The amplified PCR products were electrophoresed on a 2% agarose gel and visualized under ultraviolet light. (n=1). Quantification was by densitometry of p97 and RAP treatments on the RNA levels of LRP1B, LRP, LDL-R, cubilin, endogenous p97 and megalin. Results are expressed as ratios of RNA levels between control and treated U-87 cells.

Figure 39:

FIG. 39 show the expression of members of the LDL receptor family in MG1391. RT-PCR. RT-PCR was performed for members of the LDL-R family: LRP, LRP1B, megahn, LDL, VLDL, LRP8, LR11, LRP5 and cubulin. DNA (cDNA) synthesis was performed with 1 µg of total RNA using a cDNA one step synthesis kit (Invitrogen, USA) following the manufacturer's protocol. (1× of reaction mix, RNA 1 µg, 0.2 µM of both primers, 1 µl of RT/Platinum Taq mix). The cDNA generated was amplified using primers produced with MacVector 7.0 (Oxford molecular Ltd, Oxford, UK ). All the subsequent assays were then performed under conditions that produced amplifications of cDNA within a linear range. RT inverse-transcription was performed at 50° C. for 30 min. PCR amplification for 35 or 40 cycles for all was performed as follows: denaturation at 94° C. for 30 s, annealing at 60° C. for 30 s and extension at 72° C. for 1 min. Finalisation stage was performed at 72° C. for 5 min. Tubes containing all the ingredients except templates were included in all runs and served as negative controls. The amplified PCR products were electrophoresed on a 1% agarose gel in TAE (40 mM Tris, 360 mM acetic acid, 1 mM EDTA, 12.5 fM Ethidum bromide) and were visualized under ultraviolet light followed by densitrometric analysis.

Figure 40:
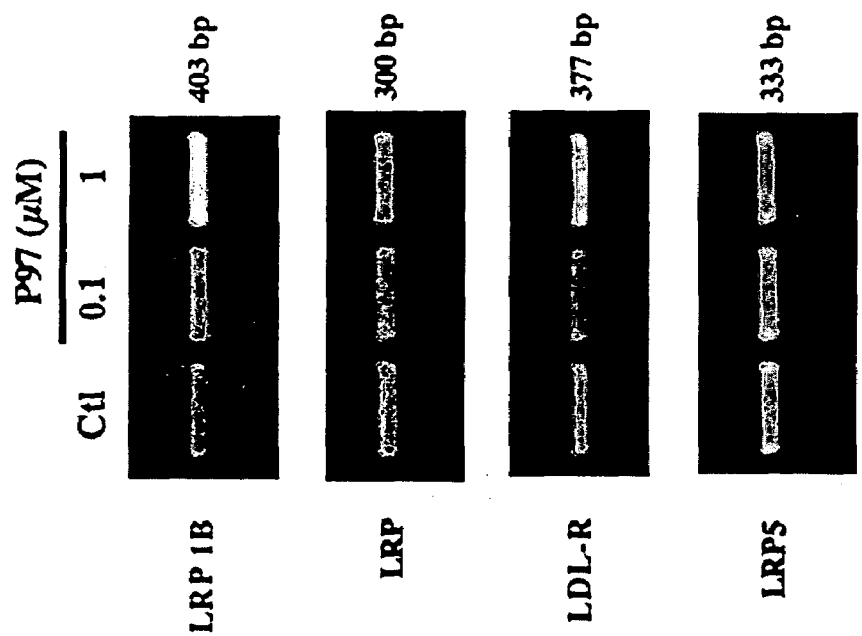

FIG. 40 shows the effect of p97 treatment on the expression of LRP1B, LRP, LDL-R, and LRP5 in MG1391 cells using the above methods.

Figure 41:
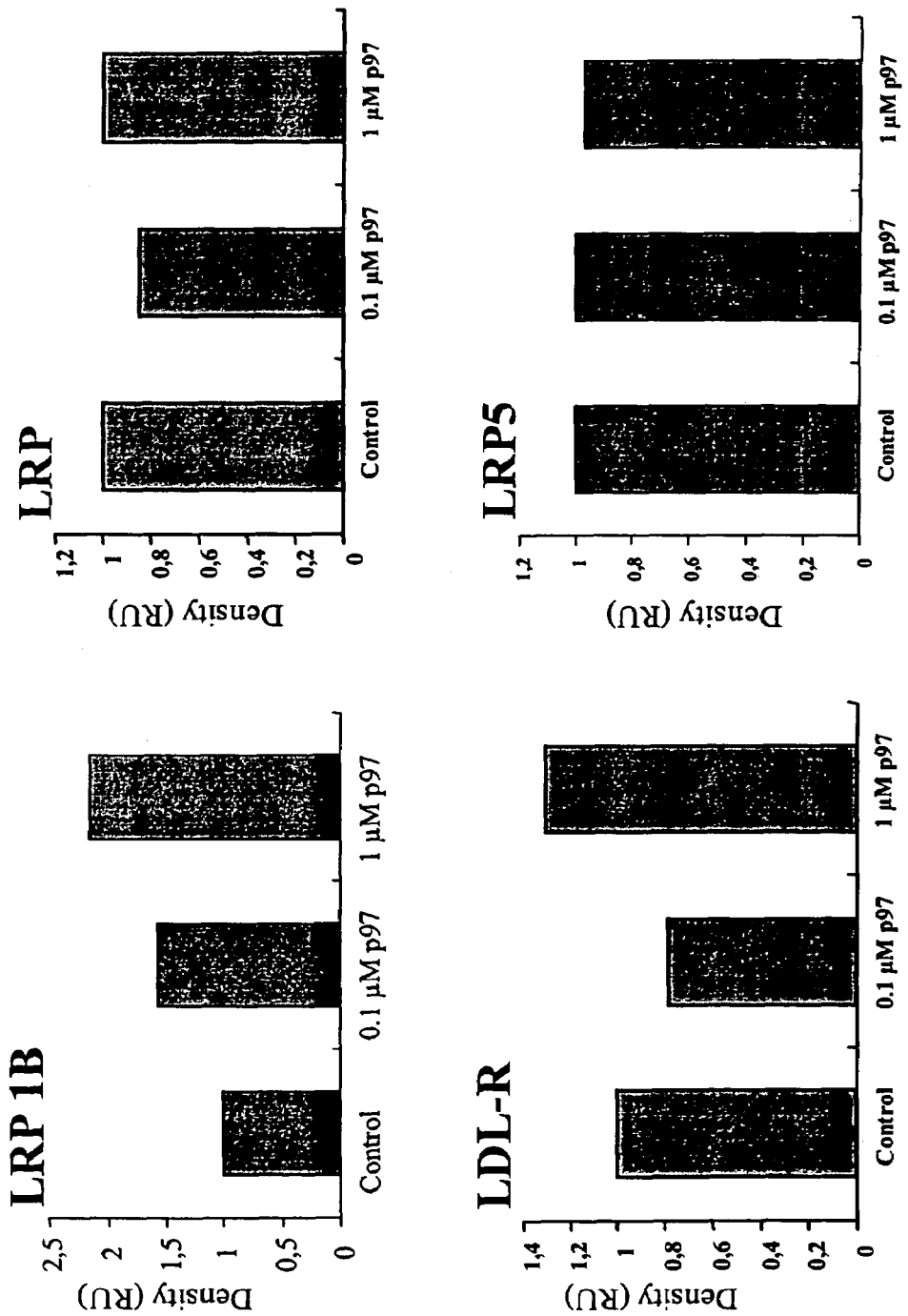

FIG. 41 shows the effect of p97 on the expression of LRP1B, LRP, LDL-R, and LRP5 in MG1391 cells using the above methods.

Figure 42:
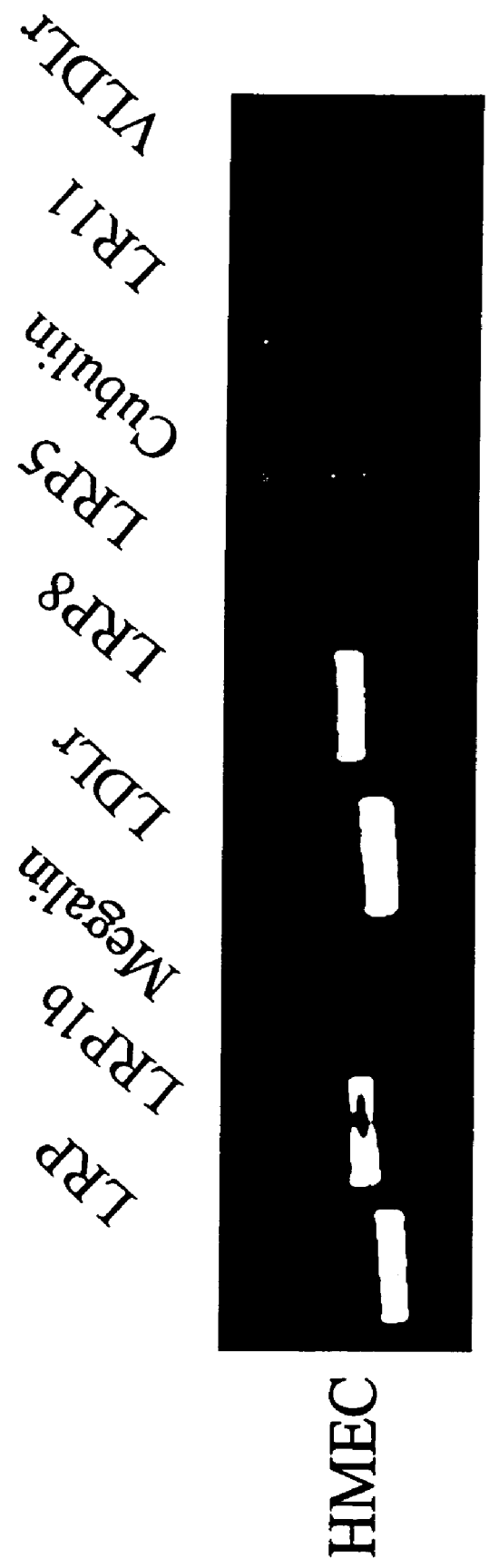

FIG. 42 shows the expression of LDL-receptor family members in human endothelial cells.

Figure 43:
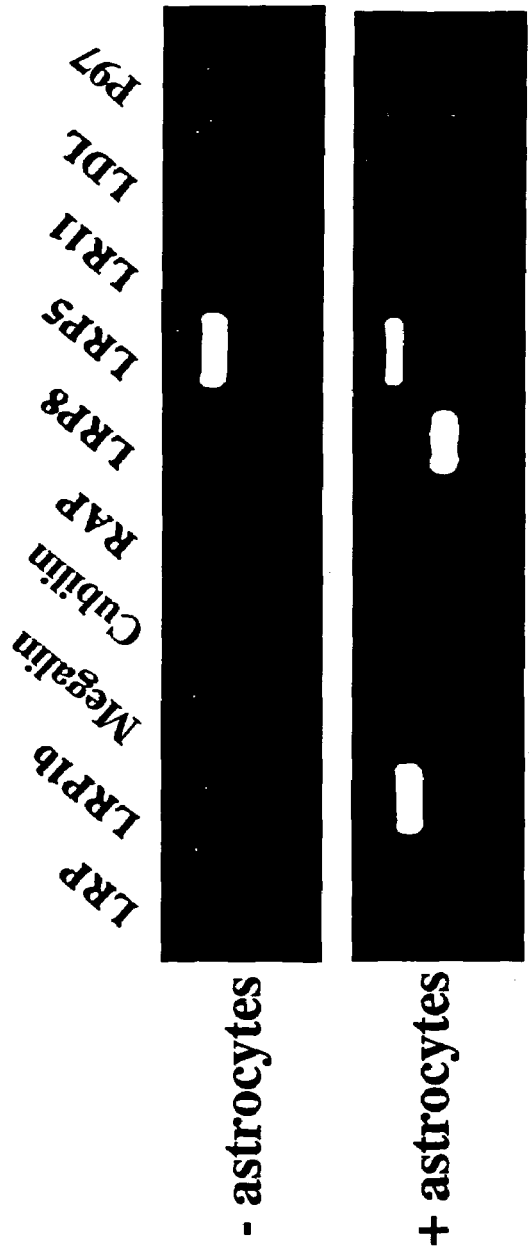

FIG. 43 shows the expression of LDL receptor family members in BBCE cells cultured in the presence and absence of astrocytes.

Figure 44:
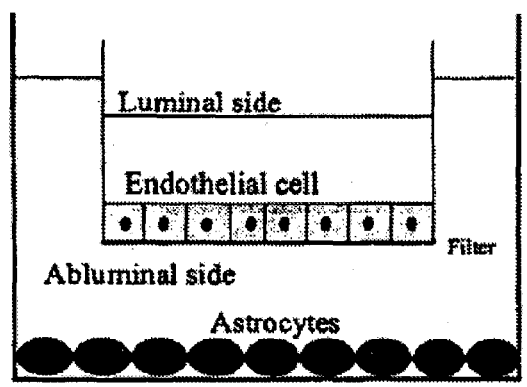

FIG. 44 shows an in vitro model of the blood brain barrier.

Figure 45:
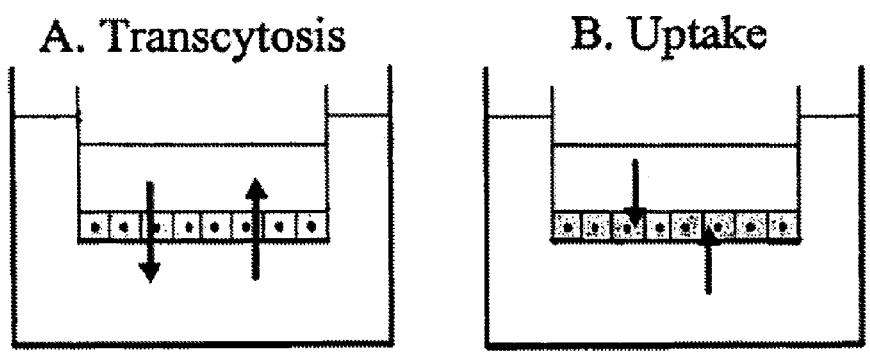

FIG. 45 shows a general scheme for performing transport assays in BBCEC monolayers.

DETAILED DESCRIPTION OF THE INVENTION

A. Overview

The present invention provides, inter alia, novel compounds, pharmaceutical compositions and methods for modulating the activity of the melanotransferrin receptor and for modulating the transcytosis, endocytosis, and blood brain barrier transport of active agents conjugated to melanotransferrin ("MTf" or "p97") or other ligands of LRP1, and more particularly, LRP1B. It also provides screening methods for identifying such compounds, compositions, and methods. The invention is based on the discovery, disclosed here for the first time, that melanotransferrin binding to brain capillary endothelial cells (BCECs) is competitively inhibited by lactoferrin (Lf), RAP, and β-amyloid protein, but not significantly by transferrin (Tf) or bovine serum albumin (BSA). This binding spectra establishes the p97 receptor is a member of the family of LRP family. This assignment is consistent with the characterization herein of the mechanism for p97 transcytosis and endocytosis.

The BCEC receptor for MTf is therefore not the transferrin receptor (Tf-R), as previously hypothesized, but an unrelated class of receptor (herein called the "MTf-R" or "p97 receptor") for which Lf is a competitive inhibitor of p97. This surprising discovery provides a new pathway for the uptake of MTf into the brain; and simultaneously identifies a new role for receptors of lactoferrin and/or β-amyloid proteins in BCECs, namely MTf binding and uptake.

The invention also relates to the unexpected discovery that LRP1B is a major p97 receptor involved in the transcytosis and endocytosis of p97. Applicants have, for instance, found that p97 binds to the LRP1B receptor to form a high molecule weight complex which is dissociable and subject to competitive inhibition. Applicants have also found that the trancystosis and uptake of p97 in cells is associated with their expression of the LRP1B gene and that LRP1B is induced by treatment with p97.

In addition, it has been discovered that, in contrast to several other tumors, the LRP1B gene is upregulated in astrocytomas. In a preferred embodiment, therefore, p97 and ligands binding LRP1B are conjugated to chemotherapeutic agents active against such cells.

In a preferred embodiment of the invention, MTf-R biological activity is modulated to influence blood-brain barrier transport of compounds conjugated to p97, and in a further preferred embodiment, MTf-R biological activity is modulated to influence the transport of melanotransferrin conjugated therapeutic agents (MTf-TA) into the brain.

In a further preferred embodiment, modulation of delivery across the blood-brain barrier is achieved by modulating the activity and/or expression of MTf-Rs on the serum face (i.e., the apical side, or the "inside" of the blood vessel) of brain capillary endothelial cells. The present invention therefore provides, inter alia, methods of modulating MTf-TA uptake into the brain, compositions useful for modulating MTf-TA uptake into the brain, and screening assays and methods for identifying modulators of MTf-TA uptake into the brain. The screening assays and compounds identified using such screening assays can also be used for modulating the expression and/or activity of Lf-Rs in general, and thus for treating the diseases and disorders associated with the expression and/or activity of Lf-Rs, such as those disclosed hereinbelow.

The blood-brain barrier (BBB) performs a neuroprotective function by tightly controlling access to the brain; consequently it also impedes access of pharmacological agents to cerebral tissues, necessitating the use of vectors for their transit. We have discovered that recombinant human melanotransferrin is highly transported into the brain by using animal models and a well-defined in vitro model of the BBB. Transcytosis of p97 is at least 14-fold higher than that of holo-transferrin, with no apparent intraendothelial degradation. The transport of p97 is not due to changes in endothelial barrier integrity but to receptor-mediated endocytosis. We have also discovered a member of the low-density lipoprotein receptor protein family, likely LRP, is involved in p97 transendothelial transport. The brain accumulation, high rate of p97 transcytosis and its very low level in the blood (100,000-fold lower than transferrin) indicate that p97 is particularly and advantageous carrier as a delivery system to target drugs directly to the brain.

Blood-brain barrier (BBB) permeability is frequently a rate-limiting factor for the penetration of drugs or peptides into the central nervous system (CNS) (see Pardridge, W. M. *J. Neurovirol.* 5: 556-569 (1999), Bickel, U., Yoshikawa, T. & Pardridge, W. M. *Adv. Drug Deliv. Rev.* 46: 247-279 (2001)). The brain is shielded against potentially toxic substances by the BBB, which is formed by brain capillary endothelial cells that are closely sealed by tight junctions. In addition, brain capillaries possess few fenestrae and few endocytic vesicles, compared to the capillaries of other organs (see Pardridge, W. M. *J. Neurovirol.* 5: 556-569 (1999)). There is little transit across the BBB of large, hydrophilic molecules aside from some specific proteins such as transferrin, lactoferrin and low-density lipoproteins, which are taken up by receptor-mediated endocytosis (see Pardridge, W. M. *J. Neurovirol.* 5: 556-569 (1999); Tsuji, A. & Tamai, I. *Adv. Drug Deliv. Rev.* 36: 277-290 (1999); Kusuhara, H. & Sugiyama, Y. *Drug Discov. Today* 6:150-156 (2001); Dehouck, B. et al. *J. Cell. Biol.* 138: 877-889 (1997); and Fillebeen, C. et al. *J. Biol. Chem.* 274: 7011-7017 (1999)).

Melanotransferrin is a glycosylated protein that was first named human melanoma antigen p97 when it was found at high levels in malignant melanoma cells (see Brown, J. P., Woodbury, R. G., Hart, C. E., Hellstrom, I. & Hellstrom, K. E. *Proc. Natl. Acad. Sci. U.S.A.* 78: 539-543 (1981); and Brown, J. P. et al. *Nature* 296:171-173 (1982)). It was later renamed Mtf due to its high level of sequence homology (37-39%) with human serum transferrin, human lactoferrin and chicken transferrin. (See Brown, J. P. et al. *Nature* 296:171-173 (1982), Rose, T. M. et al. *Proc. Natl. Acad. Sci. U.S.A.* 83,1261-1265 (1986)). In contrast to transferrin and lactoferrin, no cellular receptor for p97 has been identified. It has also been shown that p97 reversibly binds iron and that it exists in two forms, one of which is bound to cell membranes by a glycosyl phosphatidylinositol anchor while the other form is both soluble and actively secreted (see Baker, E. N. et al. *FEBS Lett.* 298: 215-218 (1992); Alemany, R. et al. *J. Cell Sci.* 104: 1155-1162 (1993); and Food M. R. et al. *J. Biol. Chem.* 269: 3034-3040 (1994)). The exact physiological role of membrane-bound p97 remains to be clearly established while the function of secreted p97 is largely unexplored (see Sekyere, E. and Richardson, D. R. *FEBS Lett.* 483: 11-16, (2000)).

More recently, it was reported that p97 mRNA is also widespread in normal human tissues, with the highest levels in salivary glands (see Richardson, D. R. *Eur J Biochem.* 267: 1290-1298 (2000)). In normal human brain, p97 is present in capillary endothelium whereas in brain from patients with Alzheimer's disease it is located in microglial cells associated with senile plaques (see Rothenberger, S. et al. *Brain Res.* 712: 117-121 (1996); Jefferies, W. A. et al. *Brain Res.* 712: 122-126 (1996); and Yamada, T. et al. *Brain Res.* 845: 1-5 (1999)). Serum contains very low levels of p97 (Brown, J. P., Woodbury, R. G., Hart, C. E., Hellstrom, I. & Hellstrom, K. E. *Proc. Natl. Acad. Sci. U.S.A.* 78: 539-543 (1981). The fact that p97 levels are very low in serum while high p97 levels are reported in senile plaques shows that p97 crosses the BBB to a greater extent than do other proteins present in the serum.

To investigate this hypothesis we evaluated the uptake of p97 in brain following its administration in animals and compared it to those of holo-transferrin and bovine serum albumin (BSA). We further studied and characterized p97 transcytosis using a well-established model of the BBB, consisting of bovine brain endothelial cells (BBCECs) co-cultured with rat astrocytes. (see Fillebeen, C. et al. *J. Biol. Chem.* 274: 7011-7017 (1999); (Dehouck, M. P. et al. *J. Neurochem.* 58: 1790-1797 (1992)). We also used isolated human brain capillaries for measuring p97 uptake.

The results obtained with in vivo and in vitro models show a much greater passage of p97 across the BBB than holo-transferrin and further indicate the low-density lipoprotein receptor-related protein (LRP) might be involved in its passage.

p97 transcytosis is 14 times higher than transferrin transcytosis. Transcytosis is mediated by a receptor as it is temperature sensitive, saturable, and p97 conformation-dependent. Transcytosis of p97 occurs without compromising the structural integrity of the blood brain barrier (BBB) and p97 is not substantially degraded.

B. Definitions

"Melanotransferrin," as used herein, is sometimes referred to as "MTf" or "p97". As used in this disclosure, MTf includes membrane bound p97 (ie., p97 attached to a GPI anchor or some other anchor), secreted p97, soluble p97, cleaved p97, analogs of p97 which are equivalents of p97 (having greater than 40% homology at the peptide sequence level, including allelic variants of p97), human, mouse, chicken and/or rabbit p97, and derivatives, portions, or fragments thereof. p97 can be in the form of acidic or basic salts, or in its neutral form. In addition, individual amino acid residues can be modified, such as by oxidation or reduction. Moreover, various substitutions, deletions, or additions can be made to the amino acid or nucleic acid sequences, the net effect of which is to retain or improve upon the desired biological activity of p97. Due to code degeneracy, for example, there may be considerable variation in nucleotide sequences encoding the same amino acid sequence.

"p97 fragment," as used herein, includes any portion of p97 or its biologically equivalent analogs that contains a sufficient portion of p97 to enable it to bind to the MTf-R and to be transported across the blood-brain barrier; or that otherwise retains or improves upon the desired biological activities of p97.

"Melanotransferrin conjugated therapeutic agent" or, alternatively, "MTf-TA," as used herein, refers to a composition comprising p97 or a p97 fragment covalently conjugated to another compound. The conjugation can be direct or indirect (ie., through an extended linker) so long as it is a chemical conjugation. Linkers may be as taught in U.S. Provisional Patent Application titled, "The Use of Isocyanate Linkers for the Synthesis of Hydrolyzable Active Agent Biopolymer Conjugates" with inventors Qingqi Chen, Damian Sowa, and Reinhard Gabathuler, filed on Jul. 12, 2002 and assigned to the same assignee as the present application, and herein incorporated by reference in its entirety.

The general construct of the MTf-TA of the present invention is as follows:

p97—Linker—Compound

Melanotransferrin conjugated therapeutic agents (MTf-TAs) can be used to treat many diseases including, but not limited to, neurological diseases and conditions such as Alzheimer's Disease, Parkinson's Disease, schizophrenia, epilepsy and others; neurological cancers, such as primary brain tumors including glioma, meningioma, neurinoma, pituitary adenoma, medulloblastoma, craniopharyngioma, hemangioma, epidermoid, sarcoma and intracranial metastasis from other tumor sources; and neurological infections or inflammatory conditions. Further, MTf-TAs can be used to treat non-CNS (ie., non-BBB delimited) diseases, such as cancers, diseases and conditions of non-CNS organs. Detailed descriptions of MTf-TAs and their uses are set out in U.S. Patent Application Nos. 60/226,242 and 60/226,254, the teachings of which are incorporated herein by reference.

"Modulate," as used herein, refers to the ability to alter, by increase or decrease (e.g., to act as an antagonist or agonist).

"Melanotransferrin receptor" ("MTf-R"), as used herein, refers to any biological system that specifically or preferentially binds MTf. This term is intended to include those receptors which competitively bind Lf and/or β-amyloid protein, but excludes those receptors which are specific for Tf such as the transferrin receptor (Tf-R) (which is described at OMIM #*190010, and which is also known as TFR, TRFR and CD71). A receptor known to specifically or preferentially bind Lf is herein called a "lactotransferrin receptor" (Lf-R). Known Lf-Rs include, but are not limited to, the LDL-related receptors. A known LDL-related receptor is lipoprotein receptor-related protein/alpha2-macroglobulin receptor ("LRP1"). The term MTf-R specifically includes other receptors found on endothelial cells that specifically bind both MTf and Lf, but not Tf. In a preferred embodiment, the MTf-R is the LRP1. In a more preferred embodiment, the MTf-R is LRP1B.

Members of the low density lipoprotein (LDL) receptor family include LDL-R (132 kDa); LRP/LRP1 and LRP1B (600 kDa); Megalin ((LRP2), 600 kDa); VLDL-R (130 kDa); ER-2 (LRP-8, 130 kDa); Mosaic LDL-R (LR11, 250 KDa); and other members such as LRP3, LRP6, and LRP-7. Characeristic features of the LDL-R family include cell-surface expression; extracellular ligand binding domain repeats (Dx-SDE); requirement of Ca++ for ligand binding; recognition of RAP and ApoE; EGF precursor homology domain repeats (YWTD); single membrane spaning region; internalization signal in the cytoplasmic domain (FDNPXY); and receptor mediated endocytosis of various ligands.

LRP refers to the low density lipoprotein receptor related protein and members of this receptor family. LRP is a large protein of 4525 amino acids (600 kDa) which is cleaved by furin to produce two subunits of 515-(α) and 85-(β) kDa that remain non-covalently bound. LRP is mainly expressed in the liver, kidney, neuron, CNS, BBB, SMC and various cultured cells.

LRP ligands. A number of molecules are known to bind LRP. These molecules include, for instance, lactoferrin, RAP, lipoprotein lipase, ApoE, Factor VIII, β-amyloid precursor, α2-macroglobulin, thrombospondin 2 MMP-2, MPP-9-TIMP-1; uPA:PAI-I:uPAR; and tPA:PAI-1:uPAR (see also FIG. 23).

LRP 1B is a recently discovered member of the low density lipoprotein receptor family. 600 kDa multifunctional cell surface receptor. See Liu et al., *J. Biol. Chem.* 276 (31):28889-28896 (2001). See also Liu et al., *Genomics* 69, 271-274 (2000); and Liu et al., *Cancer Res.* 60, 1961-1967 (2000). This receptor is more closely related to LRP than megalin and shares a 59% homology at cDNA level and a 52% homology at predicted amino acid level. the LRP 1B gene is expressed in the brain, thyroid and salivary gland. Known ligands for LRP 1B include RAP, tPA, PAI-1.

Mouse LRP1B is accessible through GenBank Accession Nos. XM 143023 XM 130241. Human LRP1B is accessible through GenBank Accession Nos. XM 015452.

"Lipoprotein receptor-related protein/alpha2-macroglobulin receptor" ("LRP1"), as used herein, refers to a multifunctional receptor. It is believed that the clustering of cysteine-rich type. A binding repeats, resembling those found in the LDL receptor, is the molecular principle for the ability to bind a variety of ligands that were previously thought to be unrelated: activated alpha-2-macroglobulin, apolipoprotein E, lipoprotein lipase, plasminogen activators and complexes with their inhibitor (PA and PA/PAI-1), lipoprotein(a), pseudomonas exotoxin A, human rhinovirus, Lf and the so-called receptor associated protein (RAP). See, Meilinger, et al., *FEBS Let.*, 360:70-74 (1995).

LRPI is accessible through GenBank Accession No.: X 13916 and Swiss-Prot Primary Accession No.: Q07954.

Alternative names for the LRP1 gene/protein include: Low-density lipoprotein receptor-related protein 1 [precursor], LRP, Alpha-2-macroglobulin receptor, A2MR, Apolipoprotein E receptor, APOER, CD91, LRP1 or A2MR.

The screening assays and other embodiments of this invention can also employ homologs of human LRP1 (hLRP1) or LRP1B. Such homologs can be derived from other organisms, specifically eukaryotes and preferably from mammals.

Preferred homologs of human LRP include, but are not limited to, the following LRP proteins:

| H. sapiens: | SP:Q07954 - LRP1_HUMAN LOW-DENSITY LIPO-PROTEIN RECEPTOR-RELATED PROTEIN 1 PRECURSOR | 100%/4543 aa |
|---|---|---|
| M. musculus: | PID:g49942 - AM2 receptor | 97%/4543 aa |
| R. norvegicus: | SP:P98158-LRP2 RAT LOW-DENSITY LIPO-PROTEIN RECEPTOR-RELATED PROTEIN 2 PRECURSOR | 39%/4207 aa |
| D. melanogaster: | SP:P98163 - YL DROME PUTATIVE VITELLOGENIN RECEPTOR PRECURSOR | 28%/1550 aa |
| C. elegans: | PID:g3876533 - predicted using Genefinder | 35%/4205 aa |
| S. cerevisiae: | PID:g557822 - mal5, stal, len: 1367. CAI: 0.3, AMYH YEAST P08640 GLUCOAMYLASE S1 | 24%/1221 aa |
| E. coli: | PID:g1787636 - putative membrane protein | 25%/370 aa |

Those skilled in the art can readily identify other homologs of LRP1 or more particularly, LRP1B, suitable for use in the present invention.

"Receptor for Advanced Glycation End products" ("RAGE"), as used herein, refers to a multiligand member of the immunoglobulin superfamily of cell surface molecules. RAGE was originally identified and characterized based on its ability to bind advanced glycation end products (AGEs), adducts formed by glycoxidation that accumulate in disorders such as diabetes and renal failure. Subsequent studies demonstrate that RAGE serves as a cell surface receptor for amyloid-β peptide (the cleavage product of β-amyloid precursor protein (β-APP), a major component of neuritic plaques of Alzheimer's Disease). Other ligands include amphoterin and s100/calgranulin-like molecules (see, Hofmann, et al., *Cell*, 97(7):889-901 (1999)). RAGE is readily accessible through GenBank Accession No.: M91211 and Swiss-Prot Primary Accession No.: Q15109.

By "determining the functional effect" is meant assaying for a compound that modulates, e.g., increases or decreases, a parameter that is indirectly or directly under the influence of the MTf-R, e.g., functional, physical and chemical effects. In addition to the functional effects specifically described herein, it will be readily apparent to those of skill in the art that other functional effects can be measured by any means known to those skilled in the art, e.g., changes in spectroscopic characteristics (e.g., fluorescence, absorbance, refractive index), hydrodynamic (e.g., shape), chromatographic, or solubility properties, changes in gene expression of MTf-Rs, and the like.

"Inhibitors," "activators" and "modulators" of MTf-Rs are used interchangeably to refer to inhibitory, activating or modulating compounds identified using in vitro and/or in vivo assays for MTF-R.

Samples or assays comprising MTf-Rs that are treated with a potential activator, inhibitor, or modulator are compared to control samples without the inhibitor, activator, or modulator to examine the extent of inhibition. Control samples (untreated with inhibitors) are assigned a relative MTf-R activity value of 100%. Inhibition of a MTf-R is achieved when the MTf-R activity value relative to the control is about 80%, preferably 50%, more preferably 25-0%. Activation of a MTf-R is achieved when the MTf-R activity value relative to the control (untreated with activators) is 10%, more preferably 150%, more preferably 200-500% (i.e., two to five fold higher relative to the control), more preferably 1000-3000% higher.

C. Screening Assays for Modulators of Melanotransferrin Receptors (MTf-Rs)

The present invention provides a screening assay employing an MTf-R, wherein compounds are tested for their ability to influence a measurable activity of the MTf-R. The MTf-R can be situated in a whole cell, a cell extract, semi-purified, purified or any other format that allows for measurement of its activity. The activity can be any activity in the expression, function or degradation of MTf-R including, for example, the amount or timing of such activities. Such activities include, for example, transcription, transcript processing, translation or transcript stability of the MTf-R gene sequence or mRNA transcript. Such activities include, for example, the synthesis of new MTf-R, the sub-cellular localization of MTf-R and activation of MTf-R biological activity. Such activities include, for example, the ability of MTf-R to bind substances, adopt conformations, catalyze reactions, bind known ligands and the like. Such activities include, for example, the amount or stability of MTf-R, the processing and removal or degradation of MTf-R and the like. In preferred embodiments, the MTf-R receptor for use in screening is LRP1 or LRP1B.

In a preferred screening assay, compounds are tested to identify modulators of a biological activity of MTf-R such as: MTf-R interactions with MTf, MTf-R interactions with Lf or other putative ligands or uptake of iron/other metal; transport of MTf across the blood-brain barrier ("BBB"), i.e., in a BBB model; transport of Lf, other ligands or metals across a BBB model; and/or measurement of the rate or amount of transcription, translation or expression levels of MTF-R genes or mRNA.

The invention contemplates a variety of different screening formats. Some designs are considered low throughput and test only one or a few compounds in series or in parallel. High throughput screening assays are suitable for screening tens of thousands or hundreds of thousands of compounds in a matter of weeks or months. "In silico" screening formats employ computer-aided rational design techniques to identify potential modulators of MTf-R biological activity.

The test compounds of the invention may be obtained from any source, but a preferred commercial embodiment employs commercially available compound libraries of hundreds of thousands of compounds, many of which are potential therapeutic agents. These compounds are tested in series or in parallel to identify modulating activity of MTf-R activity. Preferred test compounds can be identified by examining known and putative ligands of MTf-R for predicting chemical structure of inhibitors, etc. Other computer-aided design techniques can be employed to eliminate unsuitable candidates, such as those candidates thought to cause toxic side-effects. Those skilled in the art are familiar with the combinatorial and medicinal chemistry techniques that can be used to further select test compounds and the potential therapeutic agents of the invention.

The object of the screening assays is to identify modulators of MTf-R activity that are suitable for animal or human clinical trials and as therapeutic agents. As such, the screening assays identify stimulants, agonists or antagonists of MTf-R.

The method of identifying stimulants, agonists or antagonists of MTf-R can comprise contacting a substance suspected of being a stimulant, agonist or antagonist with MTf and the MTf-R under conditions such that MTf is capable of binding to the MTf-R; measuring the amount of MTf bound to the MTf-R; and determining the effect of the substance by comparing the amount of MTf bound to MTf-R with an amount determined for a control. The MTf that can be used in this method includes MTf cleaved of GPI, soluble MTf, cleaved MTf or derivatives thereof, preferably recombinant MTf. In this method of the invention, the amount of MTf bound to MTf-R can be determined by measuring the amount of MTf bound to the MTf-R, the amount of unbound MTf or the amount of unbound MTf-R. MTf bound to MTf-R can be isolated by conventional isolation techniques, for example, salting out, chromatography, electrophoresis, gel filtration, fractionation, absorption, polyacrylamide gel electrophoresis, agglutination, or combinations thereof. To facilitate the measurement of MTf bound to MTf-R or of unbound MTf, or unbound MTf-R, antibodies against MTf or MTf-R can, for example, be utilized.

In one embodiment, the invention also relates to a method for identifying a stimulant, agonist or antagonist of MTf-mediated iron uptake comprising: incubating a cell expressing MTf-R on its surface and a test substance (e.g., compound) suspected of being a stimulant, agonist or antagonist of MTf-R in the presence of MTf bound to iron (holo-MTf) and in the absence of transferrin, measuring the amount of iron uptake into the cell and identifying a stimulant, agonist or antagonist of MTf-R mediated iron uptake by comparing the amount of iron uptake in the cell with the amount of iron uptake in a cell from a control incubation in the absence of the test substance. Iron uptake refers to the internalization of iron into the cell across the cell plasma membrane.

D. Modulating Uptake of Melanotransferrin Conjugated Therapeutic Agents (MTf-TAs) by Modulating MTf-R Activity In another embodiment, the present invention relates to a method of using compounds that modulate MTf-R biological activity to modulate the amount of uptake into the cells of melanotransferrin conjugated therapeutic agents (MTf-TAs). In particular, the invention relates to a method of increasing the uptake of an MTf-TA into the brain, the method comprising administering a modulator of MTf-R biological activity either contemporaneously or sequentially with the MTf-TA. Alternatively, the invention relates to a method to reduce uptake of an MTf-TA into the brain comprising administering a modulator of MTf-R biological activity either contemporaneously or sequentially with the MTf-TA. In a preferred embodiment, these methods employ modulators of MTf-R that are first identified using a screening assay as described hereinabove. In preferred embodiments, the MTf-R receptor for use in screening is LRP1 or LRP1B.

Those skilled in the art will appreciate that increasing MTf-TA uptake and delivery across the blood-brain barrier is useful and desirable in situations such as, but not limited to, where the MTf-TA is being used to treat a neurological condition and increased amounts of delivery provide therapeutic benefit. Those skilled in the art will appreciate that decreasing MTf-TA uptake and delivery across the blood-brain barrier is useful and desirable for a variety of reasons including, but not limited to, where the MTf-TA is being used for its cardio-protective effect or used in other (non-CNS) organs and side-effects of brain uptake are to be avoided.

Modulators of MTf-R activity can be readily identified using a modification of the transwell apparatus set out in Example I below. In the modified form, a compound is added to the luminal surface of the cells in the transwell apparatus in combination with MTf-TAs. The compound is then scored to determine if it increases or decreases the transport of the MTf-TA across the BBCECs to the abluminal side. A library of compounds can be readily screened or tested to identify pharmacologically superior modulators.

E. Diseases Treatable by Lf-R Modulators

As a result of the surprising discovery that certain MTf-Rs are Lf-Rs, it has now been discovered that modulators of Lf-R biological activity can have an impact on disease processes known to be linked to MTf biological activity. As such, the following uses for modulators of Lf-Rs identified, for example, by the screening assays of the present invention have now been identified.

1) Rapidly proliferating cells, such as malignant cells, have an increased requirement for iron and must possess efficient mechanisms to obtain iron. Limiting the ability of malignant cells to acquire iron provides a method of killing tumor cells or of modulating their uncontrolled cell growth.

2) These findings lead to the discovery that modulators of Lf-R can be used to modulate iron uptake in cells. Iron uptake in cells can be modulated by varying the amount of Lf-R on cell surfaces, or by inhibiting Lf-R binding to MTf. Accordingly, stimulants, agonists or antagonists of Lf-R can be useful in the treatment of conditions or diseases where there is a disturbance in iron metabolism. For example, such substances are useful in the treatment of conditions such as hemochromatosis, neurodegenerative diseases, ischemic tissue damage, including ischemic stroke or trauma, heart disease and tumors (e.g., skin cancer).

3) MTf plays a role in the binding and uptake of other metals such as zinc and aluminum (Sekyere, E. and Richardson, D. R., *FEBS Letters,* 483:11-16 (2000) and, thus, modulation of Lf-R activity or expression plays a role in modulating or regulating Alzheimer's Disease or metaloproteins, such as zinc-dependent metaloproteins.

4) Conditions that involve disturbances in iron metabolism that can be treated using the compounds and methods of the invention (ie., using stimulants, agonists and antagonists of MTf-mediated iron uptake) are, for example, those involving excessive iron absorption from the diet, defects in iron uptake into cells, excessive iron uptake into cells or those requiring regular treatment by blood transfusion (e.g., dyserythropoietic anemias, in particular thalassaemia disorders. Examples of such conditions include, but are not limited to, hemochromatosis, neurodegenerative diseases (e.g., Alzheimer's Disease, Huntington's Disease and Parkinson's Disease), ischemic tissue damage, heart disease and tumors, inflammation and infections (see, Pippard, "Clinical Use of Iron Chelation," in *Iron in Immunity, Cancer and Inflammation* (M. de Sousa and J. H. Brock (Eds.), 1989, John Wiley & Sons), which is incorporated herein by reference.

5) Diseases which can be treated using modulators of Lf-R activity or expression include neurological diseases and conditions such as Alzheimer's Disease, Parkinson's Disease, schizophrenia, epilepsy and others, neurological cancers, such as primary brain tumors including glioma, meningioma, neurinoma, pituitary adenoma, medulloblastoma, craniopharyngioma, hemangioma, epidermoid, sarcoma and intracranial metastasis from other tumor sources, and neurological infections or inflammatory conditions. odulators of Lf-R activity or expression can be used to treat non-CNS (ie., non-BBB delimited) diseases, such as cancers, diseases and conditions of non-CNS organs.

Once a potential therapeutic agent has been identified from among the test compounds, those skilled in the art are familiar with the basic pharmacological steps required to develop an acceptable human or animal therapeutic agent. For example, therapeutic doses can be derived from animal studies and human clinical trials, as can suitable pharmacological carriers and excipients.

F. Therapeutic and Diagnostic Uses of MTf-R Proteins/Polypeptides

In another embodiment of the instant invention, a method is provided for administering a MTf-R protein, or a fragment thereof, to an animal in need thereof, to effect a therapeutic or prophylactic result. In vivo an MTf-R protein or fragment thereof will bind to MTf and effectively reduce the circulating concentration of MTf. This treatment is useful in diseases where increased levels of MTf are known to be implicated in disease progression, particularly, Alzheimer's Disease (see, Kennard, et al., Nat. Med., 2:1230-1235 (1996); U.S. Pat. No. 5,981,194). As a diagnostic tool, administration of an MTf-R protein or a fragment thereof, labeled with a detectable label, will identify the location or amount of MTf in the subject. Such a tool would be particularly useful for finding tumor cells that are known to express higher levels of MTf. Presumably, labeling of MTf-R with a strong beta emitting particle, such as certain Iodine or Yttrium isotopes, would assist in killing tumor cells to which the MTf-R would bind.

Other therapeutical targets relate to HIV infection as a TAT receptor, activation of the NMDA receptor with respect to synaptic plasticity, Alzheimer's disease as LRP is a receptor for APoE, alpha2-macroglobulin, APP which have all been linked to this disease; and in the regulation of lipid degrading lysosomal enzymes (SAP-dependent).

G. MTf-R Antibodies

Antibodies that specifically recognize one or more epitopes of MTf-R, or epitopes of conserved variants of MTf-R, or peptide fragments of MTf-R are also encompassed by the invention. Such antibodies include, but are not limited to, polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above.

The antibodies of the invention can be used, for example, in conjunction with compound screening assays, as described above, for the evaluation of the effect of test compounds on expression and/or activity of the MTf-R gene product. Additionally, such antibodies can be used in conjunction with gene therapy techniques to, for example, evaluate the success of transfection of normal and/or engineered MTf-R-expression. Such antibodies can be used as antagonists of MTf-R biological activity, and can additionally be used as a method for the inhibition of abnormal MTf-R activity. Thus, such antibodies can be utilized as therapeutic agents according to this invention.

The MTf-R antibodies of the invention can also be used in diagnostic techniques to identify the location, quantity, behavior and/or the like of MTf-R in an animal.

For the production of antibodies, various host animals may be immunized by injection with the MTf-R, a MTf-R protein or peptide (e.g., one corresponding to a functional domain of the receptor), truncated MTf-R polypeptides (MTf-R in which one or more domains has been deleted), functional equivalents of the MTf-R or mutants of the MTf-R. Such host animals include, but are not limited to, rabbits, mice, and rats, to name but a few. Various adjuvants can be used to increase the immunological response, depending on the host species including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacille Calmette-Guerin) and *Corynebacterium parvum*. Polyclonal antibodies are heterogeneous populations of antibody molecules derived from the sera of the immunized animals.

H. MTf-R Antisense Oligonucleotides and Ribozymes

The present invention also encompasses the use of antisense oligonucleotide sequences having sequences specific for hybridization to the MTf-R (e.g., LRP1 or LRP1B) mRNA or precursor RNA, i.e., sequences that specifically or selectively hybridize to MTf-R or mRNA or precursor RNA. Those skilled in the art can readily identify suitable antisense oligonucleotide sequences based on the known MTf-R mRNA sequence referenced above. Those skilled in the art are aware of modifications to the chemistry of oligonucleotides that improve their clinical utility, such as phosphorothioate modifications. MTf-R antisense oligonucleotides are an example of compounds that can be used to modulate MTf-R expression and, in particular, to down-regulate such expression. Those skilled in the art are also able to design ribozymes which achieve similar objectives. Methods of delivering such nucleic acids are described below.

I. MTf-R Gene Therapy

Certain embodiments of the invention employ the use of the MTf-R gene in a gene therapy method. The object of such intervention is to deliver a functional copy of the MTf-R gene to a cell in need thereof in order to increase the transcription and subsequent translation and expression of the MTf-R protein in the cell. Those skilled in the art are familiar with viral, non-viral (ie., lipid based), naked DNA and polymeric methods of delivering gene therapy vectors that include the MTf-R gene. Such methods can employ in vivo or ex vivo gene therapy techniques known to and used by those of skill in the art.

J. Diagnosis of Neurological Diseases

The present invention also relates to the diagnosis of a neurological disease comprising detecting the amount or activity of MTf-R expressed at the BBB, in neural tissue or in any tissue associated with a non-CNS target organ, such as the lung, liver, kidney, spleen, etc. The diagnostic method employs a diagnostic agent comprising an agent specific for MTf-R (i.e., an MTf-R antibody, a ligand such as MTf or Lf, or another ligand which specifically binds MTf-R) and a detectable conjugate or label (i.e., radioisotopes of technetium or iodine). Those skilled in the art can identify diseases or conditions for which the determination of MTf-R amount or localization is relevant. Most preferred are diseases or conditions, such as Alzheimer's Disease, in which MTf-R is directly implicated as a result of the present invention.

K. Binding of Different Ligands to LDL-R Receptor Family Members.

A large number of ligands have been found to bind to members of the LDL-R receptor family. These ligands and their receptor are indicated in Tables 1-3.

TABLE 1

Lipoproteins and apolipoproteins

| Ligands | LDL-R | LRP | Megalin | VLDL-R | ER-2 | LR11 |
|---|---|---|---|---|---|---|
| β-VLDL | Yes | Yes | Yes | Yes | Yes | Yes |
| Chylomicron remnants | Yes | Yes |  | Yes |  |  |
| IDL | Yes |  |  | Yes |  |  |
| Lp(a) |  |  |  | Yes |  |  |
| VLDL | Yes |  |  | Yes | Yes |  |
| ApoB100 | Yes |  | Yes |  |  |  |
| ApoE | Yes | Yes | Yes | Yes | Yes | Yes |

TABLE 2

Protease inhibitors and protease/inhibitor complexes.

| Ligands | LDL-R | LRP | Megalin | VLDL-R | ER-2 | LR11 |
|---|---|---|---|---|---|---|
| PAI-1 |  | Yes | Yes |  |  |  |
| Plasminogen |  |  | Yes |  |  |  |
| Pro-uPA |  | Yes | Yes | Yes |  |  |
| Tissue factor inhibitor |  | Yes |  |  |  |  |
| tPA |  | Yes | Yes |  |  |  |
| activated α2-macroglobulin |  | Yes | No |  |  |  |
| α1-chymotrypsin/ cathepsin G |  | No | Yes |  |  |  |

TABLE 3

Other ligands.

| Ligands | LDL-R | LRP | Megalin | VLDL-R | ER-2 | LR11 |
|---|---|---|---|---|---|---|
| Albumin |  |  | Yes |  |  |  |
| ApoJ/clusterin |  |  | Yes |  |  |  |
| ApoJ/β-amyloid |  | No | Yes |  |  |  |
| β-APP |  | Yes |  | Yes |  |  |
| Lactoferrin |  | Yes | Yes |  |  |  |
| RAP | Yes | Yes | Yes | Yes |  |  |
| Thyroglobulin |  |  | Yes |  | Yes | Yes |
| Circumsporozite protein |  |  | Yes | Yes |  |  |
| Saposin |  | Yes |  |  |  |  |
| Gentamycin |  | Yes | Yes |  |  |  |
| Polymixin B |  | Yes | Yes |  |  |  |
| Pseudomonas Exotoxin A |  | Yes | No |  |  |  |
| Seminal Vesicle Secretory Protein A |  | Yes | Yes |  |  |  |
| Thrombospondin -1 |  | Yes |  | Yes |  |  |

L. Active Agents

Active agents according to the invention include agents that affect any biological process. The term "drug" or "therapeutic agent" refers to an active agent that has a pharmacological activity or benefits health when administered in a therapeutically effective amount. Examples of drugs or therapeutic agents include substances that are used in the prevention, diagnosis, alleviation, treatment or cure of a disease or condition.

The active agent conjugated to the p97 protein or fragment or LRP1 modulator or LRP ligand may be any molecule, as well as any binding portion or fragment thereof, that is capable of modulating a biological process in a living host. Generally, the active agent may be of any size, but is preferably a small organic molecule that is capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc, ion channels, transmembrane pumps, transcription factors, signaling proteins, and the like.

The active agent or drug has a hydroxy or an amino group for reacting with the isocyanate reagent or the active agent is chemically modified to introduce a hydroxy or an amino group for reacting with the isocyanate reagent.

In some embodiments, the active agent or drug will also comprise a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

The conjugate can comprise one or more active agents linked to the same biopolymer. For example, conjugation reactions may conjugate from 1 to 5, about 5, about 1-10, about 5 to 10, about 10-20, about 20-30, or 30 or more molecules of an active agent to the biopolymer. These formulations can be employed as mixtures, or they may be purified into specific (mol:mol) formulations. Those skilled in the art are able to determine which format and which mol:mol ratio is preferred. Further, more than one type of active agent may be linked to the biopolymer where delivery of more than one type of an agent to a target site or compartment is desired. A plurality of active agent species may be attached to the same biopolymers such as adriamycin-cisplatinum conjugate compositions where the biopolymer is a p97 related protein. Thus, the conjugates may consist of a range of mol:mol ratios and incorporate more than one type of active agent. These, too, may be separated into purified mixtures or they may be employed in aggregate. Active agents include those identified U.S. Pat. No. 6,372,712 which is incorporated herein by reference.

Specific drugs of interest from which the drug moiety may be derived include, but are not limited to: psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinedionesa, succinimidesa, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines ($H_1$-antagonists, $H_2$-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antianhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidianheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. A strong beta emitting particle, such as certain iodine or yttrium isotopes, would assist in killing tumor cells.

Antibiotics, such as: aminoglycosidesa, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta.-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g. apicycline, chlortetracycline, clomocycline, etc.; synthetic antibacterial agents, such as 2,4-diaminopyrimidines, nitrofurans, quinolones and analogs thereof, sulfonamides, sulfones;

Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g;, bifonazole, butoconazole, chlordantoin, chlormidazole, etc., thiocarbamates, e.g., tolciclate, triazoles, e.g., fluconazole, itraconazole, terconazole;

Anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Antimalarials, such as: acedapsone, amodiaquin, arteether, artemether, artemisinin, artesunate, atovaquone, bebeerine, berberine, chirata, chlorguanide, chloroquine, chlorproguanil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Antiprotozoan agents, such as: acranil, tinidazole, ipronidazole, ethylstibamine, pentamidine, acetarsone, aminitrozole, anisomycin, nifuratel, tinidazole, benzidazole, suramin, and the like.

Drug compounds of interest from which drug moieties may be derived are also listed in: Goodman & Gilman's, The Pharmacological Basis of Therapeutics (9th Ed) (Goodman et al. eds) (McGraw-Hill) (1996); and 1999 Physician's Desk Reference (1998).

Specific compounds of interest also include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,591,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, U.S. Pat. Nos. 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102;

the disclosures of all the above of which are herein incorporated by reference.

The drug moiety of the conjugate may be the whole compound or a binding fragment or portion thereof that retains its affinity and specificity for the target of interest while having a linkage site for covalent bonding to the presenter protein ligand or linker. The conjugates of such drugs may be used for the same disorders, diseases, and indications as the drugs themselves.

M. P97 and Modulators

In one embodiment, the active agent is conjugated to p97 or a a modulator or ligand of the LRP receptor family (e.g. LRP1, LRP1B), or is an antibody which is capable of specifically binding to p97 or the modulator, such as an antibody to p97. In a further embodiment, the agent may be a substance having therapeutic activity such as a growth factor or lymphokine, enzyme or drug. The invention also relates to a method of delivering an active agent across the blood brain barrier comprising administering such a conjugate.

In one embodiment, the p97 protein is soluble. p97 proteins as taught in U.S. Pat. No. 5,981,194 are particularly preferred. The p97 may be a human p97 protein or fragment thereof; the p97 may be from a mammal such as a mouse. Murine p97 is disclosed in WO 01/59549 A2 which is herein incorporated by reference in its entirety.

"p97" as used in the compositions of the invention, includes membrane bound p97 (i.e., p97 linked to GPI or other lipids), soluble p97, cleaved p97, analogs of p97 which are equivalents of p97 (having greater than 40%, 60%, 80%, or 90% homology at the peptide sequence level, including allelic variants of p97), human, mouse, chicken and/or rabbit p97, and derivatives, portions, or fragments thereof. p97 may be in the form of acidic or basic salts, or in neutral form. In addition, individual amino acid residues may be modified, such as by oxidation or reduction. Various substitutions, deletions, or additions may be made to the amino acid or DNA nucleic acid sequences, the net effect of which is to retain or improve upon the desired biological activity of p97. Due to code degeneracy, for example, there may be considerable variation in nucleotide sequences encoding the same amino acid sequence. As used herein, p97 also includes fragments of p97, including any portion of p97 or its biologically equivalent analogs that contain a sufficient portion of p97 and homology to the corresponding native p97 amino acid sequence to enable it to retain or improve upon the desired biological activities of p97. In other aspects, the invention is drawn to p97 conjugates which have only minor substitutions in the amino acid sequence which do not substantially affect its receptor binding or transcytosis properties.

Preferred chemotherapeutic agents for use in p97-chemotherapeutic agent conjugates of the invention include all drugs which may be useful for treating brain tumours or other neoplasia in or around the brain, either in the free form, or, if not so useful in the free form, then useful when linked to p97. Such chemotherapeutic agents include adriamycin (also known as doxorubicin), cisplatin, paclitaxel, analogs thereof, and other chemotherapeutic agents which demonstrate activity against tumours ex vivo and in vivo. Such chemotherapeutic agents also include alkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. those of skill in the art will know of other chemotherapeutic agents.

p97-chemotherapeutic agents can comprise one or more compound moieties linked to p97. For example, conjugation reactions may conjugate from 1 to 10 or more molecules of adriamycin to a single p97 molecule. Several atoms of gold or iodine can be conjugated to a single p97 polypeptide. These formulations can be employed as mixtures, or they may be purified into specific p97:compound (mol:mol) formulations. Those skilled in the art are able to determine which format and which mol:mol ratio is preferred. Further, mixtures of compounds may be linked to p97, such as the p97-adriamycin-cisplatinum composition set out in the examples. These p97-chemotherapeutic agents may consist of a range of mol:mol ratios. These, too, may be separated into purified mixtures or they may be employed in aggregate.

The compositions of the invention may also be used for delivering an agent across the blood eye barrier or blood placenta barrier The compositions of the invention may also comprise a transcytosing or endocytosing ligand of the LRP1 or LRP1B receptor conjugated to an active agent.

N. Labels

In some embodiments, the conjugate or modulator or LRP ligand according to the invention is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., $^{32}P$), fluorophores (e.g., fluorescein), electron-dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the drug, the linker or the p97 or modulator or ligand portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidases, particularly peroxidases. Fluorescent compounds, i.e., fluor ophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

O. Mehtods of Using, Pharmaceutical Compositions, and their Administration

The term "pharmaceutically acceptable carrier" encompasses any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent. Typical modes of administration are described below.

The term "effective amount" means a dosage sufficient to produce a desired result on a health condition, pathology, disease of a subject or for a diagnositic purpose. The desired result may comprise a subjective or objective improvement in the recipient of the dosage.

A "prophylactic treatment" is a treatment administered to a subject who does not exhibit signs of a disease or exhibits only early signs of a disease, wherein treatment is administered for the purpose of decreasing the risk of developing a pathology. The conjugate compounds of the invention may be given as a prophylactic treatment.

A "therapeutic treatment" is a treatment administered to a subject who exhibits signs of pathology, wherein treatment is administered for the purpose of diminishing or eliminating those pathological signs. The conjugate compounds, modulators, and ligands of the invention may be given as a prophylactic treatment or for diagnosis.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier. The term "pharmaceutical composition" indicates a composition suitable for pharmaceutical use in a subject, including an animal or human. A pharmaceutical composition generally comprises an effective amount of a conjugate, modulator, or LRP ligand or LRP1B ligand and a pharmaceutically acceptable carrier.

The conjugates, modulators, and LRP or LRP1B ligands may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates, modulators, and LRP or LRP1B ligands can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates, modulators, and LRP or LRP1B ligands can be utilized in aerosol formulation to be administered via inhalation. The compounds of the present invention can be formulated into pressurized acceptable propellants such as dichlorodifluoromethane, propane, nitrogen and the like.

Furthermore, the conjugates, modulators, and LRP or LRP1B ligands can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms of the conjugate, modulator, and LRP or LRP1B ligand for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

In practical use, the conjugate, modulator, and LRP or LRP1B ligand according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds., Mack Publishing Co., 1985). Dermal or skin patches are a preferred means for transdermal delivery of the conjugates, modulators, and LRP or LRP1B ligands of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the compounds (e.g., LRP or LRP1B ligand conjugates, LRP or LRP1B modulator conjugates, LRP or LRP1B ligand-fusion proteins, LRP or LRP1B modulators, and LRP or LRP1B ligands) according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media maybe employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active compound in these compositions may, of course, be varied and may conveniently be between about 2 percent to about 60 percent of the weight of the unit.

The conjugates, modulators, and ligands of the invention are useful for therapeutic, prophylactic and diagnostic intervention in animals, and in particular in humans. As described herein, the conjugates show preferential accumulation and/or release of the active agent in any target organ, compartment, or site depending upon the biopolymer used.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration which dilutes the conjugates, modulators, and LRP or LRP1B ligands composition into the blood stream, or at least outside of the blood-brain barrier, may be used. Preferably, the composition is administered peripherally, most preferably intravenously or by cardiac catheter. Intra-jugular and intra-carotid injections are also useful. Compositions may be administered locally or regionally, such as intra-peritoneally. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 pmol/kg to about 25 nmol/kg, and particularly preferred dosages range from 2-250 pmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiment the conjugate comprises p97. For instance, doses of p97-adriamycin comprising from 0.005 to 100 mg/kg of adriamycin are also useful in vivo. Particularly preferred is a dosage of p97-adriamycin comprising from 0.05 mg/kg to 20 mg/kg of adriamycin. Those skilled in the art can determine suitable doses for other compounds linked to p97 based on the recommended dosage used for the free form of the compound. p97 generally reduces the amount of drug needed to obtain the same effect.

The p97-conjugates, modulators, and LRP1 or LRP1B ligands of the invention are useful for therapeutic, prophylactic and diagnostic intervention in animals, and in particular in humans. As described herein, p97-compounds show preferential accumulation in the lung, liver, kidney and spleen, and that they significantly reduce delivery of the compounds to the heart. Preferred medical indications for diagnostic uses include, for example, any condition associated with a target organ of interest (e.g., lung, liver, kidney, spleen) or any condition that requires a cardiotoxic compound that would benefit by reducing its cardiotoxicity.

The subject methods find use in the treatment of a variety of different disease conditions. In certain embodiments, of particular interest is the use of the subject methods in disease conditions where an active agent or drug having desired activity has been previously identified, but in which the active agent or drug is not targeted to the target site, area or compartment. With such active agents or drugs, the subject methods can be used to enhance the therapeutic efficacy and therapeutic index of active agent or drug.

The specific disease conditions treatable by with the subject conjugates are as varied as the types of drug moieties that can be present in the conjugate. Thus, disease conditions include cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, and the like.

Treatment is meant to encompass any beneficial outcome to a subject associated with administration of a conjugate including a reduced liklihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

P. Combinatorial Chemical Libraries

Recently, attention has focused on the use of combinatorial chemical libraries to assist in the generation of new chemical compound leads. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. *J. Med. Chem.* 37(9):1233(1994)).

Preparation and screening of combinatorial chemical libraries are well known to those of skill in the art. Such combinatorial chemical libraries include, but are not limited to, benzodiazepines (U.S. Pat. No. 5,288,514), diversomers such as hydantoins, benzodiazepines and dipeptides (Hobbs et al. *PNAS* USA 90: 6909 (1993)), analogous organic syntheses of small compound libraries (Chen et al.) *J. Amer. Chem. Soc.* 116: 2661(1994), oligocarbamates (Cho, et al., *Science* 261: 1303(1993)), and/or peptidyl phosphonates (Campbell et al., *J. Org. Chem.* 59: 658(1994)), and small organic molecule libraries (see, e.g., benzodiazepines (Baum *C&EN*, January 18, page 33 (1993)), thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514), and the like.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, HewlettPackard, Palo Alto, Calif.) which mimic the manual synthetic operations performed by a chemist. Any of the above devices are suitable for use with the present invention. The nature and implementation of modifications to these devices so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

In a preferred embodiment, the combinatorial chemistry provides variants of the known native or endogenous human ligands of the LRP and LRP1B receptors as candidate ligands, modulators, and conjugates for use according to the invention.

Q. High throughput Assays of Chemical Libraries

The assays for compounds described herein are amenable to high throughput screening. Preferred assays thus detect activation of transcription (i.e., activation of mRNA production) by the test compound(s), activation of protein expression by the test compound(s), or binding to the gene product (e.g., expressed protein) by the test compound(s). The BiaCore method is one such means for rapidly screening compounds for binding activity.

High throughput assays for the presence, absence, or quantification of particular protein products or binding assays are well known to those of skill in the art. Thus, for example, U.S. Pat. No. 5,559,410 discloses high throughput screening methods for proteins, and U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

R. Conjugation and Labeling

One of ordinary skill in the art would know how to conjugate and active agent to a protein or peptide. Methods of conjugating active agents and labels to proteins are well known in the art. See, for instance, U.S. Pat. No. 5,981,194. Many reagents and cross linkers can be used to prepare bioconjugates of an active agent and a biopolymer. See, for instance, Hermanson, G T et al. *Bioconiugate Techniques*. Academic Press, (1996).

Production of Chimeric Proteins

The chimeric protein of the present invention can be produced using host cells expressing a single nucleic acid encoding the entire chimeric protein or more than one nucleic acid sequence, each encoding a domain of the chimeric protein and, optionally, an amino acid or amino acids which will serve to link the domains. The chimeric proteins can also be produced by chemical synthesis.

A. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Cells which contain and express DNA or RNA encoding the chimeric protein are referred to herein as genetically modified cells. Mammalian cells which contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in co-pending patent applications U.S. Ser. No. 08/334,797, entitled "In Vivo Protein Production and Delivery System for Gene Therapy", by Richard F Selden, Douglas A. Treco and Michael W. Heartlein (filed Nov. 4, 1994); U.S. Ser. No. 08/334,455, entitled "In Vivo Production and Delivery of Erythropoietin or Insulinotropin for Gene Therapy", by Richard F Selden, Douglas A. Treco and Michael W. Heartlein (filed Nov. 4, 1994) and U.S. Ser. No. 08/231,439, entitled "Targeted Introduction of DNA Into Primary or Secondary Cells and Their Use for Gene Therapy", by Douglas A. Treco, Michael W. Heartlein and Richard F Selden (filed Apr. 20, 1994). The teachings of each of these applications are expressly incorporated herein by reference.

B. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

C. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells which express the selectable marker gene. Further amplification of the introduced DNA construct can be effected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is p97 can be identified by a sandwich enzyme immunoassay. The antibodies can be directed toward the LRP portion or the active agent portion.

EXAMPLES

The examples provide exemplary protocols for assessing transcytosis in vitro and for characterizing the interaction of p97 and MTf-R receptor modulators or ligands with the p97 receptor or the blood-brain barrier:

Example I

In Vitro Model of the Blood-Brain Barrier

A. Astrocytes. Primary cultures of mixed astrocytes were prepared from newborn rat cerebral cortex (Dehouck, et al., *Journal of Controlled Release* (1992)). Briefly, after removing the meninges, the brain tissue was forced gently through a 82 μm nylon sieve. Astrocytes were plated on six-well microplates at a concentration of $1.2 \times 10^5$ cells/ml in 2 ml of optimal culture medium (DMEM) supplemented with 10% fetal heat inactivated calf serum. The medium was changed twice a week.

B. BBCEC. Bovine brain capillary endothelial cells (BBCECs) were obtained from Cellial Technologies. The cells were cultured in the presence of DMEM medium supplemented with 10% (v/v) horse and 10% heat-inactivated calf serum, 2 mM glutamine, 50 μg/ml gentamycin, and 1 ng/ml basic fibroblast growth factor, added every other day.

C. BBB. The in vitro model of BBB was established by using a co-culture of BBCECs and astrocytes, basically as described in Dehouck, et al., *Eur. J. Pharm. Sci.*, 3:357-365 (1995); and Cecchelli, et al., *Adv. Drug Deliv. Rev.*, 36:165-178 (1999)). In this model, the luminal side corresponds to the apical or serum facing side of the blood-brain barrier. The abluminal side corresponds to the basolateral side of the BBB, i.e., the side facing the neurons. It is noted that this terminology is used throughout the specification. Prior to cell culture, plate inserts (Millicell-PC 3.0 μM; 30-mm diameter) were coated on the upper side with rat tail collagen. They were then set in the six-multiwell microplates containing the astrocytes prepared as described above, and BBCECs were plated on the upper side of the filters in 2 ml of co-culture medium. This BBCEC medium was changed three times a week. Under these conditions, differentiated BBCECs formed a confluent monolayer 7 days later. Experiments were performed between 5 and 7 days after confluence was reached. The number of cells at confluence was 400 000 cells/4.2 cm$^2$ or 90 μg of protein/4.2 cm$^2$, as evaluated by a micro-BCA assay from Pierce (Rockford, Ill.).

D. Sucrose permeability. The permeability coefficient for sucrose was measured to verify the endothelial permeability and the integrity and tightness of the BBCEC monolayers, as previously described, using uncoated filters or coated with endothelial cells. Briefly, the results were plotted as the clearance of [$^{14}$C]-sucrose (μl) as a function of time (min). The permeability coefficient (Pe) was calculated as: 1/Pe=(1/PSt−1/PSf)/filter area (4.2 cm$^2$), where PSt is the permeability× surface area of a filter of the co-culture; PSf is the permeability of a filter coated with collagen and with astrocytes plated on the bottom side of the filter.

Brain EC monolayers grown on inserts were transferred to 6-well plates containing 2 ml of Ringer/Hepes per well (basolateral compartment). Ringer/Hepes solution was composed of 150 mM NaCl, 5.2 mM KCl, 2.2 mM CaCl$_2$, 0.2 mM MgCl$_2$, 6 mM NaHCO$_3$, 5 mM Hepes, 2.8 mM Hepes, pH 7.4. In each apical chamber, the culture medium was replaced by Ringer/Hepes containing the labeled [$^{14}$C]-sucrose. At different times, inserts were placed into another well. At the end of the experiments, amounts of the radiotracers in the basolateral compartment were measured in a liquid scintillation counter. The permeability coefficient (Pe) for sucrose was calculated as previously described (Dehouck, et al., *J. Neurochem.*, 58:1790-1797 (1992)) using filters coated or noncoated with EC. At the end of the experiments, amounts of the radiotracers in the basolateral compartment were measured in a liquid scintillation counter. The results were plotted as the clearance of [$^{14}$C]-sucrose (μl) as a function of time (min). PSt=permeability×surface area of a filter of the coculture; PSf=permeability of a filter coated with collagen and astrocytes plated on the bottom side of the filter. The permeability coefficient (Pe) was calculated as:

$$\text{Clearance } (\mu l) = \frac{[C]_A \times V_A}{[C]_L} \quad \begin{aligned} &[C]_A = \text{Abluminal tracer concentration} \\ &V_A = \text{Volume of abluminal chamber} \\ &[C]_L = \text{Luminal tracer concentration} \end{aligned} \quad 1)$$

$$1/Pe = (1/PSt - 1/PSf)/\text{filter area } (4.2 \text{ cm}^2) \quad 2)$$

FIG. 1 and FIG. 2 set out control experiments.

Briefly, in FIG. 1, coated or non-coated filters with BBCE cells were transferred to 6-well plates containing 2 ml of Ringer/Hepes per well (basolateral compartment) for 2 hrs at 37° C. In each apical chamber, the culture medium was replaced by 1 ml Ringer-Hepes containing labeled [$^{14}$C]-sucrose. At different times, inserts were placed into another well. At the end of the experiments, amounts of the radiotracers in the basolateral compartment were measured in a liquid scintillation counter. The difference in the slopes for PSf and PSt demonstrates that the monolayer of cells provides significant resistance to sucrose permeability, thus confirming the presence of tight junctions between cells regardless of pre-incubation.

In FIG. 2, 1 micromolar p97 protein (provided by Synapse Technologies Inc, Vancouver, Canada) was added to the luminal side to determine its effect on sucrose permeability. Sucrose permeability in the absence of p97 was 1.21×10-3 cm/min, whereas in the presence of p97 sucrose permeability was 1.35×10-3 cm/min. The results show that there was no significant change in sucrose permeability. A control experiment in the absence of cells demonstrates the relative effectiveness of the BBB model compared to the filter alone.

In FIGS. 1 and 2, Psf and Pst refer to flow rates through the membrane with and without cells. They are used to calculate the permeability of the membrane with cells. Definitions for Psf and Pst are in found in *J. Neurochem.*, 58:1790-97 (1992), the teachings of which are incorporated by reference. The definition of PSt and PSf are simply the slope of the clearance curves for the co-culture and for the control filter respectively. The PS value for the endothelial monolayer alone is defined as PSe where:

$$1/PSe = 1/PSt - 1/PSf$$

Permeability of the endothelial monolayer alone is defined as Pe where:

$$Pe = PSe/A, \text{ wherein A is the area of the membrane.}$$

Example II

Binding of p97 with BBCECs and Rat Brain Endothelial Cells

B. Binding studies of p97. Binding of p97 was performed with BBCECs and Rat Brain Endothelial Cells that were pre-incubated 2 hrs in Ringer/Hepes to avoid any interference from the astrocytes.

FIG. 3 demonstrates the competitive binding of p97 with cold p97, transferrin and lactoferrin. For the binding experiments, cells were incubated for 2 h at 4° C. in Ringer/Hepes in the presence of [$^{125}$I]-p97 (25 nM) and increasing concentrations of cold-p97 or high (7.5 micromolar) concentrations of transferrin or lactoferrin. At the end of the incubation, the filters were gently washed at 4° C. three times with 4 ml of cold-PBS. Then the associated radioactivity of endothelial cells was determined by removing the membrane of the culture insert and counting it in a gamma counter.

The results of FIG. 3 demonstrate that [$^{125}$I]-p97 binding to the BBCECs was competitively inhibited by cold-p97 and by lactoferrin, but significantly, transferrin did not block or reduce the binding of [$^{125}$I]-p97 to its receptor on the BBCECs. This data establishes for the first time that [$^{125}$I]-p97 is not binding to the transferrin receptor (Tf-R) as previously hypothesized.

C. Binding of p97 in Rat Brain Endothelial Cells.

As with FIG. 3, FIG. 4 demonstrates a comparative study, but this time using Rat Brain Endothelial-4 cells (RBE4 supplied commercially by ATCC). RBE4 cells were grown in monolayers in 24 wells plastic tissue culture flasks at 37° C. under 5% $CO_2$ in minimum essential medium Alpha and Ham's F10 (1:1) supplemented with 10% heat inactivated fetal bovine serum. For p97 binding experiments, RBE4 cells were pre-incubated at 37° C. for 2 hrs in Ringer/Hepes. $^{125}$I-p97 in 200 µl of Ringer/Hepes was added to RBE4 cells for 2 hrs at 4° C. in the presence or absence of high concentration of cold-p97, human holo-transferrin or human lactoferrin. After the incubation, the cells were washed 4 times with PBS and the $^{125}$I-p97 associated with the cells was measured.

FIG. 4 demonstrates that cold p97 (10 micromolar) and lactoferrin (10 micromolar) both competitively inhibit [$^{125}$I]-p97 binding to RBE4 cells, whereas transferrin (10 micromolar) does not.

Example III

Interaction of p97 with Human Brain Capillaries

A. Isolation of human brain capillaries. Capillaries of the blood-brain barrier were isolated from human brain cortex by a procedure previously described by Dallaire, et al., *J. Biol. Chem.*, 267:22323-22327 (1992) with slight modifications. Human brains were obtained post-mortem. The brain was cleared of meninges, superficial large blood vessels and choroid plexus. All the following procedures were performed at 4° C. The cerebral cortex was homogenized in 5 volumes of Ringer/Hepes solution with a Polytron (Brinkman Instruments, Rexdale, Ontario, Canada). The homogenate was mixed with an equal volume of Dextran T-70 (27 g in 100 ml of Ringer/Hepes). The suspension was centrifuged at 25,000 g for 10 min. The pellet was resuspended in 30 ml of Ringer/Hepes and passed through a 250 µm nylon mesh screen. The nylon mesh was rinsed and the filtrate was concentrated by centrifugation at 25,000 g for 10 min. The pellet was resuspended in 30 ml of cold-Ringer/Hepes and passed through a 2.5 cm×4.0 cm glass beads column [40/60-mesh (0.25 mm) glass beads]. The columns were washed twice with 25 ml of Ringer/Hepes. The glass beads were transferred to a beaker and swirled vigorously (15 min at 4° C.) in Ringer/Hepes to separate the microvessels from the beads. The beads were allowed to settle and the supernatant was decanted and kept at 4° C. The beads were swirled for another 15 min in Ringer/Hepes. The supernatants were pooled and the microvessels were collected by centrifugation at 25,000 g for 10 min. Brain capillaries were kept at −80° C. until used.

B. p97 accumulation in human brain capillaries. A rapid filtration technique was used to measure the accumulation of [$^{125}$I]-p97 in human brain capillaries. Accumulation of [$^{125}$I]-$p_{97}$ was measured at 37° C. for 1 h in isolated human brain capillaries (100 µg/assay). The incubation medium contained [$^{125}$I]-p97 and a final concentration of 100 nM p97 in Ringer/Hepes solution. The accumulation of [$^{125}$I]-p97 was performed in presence or in absence of 5 µM of cold-p97, holo-transferrin or lactoferrin. After incubation, the accumulation was stopped by addition of 1 ml-cold stop solution (150 mM KCl, 0.1% BSA and 5 mM Hepes, pH 7.5). The suspension was filtered under vacuum through a 0.45 µM pore size Millipore filter. The filter was rinsed with 8 ml of stop solution, and the radioactivity was counted. Nonspecific binding of the radioactivity to the capillaries was determined by the addition of the ice-cold stop solution to the capillaries before adding the incubation medium. This value was subtracted from accumulation values obtained following an 1 h incubation. The results were expressed as ng of [$^{125}$I]-p97 accumulated per µg of brain capillaries.

FIG. 5 demonstrates the results of the experiments. Consistent with the findings in FIGS. 3 and 4, it is found that cold p97 (5 micromolar) or lactoferrin (5 micromolar) significantly inhibits competitive [$^{125}$I]-p97 binding to human brain capillary cells, whereas transferrin (5 micromolar) shows no significant competition. This finding confirms that p97 binding to its receptor is not blocked by transferrin.

FIG. 6 is a repeat experiment, performed identically to the experiment of FIG. 5, except this time with the additional competition assay for β-amyloid peptide. Evidently, the β-amyloid peptide 1-40 competes with p97 for receptor binding, along with lactoferrin, but not with transferrin. This finding indicates that the receptor responsible for the p97 binding and transport across the BBB is RAGE and/or LRP1.

FIG. 7 shows the results of experiments where the ligands p97, Lf and Tf were heated or not heated prior to the binding study. In all cases, binding experiments were conducted in the transwell apparatus as described previously, with the exception that binding was conducted at either 4° C. or at 37° C. For the 37° C. trial, a separate experiment was conducted where the ligand was boiled for 30 mins then rapidly cooled prior to administration on the transwell plates. Results demonstrate that the heat denatured p97 protein had a significantly lower accumulation in the cell monolayer compared to normal p97; although both forms at 37° C. bound to a higher degree than at 4° C. Similarly, heat denatured Lf had significantly lower accumulation in the BBB model cells than its natural counterpart. Transferrin itself had very little accumulation to speak of.

In FIG. 7, it is important to clarify the overall striking difference in accumulation of Lf and p97, as Lf is almost twice as high at the end of the experiment. It must be remembered that p97 is being substantially transcytosed through the BBB model cells and secreted into the abluminal region, whereas Lf is not. This effect leads to the incorrect conclusion that Lf may be taken into the BBB at a higher rate than p97.

Example IV

Transcytosis of p97

Transcytosis experiments were performed as follows. One insert covered with BBCECs was set into a transwell apparatus containing a six-well microplate with 2 ml of Ringer/Hepes and pre-incubated for 2 h at 37° C. Plates were slowly adjusted to the indicated temperatures (4° C. or 37° C.). [$^{125}$I]-p97 (250 nM) was added to the upper side of the filter covered with cells. At various times, the insert was transferred to another well to avoid a possible reendocytosis of p97 by the abluminal side of the BBCECs. At the end of experiment, [$^{125}$I]-p97 was assessed in 500 µl of the lower chamber of well by TCA precipitation. p97 was also measured in 50 µl of the lower chamber of the well by Western blots using mAb L235.

FIG. 8 demonstrates that p97 transcytosis was significantly higher at 37° C. than at 4° C. This result demonstrates that p97 is actively transported in an energy dependent process across this blood-brain barrier model in a temperature dependent fashion, presumably by receptor mediated uptake.

FIG. 9 confirms that transcytosis of p97 is also a saturable phenomenon, thus further implicating a specific MTf-receptor protein in this model of the blood-brain barrier. These experiments were conducted as previously described. Measurements of the amount of transcytosis were made at the time points indicated.

The effect of potentially competitive ligands on transcytosis was assessed in a series of experiments. In FIG. 10a, transcytosis of $^{125}$I-p97 was compared in the presence of cold p97 (5 micromolar), Lf (5 micromolar), and Tf (5 micromolar). At these concentrations, only the cold p97 successfully reduced transcytosis of the labelled p97. In FIG. 10b, β-amyloid protein (5 micromolar) also failed to slow or reduce transcytosis of labelled p97. Higher amounts of ligands do interfere with p97 transcytosis (data not shown). In FIG. 10c, RAP, a known polypeptide inhibitor of the LDL-Receptor family was applied to the cells (25 micrograms/ml). RAP significantly inhibited the transcytosis of p97, thus directly implicating the LDL-receptor family, especially LRP1 as the MTf-R.

Example V

Accumulation and Transcytosis of p97 in Brain

A. Brain uptake and in situ brain perfusion. To measure the brain uptake of [$^{125}$I]-p97, mice were each given approximately 4 pmol of [$^{125}$I]-p97, [$^{125}$I]-BSA or human [$^{125}$I]-holo-transferrin in 200 µl of injection solution through the jugular vein. After 1 hour, animals were sacrificed and perfused with buffer via cardiac aorta. The serum and brain samples were collected and the levels of radioactivity were measured. In situ brain perfusion was performed as previously described (Dagenais, C., Rousselle, C., Pollack, G. M. & Scherrmann, J. M. *J. Cereb. Blood Flow Metab.* 20: 381-386 (2000)). Briefly, the right hemisphere of the brain was perfused with 10 nM of [$^{125}$I]-p97 or [$^{125}$I]-holotransferrin in Krebs-bicarbonate buffer (pH 7.4 with 95% O 2 and 5% CO 2 at a flow rate of 2.5 ml/min for 10 min) via a catheter inserted in the right common carotid artery following ligation of the external branch. Mice were decapitated to terminate perfusion and the right hemisphere was isolated on ice before subjected to capillary depletion (Triguero, D., Buciak, J. & Pardridge, W. M. *J Neurochem.*, 54: 1882-1888 (1990)). Aliquots of homogenates, supernatants, pellets and perfusates were taken to measure their contents in [$^{125}$I]-proteins by TCA precipitation and to evaluate their apparent $V_D$.

B. Iodination of proteins. p97, bovine holo-transferrin and bovine lactoferrin were iodinated with standard procedures using iodo-beads from Sigma. Bovine holo-transferrin and bovine lactoferrin were diluted in 0.1M phosphate buffer, pH 6.5 (PB). p97 obtained from Synapse Technologies in neutralized citrate at pH 7.0 was dialyzed against this PB. Two iodo-beads were used for each protein. These beads were washed twice with 3 ml of PB on a Whatman filter and resuspended in 60 µl of PB. $^{125}$I (1 mCi) from Amersham-Pharmacia biotech was added to the bead suspension for 5 min at room temperature. The iodination for each protein was initiated by the addition of 100 µg (80-100 µl). After an incubation of 10 min at room temperature. The supernatants were applied on a desalting column prepacked with 5 ml of cross-linked dextran from Pierce and $^{125}$I-proteins were eluted with 10 ml of PBS. Fractions of 0.5 ml were collected, and the radioactivity in 5 µl of each fraction was measured. Fractions corresponding to $^{125}$I-proteins were pooled and dialyzed against Ringer/Hepes, pH 7.4. The efficiency of radiolabeling was between 0.6-1×10$^8$ cpm/100 µg of protein.

Transcytosis and binding experiments. One insert covered with BBCECs was set into a six-well microplate with 2 ml of Ringer-Hepes and was pre-incubated for 2 h at 37° C. [$^{125}$I]-p97 was then added to the upper side of the insert. At various times, the insert was sequentially transferred into a fresh well to avoid possible reendocytosis of p97 by the abluminal side of the BBCECs. At the end of the experiment, [$^{125}$I]-p97was quantitated in 500 µl of the lower , chamber of each well by TCA precipitation. We also measured p97 in 50 µl of the lower chamber of each well by SDS-PAGE according to the method of Laemmli (Laemmli, U.K. *Nature;* 227: 680-685 (1970)). Proteins were separated on 7.5% acrylamide gels, stained with Coomassie Blue, dried and analysed by densitometry. For the binding experiments, cells were treated with or without saponin (0.5% wt/vol) to permeabilize cellular membranes as perviously described (Descamps, L., Dehouck, M. P., Torpier, G. & Cecchelli, R. *Am. J. Physiol.* 270: H1149-H1158 (1996)). After 2 hrs at 4° C., ECs were gently washed, and the [$^{125}$I]-p97 attached to the ECs was quantified in a liquid scintillation counter.

p97 accumulation in human brain capillaries. Human brain capillaries were isolated by a procedure previously described (see Dallaire, L., Tremblay, L. & Beliveau, R. *Biochem. J.* 276: 745-752 (1991), Demeule, M. et al. *Int. J. Cancer.* 93: 62-66 (2001)). [$^{125}$I]-p97 was incubated with capillaries (100 µg) in Ringer/Hepes solution in the presence or absence of unlabelled p97, holo-transferrin or lactoferrin. The uptake was stopped by the addition of ice-cold stop solution (150 mM KCl, 0.1% bovine serum albumin (BSA) and 5 mM Hepes, pH 7.5) and the suspension was filtered under vacuum through a 0.45 µM pore size Millipore filter. The filter was rinsed with 8 ml of stop solution, and the radioactivity was assayed. Nonspecific binding of radioactivity to the capillaries was determined by addition of the ice-cold stop solution to the capillaries before adding the incubation medium. This value was subtracted from the values obtained following a 1 h incubation.

Example VI

Exemplary Methods

Cell culture. Cells were grown in monolayer at 37° C. under 5% CO2 in DMEM supplemented with 10% fetal heat inactivated calf serum (normal astrocytes); DMEM high glucose, 1 mM sodium pyruvate supplemented with 10% calf serum (CTX); DMEM high glucose supplemented with 10% calf serum (RG2); RPMI-1640 supplemented with 10% calf serum and 2 mM glutamine (CNS-1); Ham's F12 supplemented with 10% calf serum (C6); MEM, 1 mM sodium pyruvate supplemented with 10% calf serum (U-87, U-138).

Uptake of [$^{125}$I]-p97. Cells were grown in monolayer in six-multiwell microplates at 37° C. under 5% CO2. Uptake of [$^{125}$I]-p97 was measured at 37° C. for 2 h in astrocytes and astrocytomas. The incubation medium contained [$^{125}$I]-p97 and a final concentration of 50 nM P97 in Ringer/Hepes solution. The uptake of [$^{125}$I]-p97 was performed in presence or in absence of 5 µM cold-P97. After incubation, the cell monolayer was wash three times with cold Ringer/Hepes solution. Triton X-100 0.1% was added and the [$^{125}$I]-p97 uptake was assessed in the Triton X-100 soluble fraction by TCA precipitation.

RNA extraction. Cells in six-wells plate or in 75 cm$^2$ plastic tissue culture flasks were grown at 37° C. under 5% CO2 with optimal culture medium to 80-90% confluence. Total cellular RNA was preserved in Trizol (Gibco BRL, Burlington, ON). The solution are frozen at −80° C. until extraction. The solution was defroze and mixed with 5:1 chloroform for 3 minutes at room temperature. The suspension was centrifugated at 12000 g at 4° C. The clear supernatant was collected then mixed with 1:1 of isopropanol for 15 minutes at room temperature. The mix was centrifugated at 12000×g for 10 min at 4° C. The pellets was washed with 70% ethanol and dried before resuspended in RNase Free H2O.

RT-PCR. RT-PCR was performed for members of the LDL-R family: LRP, LRP1B, megalin, LDL, VLDL, LRP8, LR11, RAP, LR3, cubulin and P97. DNA (cDNA) synthesis was performed with 1 (g of total RNA using a cDNA one step synthesis kit (Invitrogen, USA) following the manufacturer's protocol. (1× of reaction mix, RNA 1 (g, 0.2 (M of both primers, 1 (l of RT/Platinum Taq mix). The cDNA generated was amplified using primers produced with MacVector 7.0 (Oxford molecular Ltd, Oxford, UK). All the subsequent assays were then performed under conditions that produced amplifications of cDNA within a linear range. RT inverse-transcription was performed at 50° C. for 30 min. PCR amplification for 35 cycles for all was performed as follows: denaturation at 94° C. for 30 s, annealing at 60° C. for 30 s and extension at 72° C. for 30 s. Finalisation stage was performed at 72° C. for 30 min. Tubes containing all the ingredients except templates were included in all runs and served as negative controls. The amplified PCR products were electrophoresed on a 2% agarose gel in TAE (40 mM Tris, 360 mM acetic acid, 1 mM EDTA, 12.5 fM Ethium bromide) and were visualized under ultraviolet light followed by densitometric analysis.

Western blot. Cell lysates (25 µg of protein) were subjected to SDS-PAGE and electroblotted onto PVDF membranes. Membranes were blocked over night at 4° C. in 5% non fat dry milk in TBS (NaCl 125 mM, Tris 20 mM, pH 7.5) with 0.1% Tween. Successive incubations with proper primary antibody and horseradish peroxidase-conjugated secondary antibody were carried out for 60 min at room temperature. All incubations with antibodies were done after 3×15 minutes washes with TBS-Tween 0.1% The immunoreactive proteins were detected using the ECL system (Amersham-Pharmacia, Baie d'Urfé, Que).

Ligand-binding. Briefly, cells were incubated with [$^{125}$I]-p97 in Ringer/Hepes solution, in presence or in absence of 5 µM cold-P97 for 1 h at 4° C. After incubation, the cell monolayer was washed three times with cold Ringer/Hepes solution. After the ligand binding at 4° C., cell monolayer was washed three times with cold Ringer/Hepes solution and was incubated with DSS (Disuccinimidyl suberate) or Lomant's reagent DSP (Dithiobis(succinimidyl propionate)) from Pierce. After t he cross-link, cells were lysed and proteins were separated by SDS-PAGE electrophoresis. Gels were fixed, dryed and exposed to Kodak films at −80° C. for about 3 weeks before developping. The cross-link was performed exactly as the manufacturer's protocol.

BIAcore analysis. MAb L235 was covalently coupled to a CM5 sensor chip via primary amine groups using the N-hydroxysuccinimide (NHS) /N-ethyl-N'-(dimethylaminopropyl)carbodiimide (EDC) coupling agent as previously described (Johnsson, B., Lofas, S., & Lindquist, G. *Anal. Biochem.* 198: 268-277 (1991)).

Briefly, the carboxymethylated dextran was first activated with 50 µl of NHS/EDC (50 mM/200 mM) at a flow rate of 5 µl/min. The mAb L235 (5 µg) in 10 mM acetate buffer, pH 4.0 was then injected and the unreacted NHS-esters were deactivated with 35 µl of 1 M ethanolamine hydrochloride, pH 8.5. Approximately 8000 to 10000 relative units of mAb 235 were immobilized on the sensor chip surface. The Ringer/Hepes buffer was used as the eluent buffer to monitor the signal plasmon resonance (SPR). p97 diluted in the same eluent buffer was boiled for various lengths of time, cooled to room temperature and injected onto the sensor chip surface. The SPR obtained was compared to that of unboiled p97.

The brain uptake of human [$^{125}$I]-p97 in mice, one hour after i.v. injection was evaluated and and compared to that obtained for [$^{125}$I]-BSA or human [$^{125}$I]-transferrin (FIG. 11a). The brain/serum ratio for p97, BSA and holo-transferrin is respectively 0.025, 0.002 and 0.008 indicating a higher brain accumulation for p97. To determine whether this observation is related to a greater brain penetration, we measured the apparent volume of distribution ($V_D$) of p97 and transferrin by in situ brain perfusion in mice (FIG. 11b). After a 10 min perfusion, the apparent $V_D$ for both proteins was calculated for the whole brain homogenates as well as for brain capillaries and brain parenchyma. Under these conditions the apparent $V_D$ of transferrin in the brain parenchyma is 2.4 ml/100 g which is slightly higher than the brain $V_D$ for the vascular marker [$^{14}$C]-inulin at 1.7 ml/100 g (data not shown). Importantly, the apparent $V_D$ of p97 in the brain parenchyma is 17.2 ml/100 g, 8.8-fold higher than for transferrin, indicating a greater passage through brain capillaries. To further investigate the transport of p97 across the BBB, the passage of [$^{125}$I-p97 across an in vitro model of the BBB was measured at 37° C. and at 4° C. (FIG. 11c). A dramatic reduction in the transport from the apical to the basolateral surface of BBCEC monolayers of [$^{125}$I-p97 is observed at 4° C., indicating that the transcytosis of p97 requires an active mechanism.

Transcytosis of [$^{125}$I-p97 at 37° C. was measured both in the apical-to-basolateral direction and in the basolateral-to-apical direction across BBCEC monolayers to ascertain any vectorial transport of p97 (FIG. 11d). This figure demonstrates that p97 transport in the BBCEC model is highly vectorial. In this experiment, [$^{125}$I-p97 (25 nM) was added to the luminal or abluminal side of the BBCECs. After 2 hours of incubation at 37° C., the amount on the opposing side of the membrane was measured. Results demonstrate that p97 transport is substantially directed from the luminal to the abluminal side, corresponding in vivo to the delivery of p97 from the blood/serum face of brain capillaries (i.e., inside the capillaries) to the neural cells of the brain. After 2 hrs, [$^{125}$I-p97 transport is about 3-fold higher when measured in the apical-to-basolateral direction, indicating a substantial preferential transport of p97 towards the brain.

Localization and Saturability of the p97 Binding Activity.

To assess the presence and extent of intracellular p97 binding sites, BBCECs were treated with saponin (FIG. 12a). The saponin permeabilization of ECs increased the amount of [$^{125}$I]-p97 associated with BBCECs 4-fold. Moreover, the binding of [$^{125}$I]-p97 after saponin treatment decreased in the presence of unlabelled p97 (FIG. 12b). A 200-fold molar excess of unlabelled p97 inhibited radiolabel binding by approximately 50%, showing that much of the interaction of p97 with ECs is saturable.

Values for specific p97 binding were calculated by subtracting the non-specific binding of p97 measured in the presence of a high concentration of unlabelled p97 and are expressed in a Scatchard plot (FIG. 12c). Analysis of this plot is consistent with a single-binding site for p97 with a Kd of about 1 µM and 4×106 sites/cell.

Comparison of p97, transferrin and lactoferrin binding on BBCEC monolayers.

|  | Kd (nM) | Number of binding sites/cells |
| --- | --- | --- |
| P97 (+saponin) | 1400 | 6 000 000 |
| Transferrin (+saponin) | 11 | 35 000 |
| Lactoferrin (−saponin) |  |  |
| Site 1 | 35 | 35 000 |
| Site 2 | 1900 | 900 000 |

In the above table, p97 results from FIG. 12 (Kd and number of binding sites/cells) are compared to published values for transferrin and lactoferrin (see Descamps et al., Am. J. Physiol. 270:H1149-H1158, 1996; Fillebeen et al., J. Biol. Chem. 274:7011-7017, 1999).

Efficiency of p97 Transcytosis

The efficiency of p97 transcytosis was assessed by comparing the passage of both p97 and bovine holo-transferrin under identical conditions (FIG. 13a). Transport of p97 from the apical to the basolateral surface of ECs is much higher than for transferrin at 37° C. (FIG. 13a) Heat-denaturation reduced the passage of both p97 and holo-transferrin through the BBCEC monolayers, indicating that their transcytosis is conformation-dependent. As p97 is resistant to heat denaturation in Ringer/Hepes solution (FIG. 13b), it was necessary to determine the denaturing conditions. The conformation of the protein was assessed using the biological interaction analysis in real-time between p97 and the monoclonal antibody (mAb) L235, which recognizes a conformational epitope on p97 since no enzymatic activity has yet been defined for this protein. For this analytical approach, mAb L235 was immobilized on the surface of a sensor chip and exposed to native p97 as well as to p97 which had been boiled for 5, 10, 20 or 30 min. The surface plasmon resonance signal of native proteins, the accumulation of p97 in BBCE cells is 5.7 µg/cm$^2$ whereas no significant accumulation is observed for bovine transferrin. These results show that the p97 transport system has much greater capacity than has the transferrin transport system.

p97 Stability and BBCEC Monolayer Integrity Following Transendothelial Transport To examine p97 integrity after transcytosis at 37° C. and 4° C., 50 µl of the lower compartments of the wells were recovered after 30, 60, 80 and 120 min. Proteins were then separated by SDS-PAGE and visualized by gel staining (FIG. 14a). Time-dependent transcytosis of recombinant p97 is observed, with no apparent degradation. Transcytosis of this protein is much higher when the experiment is performed at 37° C. than at 4° C. The low molecular weight proteins observed at 30 min are only serum proteins remaining in the assay. Furthermore, the gels were scanned and the amount of p97 that passed through the BBCEC mono layers was evaluated using known quantities of p97 (FIG. 14b). The total amount of intact p97 after transendothelial transcytosis is 35 µg/cm$^2$, very similar to the amount shown in FIG. 13a after TCA precipitation, indicating that the iodination of p97 does not interfere with its transcytosis. Since p97 is transported much faster than is transferrin, the permeability to [$^{14}$C]-sucrose was measured in the presence of a high concentration of p97 (FIG. 14c). No significant increase in the clearance of sucrose is detectable in the presence of p97. In addition, the permeability coefficient (Pe) for sucrose in the presence of p97 is 1.04±0.15×10$_{-3}$ cm/min, not significantly different from the value of 1.07±0.19×10$_{-3}$ cm/min measured in the absence of p97 (FIG. 14d). These data indicate that the rapid passage of p97 is unrelated to changes in the integrity of BBCEC monolayers.

Effect of p97 and Transferrin on [$^{125}$I]-p97 Transcytosis

To establish whether this p97 transport is saturable, and whether it involved the transferrin receptor, apical-to-basal transport of [$^{125}$I]-p97 across BBCEC monolayers was measured in the presence of a 200-fold molar excess of p97, bovine holo-transferrin or human holo-transferrin (FIG. 15). An excess of unlabelled p97 reduced the transport of [$^{125}$I]-p97 by 69% (FIG. 15a) whereas the presence of either bovine or human holo-transfenin had no impact (FIG. 15b). This indicates that p97 transcytosis is a saturable process that does not employ the transferrin receptor. This assumption is supported by the fact that mAb OX-26, which binds to the transferrin receptor, does not significantly reduce p97 transcytosis as compared to transcytosis measured in the presence of nonspecific IgGs (FIG. 15c).

Identification of LRP as a Potential Receptor for p97

We also assessed the uptake of [$^{125}$I]-p97 into isolated human brain capillaries incubated for 1 h at 37° C. (FIG. 16a). A 50-fold molar excess of unlabelled p97 inhibited the uptake of [$^{125}$I]-p97 by 60%. Human lactoferrin caused a similar inhibition of [$^{125}$I]-p97 uptake whereas human holo-transferrin had no effect. These results indicate that LRP, which binds and transports lactoferrin across BBCEC monolayers is also involved in the uptake of [$^{125}$I]-p97 into brain capillaries and in the transcytosis of p97.

To further investigate the role of LRP in the transport of p97, transcytosis experiments were performed in the presence of the receptor-associated protein (RAP), a protein chaperone that regulates LRP (FIG. 16b). Recombinant RAP (25 µg/ml) reduced the initial rate of [$^{125}$I]-p97 transport across BBCEC monolayers by more than 50%. In addition, the transcytosis of bovine [$^{125}$I]-lactoferrin is inhibited by more than 75% by a 200-fold molar excess of unlabelled p97 (FIG. 16c).

FIG. 17 further illustrates the effect of LRP ligands RAP, Aprotinin and BSA on p97 transcystosis and the effect of p97 on lactoferrin transcytosis. The inhibition by RAP but not BSA distinguishes the p97 from megalin, the chylomicron receptor found in the liver, and the receptor for advanced glycation end products which can be found on lung endothelial cells, neurons, atrocytes, and glomeruli.

Time Course of p97 Uptake in BBCE.

The time course for the internalization of p97 is illustrated in FIG. 18 which depicts the movement of p97 at 30 minutes and 60 minutes and its accumulation in early endosome. FIG. 19 illustrates the conditions for studying the rate of p97 internalization and transcytosis in the BBB model. FIG. 20 shows the results of such a study. Transcytosis is fast as in 10 minutes, 80% of membrane bound p97 has transcytosed.

Pathway for p97 Endocytosis.

Upon binding to a LRP to a growing brain capillary endothelial cell, LDL is classically internalized by a clathrin dependent pathway wherein the LDL is directed toward lysosomes and degraded so as to provide cholesterol to the growing cell. This pathway is sensitive to filipin. In differentiated BCECs, the LDL is transcytosed. Evidence indicates the same receptor is involved in both pathways. (see Dehouck et al., *J. of Cell Biology* 138(4) 877-889 (1997).

The possibility that p97 endocytosis involved a clathrin-dependent mechanism or a clathrin independent mechanism (i.e., caveolae) was examined in BBCE. p97 was found to co-localize with clathrin much more similarly than with caveolin (data not shown). Transcellular localization of p97 and clathrin was examined in BBCE as the p97 moved from the luminal to abluminal side of the BBB model (FIG. 21). The data are indicative of a co-migration of p97 and clathrin. As a control for the effect of the Alexa label, the behavior of p97 and p97-alexa were compared. (data not shown). Although p97-alexa also labeled other vesicular structures, p97 and p97-alexa had a similar localization indicating that the label did not change the behavior of p97.

Following endocytosis, the transport fate of p97 depends upon the cell type. As shown in FIG. 22, p97 may be transported across the cell as occurs with brain endothelial cells lining the brain capillaries or else it may be transported to a lysosome. In the first instance, p97 is useful as a means of delivering therapeutic agents such as p97 therapeutic agent conjugates across the blood brain barrier. In the second instance, p97 is useful as a means of delivering therapeutic agents to the intracellular compartment, particularly the lysosome. In this instance, conjugates with enzymes (e.g., an enzyme deficient in a patient with a lysosomal storage disease) are particularly of interest.

LRP Ligands and Receptor Family Expression.

FIG. 23 illustrates an LRP receptor α and β subunits with respect to the cell membrane and some LRP ligands. FIG. 25 presents the relative amounts of LRP/LRP1B proteins in various cell types, including astrocytomas, normal astrocytes, and brain capillaries. As a contrast, the distribution of megalin among astrocytes and astrocytomas is presented in FIG. 26. As shown in FIGS. 27 and 28, the expression of LRP1B in astrocytes and astrocytomas as determined by (RT-PCR) is increased in the astrocytomas over the astrocytes. This result is result is consistant with the greater uptake of the labeled p97 by the astrocytomas. By way of contrast, and in confirmation that megalin is not involved in the p97 uptake, the pattern of megalin expression among these cells is not at all similar to the updtake pattern for p97 for these cells (see FIG. 26). FIG. 28 more clearly illustrates the correlation between p97 uptake and LRP1B expression.

FIG. 32 shows the expression of members of the LDL receptor family by RT-PCR. In glioblastoma cell line U87 LRP, LRP1b, LDL, and LRP8 are highly expressed. Cubilin and RAP are expressed to a much lesser extent. In human capillaries, LRP1B, megalin, LDL, LRP8, and LRP are highly expressed as compared to cubilin.

Association of p97 with LRP/LRP1B

FIG. 29 shows that LRP/LRP1B migrates as a high molecular weight dissociable complex in the presence of p97, indicating the association of the two molecules. Exposing the complex to reducing conditions such as β-mercaptoethanol induces the release of p97 from the high molecular weight complex (see FIG. 30). p97 similarly forms high molecular weight complexes upon contact with glioblastomas and human brain capillaries (see FIG. 31).

Effect of p97 on Cell Expression of Members of LDL-Receptor Family in Human Glioblastoma.

Figure 33:
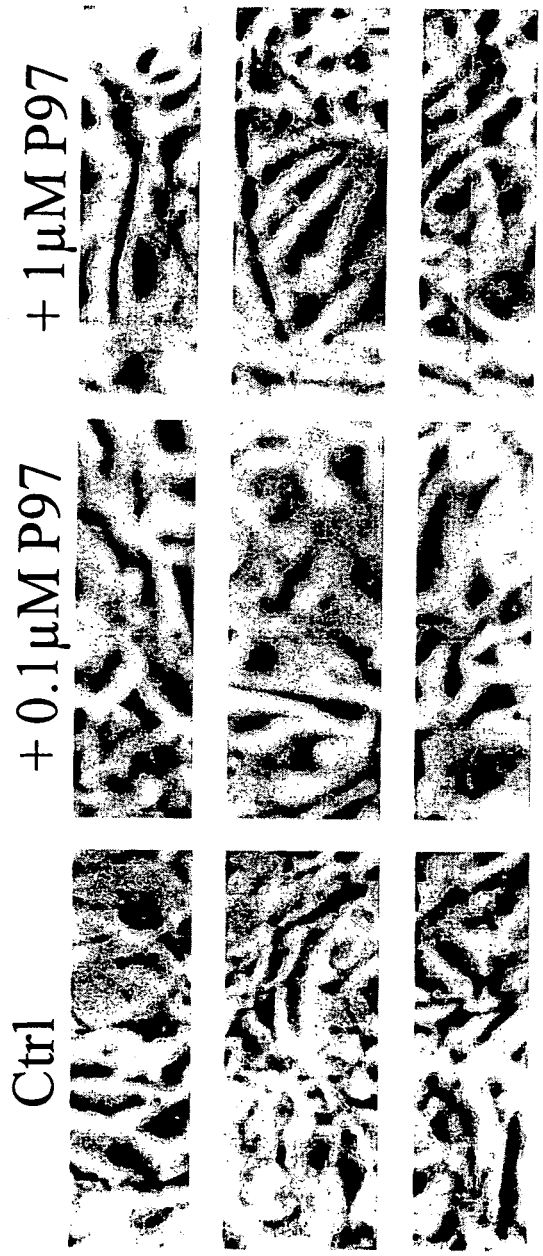

To examine the ability of p97 to be taken up by astrocytoma cells and astrocytes, cells of each type were incubated with $^{125}I$ p97. As shown in FIG. 24, the specific uptake of p97 in such cells was greatly increased in the astrocytoma cells over the astrocytes. As shown in FIG. 24, astrocytoma cells take up p97 to a much greater extent than astrocytes. This finding indicates that p97 conjugates to anticancer agents would be particularly useful in the treatment of gliomas. FIG. 34 shows the effect of p97 and RAP treatments on LRP and LRP1B expression in U87 cells. While p97 does induce the expression of LRP1B, it has no discernable effect on the morphology of the U-87 cells (see FIG. 33). FIG. 35, shows the dose response effect of p97 for LRP1Bb, LRP, LDL-R, Megalin, and Cubilin as measured by RT-PR in U-87 cells. p97 induces the expression of the LRP1B receptor and the Cubilin receptor, but not the LRP or Megalin receptor. RAP appears to antagonize the effect of p97 on those receptors. p97 also appears to induce its own expression as shown by RT-PCR methods (see FIG. 36). FIGS. 37 and 38 summarize the quanitated effects of p97 and RAP on the expression of LRP1B, LRP, LDL-R, Cubilin, p97, and Megalin in the glioblastoma U87 cell line as determined by RT-PCR.

Effect of p97 on Fibroblast Cells.

The fibroblast cell line MG1391 was used to assess the potential of p97 and other LRP ligand conjugates as carriers for transcytosis or endocytosis in fibroblasts. FIG. 39 shows the expression of members of the LDL receptor family in MG1391 cells. LRP, LDL, and to a lesser extent, LRP1B and Cubilin are expressed as measured by RT-PCR. Further more, p97 particularly induces the expression of the LRP1B as shown in FIGS. 40 and 41.

Expression of LDL Receptor Family Members in Human Endothelial Cells and BBCE Cells.

As shown in FIG. 42, LRP, LRP1B, and LDL-R as well as LRP8 are highly expressed in human endothelial cells. The expression of LDL receptor family members in the absence of astrocytes in largely that of LRP5. However, the presence of astrocytes induces the expression of LRP1B and LRP8 in the BBCE cells (see FIG. 43).

The above examples show that the brain p97 uptake, in vivo, is much higher than that of other proteins such as BSA and transferrin. The in vitro model of the BBB used here to characterize the transcytosis of p97 has been used previously for such proteins as transferrin, lactoferrin, low density lipoproteins and insulin (see Dehouck, B. et al. *J. Cell. Biol.* 138: 877-589 (1997), Fillebeen, C. et al. *J. Biol. Chem.* 274: 7011-7017 (1999); Descamps, L., Dehouck, M. P., Torpier, G. & Cecchelli, R. *Am. J. Physiol.* 270: H1149-H1158 (1996)); Frank, H. J., Pardridge, W. M., Morris, W. L., Rosenfeld, R. G. & Choi, T. B. *Diabetes* 35: 654-661 (1986)). As was seen with these proteins, transendothelial transport of p97 requires energy and is concentration-dependent, indicating a receptor-mediated endocytosis mechanism for p97. In addition, preferential transport of p97 from the apical to the basolateral surface of BBCECs is observed with no detectable degradation of p97. The conformation of p97 also seems to be very important for its transcytosis because heat-denaturation considerably reduced the transendothelial transport of this protein. Thus, the in vitro results strongly confirm and support the in vivo observations on high p97 uptake in the brain.

The results show the presence of a low affinity receptor for p97 with a high capacity. Since all the experiments comparing bovine transferrin with human p97 are performed in a heterologous system, we can expect that the binding constant for the p97 receptor would be even greater in a human homologous system. It has been postulated that p97 is an alternate ligand for the transferrin receptor because p97 shares many properties with human transferrin and because the transferrin receptor has been detected in the same tissues as p97. However, our results strongly support that a different mechanism than that involving the transferrin receptor. First, the transcytosis, binding and accumulation of p97 are much higher than those for transferrin indicating that the p97 receptor has a much higher capacity and lower affinity than those previously reported for the transferrin receptor. Second, the transcytosis of p97 is unaffected by either bovine or human transferrin, indicating that p97 does not compete with transferrin for its receptor. Third, the mAb OX-26 directed against the transferrin receptor, which was previously shown to inhibit the uptake of transferrin, has no effect on p97 transport. In addition to the transcytosis experiments using BBCEC monolayers, the competition of [125I]-p97 uptake by unlabelled p97 in isolated human brain capillaries confirmed the presence of a receptor for p97. Moreover, lactoferrin competed [125I]-p97 uptake efficiently, better than transferrin or any other tested proteins, indicating that lactoferrin and p97 share a receptor. The receptor for lactoferrin transcytosis in brain ECs is LRP 6, a member of the large LDL-receptor family. (see Bu, G. & Rennke, S. J. Biol. Chem. 271: 22218-2224(1996)). To further investigate whether LRP could be involved in p97 transcytosis, experiments were performed with BBCEC monolayers in the presence of RAP, a protein which inhibits the binding of ligand to members of the LDL-receptor family (see Bu, G. & Rennke, S. J. Biol. Chem. 271: 22218-2224 (1996); Willnow, T. E, Goldstein, J. L., Orth, K., Brown, M. S. & Herz, J. J. Biol. Chem. 267: 26172-26180 (1992); Bu, G. & Schwartz, A. L. Trends Cell Biol. 8: 272-276 (1998); and Herz, J. & Strickland, D. K. J. Clin. Invest. 108: 779-784 (2001).

Known members of this family also include LDL-R, LRP1B, megalin, VLDL-R, apoE-receptor 2 and the mosaic LDLR-related protein (LR11) (see Hussain, M. M. *Front. Biosci.* 6: D417-D428 (2001); and Liu, C. X., Li, Y., Obermoeller-McCormick, L. M., Schwartz, A. L. & Bu, G. *J. Biol. Chem.* 276: 28889-28896 (2001)). Among these receptors, megalin, is also known to bind lactoferrin (see Hussain, M. M. *Front. Biosci.* 6: D417-D428 (2001); and Willnow T E. *Biol. Chem.* 379: 1025-1031(1998)). However, megalin is mainly expressed in the kidney whereas the major site of LRP expression is in brain. Thus, the diminution of p97 transcytosis by RAP and the inhibition of lactoferrin transcytosis by p97 also indicates that LRP transports p97 across BBCECs.

The concept of using receptor-mediated endocytosis to deliver peptides into the brain was initially described with the findings on the transendothelial transport of insulin across the blood brain barrier (BBB). Subsequent studies demonstrated that a neuropeptide could be delivered into the CNS using receptor-mediated endocytosis by targeting the transferrin receptor with the mAb OX-26 (see Bickel, U., Yoshikawa, T. & Pardridge, W. M. *Adv. Drug Deliv. Rev.* 46: 247-279 (2001) and Pardridge, W. M., Buciak, J. L. & Friden, P. M. *J. Pharmacol. Exp. Ther.* 259: 66-70 (1991)). The development of chimeric proteins containing this mAb, specific linkers and a neurotropic peptide has permitted delivery into the brain of significant levels of this peptide (see Bickel, U., Yoshikawa, T. & Pardridge, W. M. *Adv. Drug Deliv. Rev.* 46: 247-279 (2001); Pardridge, W. M., Wu, D., & Sakane, T. Pharm. Res. 15: 576-582 (1998); and Zhang, Y. & Pardridge, W. M. *Brain Res.* 889:49-56 (2001)). In addition, the transendothelial transport of mAb OX-26 was also reported in these studies to be similar to the transport of human transferrin across the BBB. Our results show that p97 passes across the blood brain barrier (BBB) at least as well as does OX-26. Another advantage of using p97 is its very low concentration in the serum (100 000-fold lower than transferrin) (see Jefferies, W. A. et al. *Brain Res.* 712: 122-126 (1996), and Kim, D. K. et al. S *Neuropsychopharmacology* 25: 84-90 (2001)), which indicates that it would deliver p97-conjugate(s) directly into the CNS.

The results show that intact p97 can cross brain ECs without affecting the integrity of the BBB and with a much higher rate than is seen with transferrin. The inhibition of p97 transcytosis by RAP in BBCEC monolayers and the competition of p97 uptake in brain capillaries by human lactoferrin show that LRP, a member of the LDL-R family, is involved in the transendothelial transport of p97. The results indicate that p97 and, more generally, ligands of the LRP and LRP1B receptors are preferred carriers for conjugation with active agents and preferred modulators for the transport of such conjugates via the LRP or LRP1B receptor.

Each publication, patent application, patent, and other reference cited in any part of the specification is incorporated herein by reference in its entirety to the extent that it is not inconsistent with the present disclosure.

Based on the invention and examples disclosed herein, those skilled in the art will be able to develop other embodiments of the invention. The examples are not intended to limit the scope of the claims set out below in any way. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A sterile composition comprising (a) a conjugate comprising receptor associated protein (RAP) and a chemotherapeutic agent, and (b) a sterile pharmaceutically acceptable carrier wherein the chemotherapeutic agent is selected from the group consisting of an alkylating agent, an alkaloid, an anti-metabolite, and an antibiotic.

2. The composition of claim 1 wherein the chemotherapeutic agent is selected from the group consisting of mechlorethamine hydrochloride, cyclopho sphamide, ifosfamide, chlorambucil, melphalan, busulfan, thiotepa (triethylenethiophosphoramide), carmustine, lomustine, streptozocin, vincristine, vinblastine, paclitaxel, methotrexate, mercaptopurine, thioguanine, fluorouracil, cytarabine, azacitidine, dactinomycin, doxorubicin, daunorubicin, idarubicin, bleomycin, picamycin, mitomycin, hydroxyurea, procarbazine, dacarbazine, cisplatin, carboplatin, asparaginase, etoposide, amsarcrine, mitotane, and mitoxantrone.

* * * * *